United States Patent [19]

Capet et al.

[11] Patent Number: 5,707,991

[45] Date of Patent: Jan. 13, 1998

[54] N-ACYLPYRROLIDINES AND MEDICAMENTS FOR THE TREATMENT OR PREVENTION OF DISORDERS LINKED TO CKK AND TO GASTRIN

[75] Inventors: Marc Capet, Thiais; Marie-Christine Dubroeucq, Enghein Les Bains; Franco Manfre, Limeil-Brevannes, all of France

[73] Assignee: Rhone-Poulenc Rorer S.A., Antony, France

[21] Appl. No.: 448,401

[22] PCT Filed: Jan. 3, 1994

[86] PCT No.: PCT/FR94/00009

§ 371 Date: Jun. 28, 1995

§ 102(e) Date: Jun. 28, 1995

[87] PCT Pub. No.: WO94/15915

PCT Pub. Date: Jul. 21, 1994

[30] Foreign Application Priority Data

Jan. 7, 1993 [FR] France ................... 93 00078

[51] Int. Cl.[6] .................. A61K 31/40; A61K 31/535; C07D 207/08; C07D 411/06
[52] U.S. Cl. .................. 514/235.5; 544/141; 546/208; 548/253; 548/518; 548/533
[58] Field of Search ............. 544/141; 546/208; 548/533; 514/235.5

[56] References Cited

U.S. PATENT DOCUMENTS 4,596,789  6/1986  Dutta et al.
4,691,007  9/1987  Dutta et al.

FOREIGN PATENT DOCUMENTS 0 124 317   11/1984   European Pat. Off.
2 678 938   1/1993    France.
WO 91/13907 9/1991   WIPO.

OTHER PUBLICATIONS

Tetrahedron Letters, vol. 34, No. 3, 1993, Oxford GB, pp. 381–384, V. Maggard et al., "A Convenient Synthesis of the Conformality . . . ".

Tetrahedron Letters, vol. 34, No. 10, 1993, Oxford GB, pp. 1665–1668, J. E. Baldwin et al., "Synthesis of a Bicyclic Gamma–Lactam . . . ".

*Primary Examiner*—Robert W. Ramsuer
*Attorney, Agent, or Firm*—Finnegan, Henderson, Farabow, Garrett & Dunner, L.L.P.

[57] ABSTRACT

The present invention relates to derivatives of formula:

to their salts, to their preparation and to the medicaments containing them.

7 Claims, No Drawings

N-ACYLPYRROLIDINES AND MEDICAMENTS FOR THE TREATMENT OR PREVENTION OF DISORDERS LINKED TO CKK AND TO GASTRIN

The present invention relates to derivatives of formula:

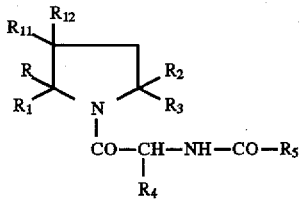

to their salts, to their preparation and to the medicaments containing them.

In the formula (I),

R represents an alkyl radical containing 1 to 12 carbon atoms in an optionally mono- or polyunsaturated, straight or branched chain, a cycloalkyl radical containing 3 to 12 carbon atoms and optionally mono- or polyunsaturated, a polycycloalkyl radical containing 6 to 12 carbon atoms and optionally mono- or polyunsaturated, a phenylalkyl radical in which the phenyl ring is optionally substituted (by one or a number of substituents chosen from alkyl or alkoxy radicals or halogen atoms), a diphenylalkyl radical, a cinnamyl radical, a pyridyl radical optionally substituted by one or a number of alkyl radicals, a furyl radical optionally substituted by one or a number of alkyl radicals, a thienyl radical optionally substituted by one or a number of alkyl radicals, a quinolyl radical optionally substituted by one or a number of alkyl radicals, a naphthyl radical optionally substituted by one or a number of alkyl radicals, an indolyl radical optionally substituted by one or a number of alkyl radicals or a phenyl radical optionally substituted by one or a number of substituents chosen from halogen atoms and alkyl, alkoxy, hydroxyl, nitro, amino, monoalkylamino, dialkylamino, alkoxycarbonyl, —CO—NR$_7$R$_8$, —NH—CO—CH$_3$, trifluoromethyl or trifluoromethoxy radicals, R$_1$ represents a hydrogen atom or an alkyl radical, R$_2$ represents a —(CH$_2$)$_n$—CO—R$_6$, —(CH$_2$)$_m$—O—CO—R"$_6$ or —(CH$_2$)$_m$—NR$_9$R$_{10}$ chain, or an oxazolinyl radical optionally substituted by one or a number of alkyl or 3-alkyloxadiazolyl radicals, R$_3$ represents a hydrogen atom or an alkyl radical, R$_4$ represents a hydrogen atom or an alkyl radical, R$_5$ represents a phenyl radical (optionally substituted by one or a number of substituents chosen from halogen atoms and alkyl, alkoxy and alkylthio radicals), a naphthyl radical, an indolyl radical, a quinolyl radical or a phenylamino radical in which the phenyl ring is optionally substituted by one or a number of substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-SO$_3$—H (in the salt form), —CH=CH-alk', —C(=NOH)—COOX, —S-alk-COOX, —SO-alk-COOX, —SO$_2$-alk-COOX, —O—CH$_2$-alk'-COOX, —CX=N—O-alk-COOX, -alk-N(OH)—CO-alk, -alk-SO$_2$H, —SO$_2$—NH—CO—R$_{13}$, —SO$_2$—NH—SO$_2$—R$_{13}$, —CO—NH—CO—R$_{13}$, —CO—NH—SO$_2$—R$_{13}$, —B(OH)$_2$, —C(NH$_2$)=NOH, —SO$_2$—NH—R$_{14}$, —CO—NH—R$_{14}$,

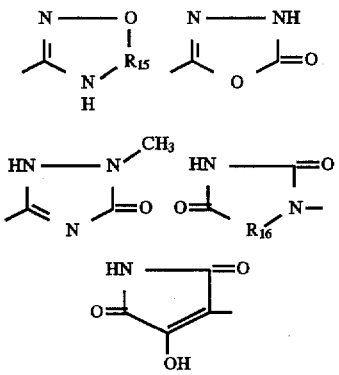

or 2,2-dimethyl-4,6-dioxo-1,3-dioxan-5-yl radicals,

R$_6$ represents a hydroxyl, alkoxy, cycloalkyloxy, cycloalkylalkyloxy, phenyl or —NR$_9$R$_{10}$ radical, R"$_6$ represents an alkoxy, cycloalkyloxy, cycloalkylalkyloxy, phenyl or —NR$_9$R$_{10}$ radical, R$_7$ represents a hydrogen atom or an alkyl radical, phenylalkyl radical or phenyl radical optionally substituted by one or a number of substituents chosen from halogen atoms and alkyl, alkoxy and alkylthio radicals, R$_8$ represents an alkyl radical, phenylalkyl radical or phenyl radical optionally substituted by one or a number of substituents chosen from halogen atoms and alkyl, alkoxy and alkylthio radicals, or else R$_7$ and R$_8$ form, with the nitrogen atom to which they are attached, a saturated or unsaturated, mono- or polycyclic heterocycle containing 4 to 9 carbon atoms and one or a number of heteroatoms (O, N) and optionally substituted by one or a number of alkyl radicals, R$_9$ represents a hydrogen atom or an alkyl radical, cycloalkylalkyl radical, cycloalkyl radical, phenylalkyl radical or phenyl radical optionally substituted by one or a number of substituents chosen from halogen atoms and alkyl, alkoxy and alkylthio radicals, R$_{10}$ represents an alkyl radical, cycloalkylalkyl radical, cycloalkyl radical, phenylalkyl radical or phenyl radical optionally substituted by one or a number of substituents chosen from halogen atoms and alkyl, alkoxy and alkylthio radicals, or else R$_9$ and R$_{10}$ form, together with the nitrogen atom to which they are attached, a saturated or unsaturated, mono- or polycyclic heterocycle containing 4 to 9 carbon atoms and one or a number of heteroatoms (O, N, S) and optionally substituted by one or a number of alkyl radicals, R$_{11}$ represents a hydrogen atom or an alkyl or phenylalkyl radical, R$_{12}$ represents an alkyl, phenylalkyl, phenylsulphonyl, —(CH$_2$)$_p$—CO—R$_{17}$, cyano, —CXO, —CX=NOH, —CX=N—O-alk-COOX, —CHX—OH, —CHX—O—CO-alk, —NH$_2$ or —NH—CO-alk radical, $R_{13}$ represents an alkyl radical, a cycloalkyl radical, a trifluoromethyl radical or a phenyl radical optionally substituted by one or a number of substituents chosen from cyano, alkoxy, nitro or amino radicals and halogen atoms, $R_{14}$ represents a 5-tetrazolyl radical, $R_{15}$ represents C=O or S=O, $R_{16}$ represents O or C=O, $R_{17}$ represents a hydroxyl, alkoxy, cycloalkyloxy, cycloalkylalkyloxy, phenyl, alkyl, phenylalkyloxy or —$NR_9R_{10}$ radical, n is equal to 0, 1 or 2, m is equal to 1 or 2, p is equal to 0 or 1, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical.

In the preceding definitions and those which will be mentioned below, except when otherwise mentioned, the alkyl, alkylene and alkoxy radicals and the alkyl, alkylene and alkoxy portions contain 1 to 4 carbon atoms in a straight or branched chain, the acyl radicals or portions contain 2 to 4 carbon atoms and the cycloalkyl radicals and portions contain 3 to 6 carbon atoms.

When R represents an unsaturated alkyl radical, the latter is preferably an isopropylidene radical.

When R represents a cycloalkyl radical, the latter is preferably a cyclohexyl radical.

When R represents an unsaturated cycloalkyl radical, the latter is preferably a tetrahydrophenyl, cyclopentadiene or dihydrophenyl radical.

When R represents a polycycloalkyl radical, the latter is preferably a norbornyl or adamantyl radical.

When R represents an unsaturated polycycloalkyl radical, the latter is preferably a norbornenyl radical.

When $R_7$ and $R_8$ form, with the nitrogen atom to which they are attached, a heterocycle, the latter is preferably a piperidino ring optionally substituted by one or a number of alkyl radicals or a 1,2,3,4-tetrahydroquinoline ring.

When $R_9$ and $R_{10}$ form, with the nitrogen atom to which they are attached, a heterocycle, the latter is preferably a piperidino, perhydro-1-azepinyl, 1,2,3,6-tetrahydro-1-pyridyl, 1,2,3,4-tetrahydro-1-quinolyl, 1-pyrrolidinyl, 1,2,3, 4-tetrahydro-2-isoquinolyl, thiomorpholino or 1-indolinyl ring, it being possible for these rings to be optionally substituted by at least one alkyl radical.

The compounds of formula (I) containing one or a number of asymmetric centres have isomeric forms. These isomers also form part of the invention.

The compounds of formula (I) for which $R_5$ represents a phenylamino radical in which the phenyl ring is optionally substituted can be prepared by reacting a reactive derivative of carbamic acid, optionally obtained in situ by reacting a reactive derivative of carbonic acid, chosen from N,N'-carbonyldiimidazole, phosgene, diphosgene, triphosgene and p-nitrophenyl chloroformate, with a derivative of formula:

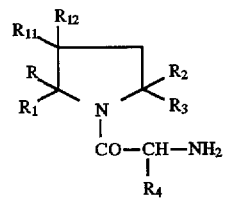

(II)

in which R, $R_1$, $R_2$, $R_3$, $R_4$, $R_{11}$ and $R_{12}$ have the same meanings as in the formula (I), with an aniline in which the phenyl ring is optionally substituted by one or a number of substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-SO₃H (in the salt form), —CH=CH-alk', —C(=NOH)—COOX, —S-alk-COOX, —SO -alk-COOX, —SO₂-alk-COOX, —O—CH₂-alk'-COOX, —CX=N—O-alk-COOX, -alk-N (OH)—CO-alk, -alk-SO₂H, —SO₂—NH—CO—$R_{13}$, —SO₂—NH—SO₂—$R_{13}$, —CO—NH—CO—$R_{13}$, —CO—NH—SO₂—$R_{13}$, —B(OH)₂, —C(NH₂)=NOH, —SO₂—NH—$R_{14}$, —CO—NH—$R_{14}$,

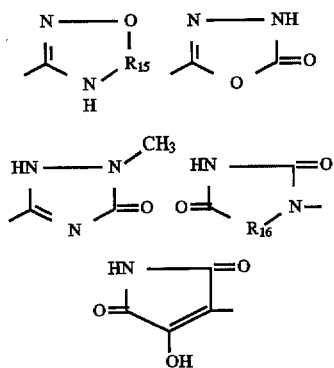

or 2,2-dimethyl-4,6-dioxo-1,3-dioxan-5-yl radicals.

This reaction is generally carried out in an inert solvent such as tetrahydrofuran, N,N-dimethylformamide, a chlorinated solvent (chloroform or 1,2-dichloroethane, for example) or an aromatic solvent (benzene or toluene, for example) at a temperature between 20° C. and the boiling temperature of the solvent.

The reactive derivative of carbamic acid can be obtained under the same solvent and temperature conditions.

The derivatives of formula (II) can be obtained by deprotection of a derivative of formula:

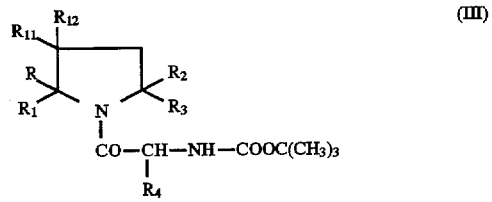

(III)

in which R, $R_1$, $R_2$, $R_3$, $R_4$, $R_{11}$ and $R_{12}$ have the same meanings as in the formula (I).

This deprotection is preferably carried out by means of iodotrimethylsilane in an inert solvent such as a chlorinated solvent (chloroform or 1,2-dichloroethane, for example) or acetonitrile, at a temperature between 15° and 40° C.

The derivatives of formula (III) for which $R_2$ represents a —$(CH_2)_n$—CO—$R_6$ chain, $R_6$ not being a hydroxyl radical, and $R_{12}$ represents an alkyl, phenylalkyl, phenylsulphonyl, cyano, —CXO or —$(CH_2)_p$—CO—$R_{17}$ radical, $R_{17}$ not being a hydroxyl radical, can be obtained by reacting a derivative of formula:

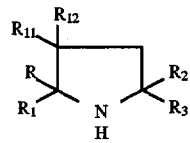

in which R, $R_1$, $R_3$ and $R_{11}$ have the same meanings as in the formula (I) and $R_2$ and $R_{12}$ have the same meanings as above, with an acid of formula:

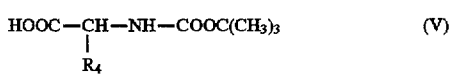

in which $R_4$ is defined as in the formula (I).

This reaction is carried out in an inert solvent such as acetonitrile, tetrahydrofuran or a chlorinated solvent in the presence of a condensation agent used in peptide chemistry such as a carbodiimide (N,N'-dicyclohexylcarbodiimide, for example) or an alkyl chloroformate at a temperature between 10° and 40° C.

The derivatives of formula (V) can be obtained according to the usual methods for protecting amino acids.

The derivatives of formula (IV) for which $R_2$ represents a —$(CH_2)_n$—CO—$R_6$ chain, n being equal to 0 and $R_6$ not being hydroxyl, and $R_{12}$ represents a cyano, phenylsulphonyl, —CXO or —$(CH_2)_p$—CO—$R_{17}$ radical, p being equal to 0 and $R_{17}$ not being a hydroxyl radical, can be obtained by reacting a derivative of formula:

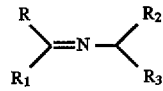

in which R, $R_1$ and $R_3$ have the same meanings as in the formula (I) and $R_2$ has the same meanings as above, with a derivative of formula:

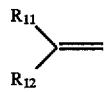

in which $R_{11}$ has the same meanings as in the formula (I) and $R_{12}$ has the same meanings as above.

This reaction is carried out in an inert solvent such as acetonitrile, tetrahydrofuran or toluene in the presence of a metal salt such as silver acetate, lithium bromide, magnesium bromide, sodium iodide or zinc iodide and of a nitrogenous base such as triethylamine at a temperature between 0° C. and the boiling temperature of the reaction mixture.

The derivatives of formula (VII) are marketed or can be obtained by adaptation of the methods described by G. H. Dewar et al., Eur. J. Med. Chem., 20, 228 (1985), Elles, Chimie Modems [Modern Chemistry], volume 4, 53 (1959) and in Patent DE 752,481.

The derivatives of formula (VI) can be obtained by reacting a ketone R—CO—$R_1$, in which R and $R_1$ have the same meanings as in the formula (I), with an amine $H_2N$—$CH(R_2)R_3$ in which $R_2$ has the same meanings as above and $R_3$ has the same meanings as in the formula (I).

This reaction is generally carried out either by means of a dehydrating agent such as 4 Å molecular sieves in an inert solvent such as dichloromethane at a temperature between 0° C. and the boiling temperature of the reaction mixture, or else by azeotropic distillation of the water in an aromatic solvent such as toluene, optionally in the presence of an acid such as paratoluenesulphonic acid.

The derivatives of formula (IV) for which $R_2$ represents a —$(CH_2)_n$—CO—$R_6$ chain, n is equal to 0, $R_{12}$ represents a cyano, phenylsulphonyl, —CXO or —$(CH_2)_p$—CO—$R_{17}$ radical, p is equal to 0 and $R_{17}$ represents an alkoxy, cycloalkyloxy, phenylalkyloxy or cycloalkylalkyloxy radical can also be obtained by adaptation of the methods described by S. Kanemasa et al., Bull. Chem. Soc. Japan, 62, 869 (1982); D. A. Barr et al., J. Chem. Soc. Perkin Trans. I, 1550 (1989) and O. Tsuge et al., J. Org. Chem., 53, 1384 (1988).

The derivatives of formula (IV) for which $R_1$ represents an alkyl radical, $R_2$ represents a —$(CH_2)_n$—CO—$R_6$ chain, n being equal to 0 and $R_6$ not being hydroxyl, and $R_{12}$ represents an alkyl, phenylalkyl or —$(CH_2)_p$—CO—$R_{17}$ radical, and $R_{17}$ is not a hydroxyl radical, can be obtained by reacting a derivative of formula:

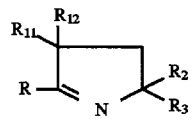

in which R and $R_3$ have the same meanings as in the formula (I) and $R_2$ has the same meanings as above, with a derivative of formula:

in which $R_1$ represents an alkyl radical and $R_1$—M represents an organomagnesium derivative or an organolithium derivative.

This reaction is carried out in an inert solvent such as tetrahydrofuran or ether in the presence of a Lewis acid such as boron trifluoride or titanium tetrachloride at a temperature between −78° C. and the boiling temperature of the reaction mixture.

The derivatives of formula (VIII) for which $R_3$ represents an alkyl radical can be obtained by reacting a corresponding derivative of formula (VIII) for which $R_3$ represents a hydrogen atom with a derivative of formula Hal-$R_3$ in which $R_3$ represents an alkyl radical and Hal represents a halogen, and preferably iodine, atom.

This reaction is generally carried out in an inert solvent such as tetrahydrofuran or ether in the presence of a base such as sodium hydride or the sodium or lithium salt of hexamethyldisilazane at a temperature between −78° C. and the boiling temperature of the reaction mixture.

The derivatives of formula (VIII) for which $R_3$ represents a hydrogen atom can be obtained by deprotection and dehydration of a derivative of formula:

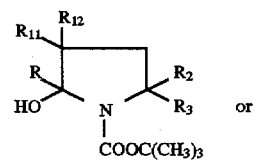

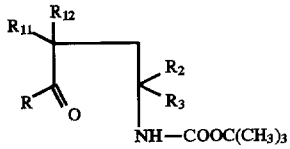

in which R, $R_2$, $R_3$, $R_{11}$ and $R_{12}$ have the same meanings as above, or of a mixture of these derivatives.

These deprotection and dehydration operations are generally carried out by means of trifluoroacetic acid or iodotrimethylsilane in an inert solvent such as a chlorinated solvent (dichloromethane, for example) at a temperature in the region of 20° C.

The derivatives of formulae (X) and (XI) can be obtained, by adaptation of the methods described by J. Ezquerra et al., Tetrahedron Lett., 34, 6317 (1993), by reacting a derivative of formula:

in which R has the same meanings as above and R—M represents an organomagnesium or organolithium derivative or a cuprate, with a derivative of formula:

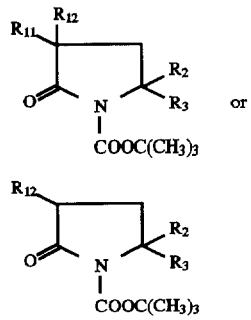

in which $R_2$, $R_3$, $R_{11}$ and $R_{12}$ have the same meanings as above.

This reaction is carried out in an inert solvent such as tetrahydrofuran at a temperature between $-78°$ C. and $20°$ C.

The derivatives of formula (XIII) for which $R_{11}$ represents an alkyl or phenylalkyl radical, $R_{12}$ represents an alkyl, phenylalkyl or —$(CH_2)_p$—CO—$R_{17}$ radical and $R_{17}$ is not a hydroxyl radical can be obtained by reacting a derivative of formula (XIV), in which $R_2$ and $R_3$ have the same meanings as above, with a derivative of formula $R_{11}$–$R_{18}$ in which $R_{18}$ represents a halogen, and preferably bromine, atom or a tosyl residue and $R_{11}$ represents an alkyl or phenylalkyl radical.

This reaction is generally carried out in an inert solvent such as tetrahydrofuran in the presence of a base such as lithium diisopropylamide or a sodium or lithium salt of hexamethyldisilazane at a temperature between $-78°$ C. and the boiling temperature of the reaction mixture.

The derivatives of formula (XIV) can be obtained, by adaptation of the methods described by N. Langlois et al., Tetrahedron Lett., 34, 2477 (1993), J. E. Baldwin et. al., Tetrahedron, 45, 7459 (1989), J. Ezquerra et al., Tetrahedron, 49, 8665 (1993), by reacting a derivative of fomula:

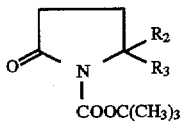

in which $R_2$ and $R_3$ have the same meanings as above, with a derivative of formula $R_{12}$–$R_{18}$ in which $R_{18}$ represents a halogen, and preferably bromine, atom or a tosyl residue and $R_{12}$ has the same meanings as above.

The derivatives of formula (XV) can be obtained by reacting di-tert-butyl dicarbonate with a derivative of formula:

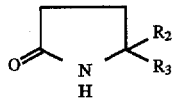

in which $R_2$ and $R_3$ have the same meanings as above.

This reaction is generally carried out in the presence of triethylamine or 4-dimethylaminopyridine in a chlorinated solvent such as dichloromethane at a temperature in the region of 20° C.

The derivatives of formula (XVI) are marketed or can be obtained by esterification of pyroglutamic acid according to the methods described by M. Hollosi et al., Acta Chim. (Budapest), 71, 101 (1972), B. Rigo et al., J. Heterocycl. Chem., 25, 49 (1988), J. H. Billmann and J. L. Randall, J. Am. Chem. Soc., 66, 745 (1944), R. B. Angier and V. K. Smith, J. Org. Chem., 21, 1540 (1956), J. C. Sauer and H. Adkins, J. Am. Chem. Soc., 60, 402 (1938).

The derivatives of formula (IV) for which $R_2$ represents a —$(CH_2)_n$—CO—$R_6$ chain and n is equal to 1 or 2 can be obtained by adaptation of the methods described by S. Rosset et al., Tetrahedron Lett., 32, 7521 (1991), T. Gallagher et al., J. Chem. Soc. Perkin Trans. I, 2193 (1991) and J. F. W. Keana, J. Org. Chem., 48, 2644 (1983).

The derivatives of formula (IV) for which $R_1$ represents a hydrogen atom, $R_2$ represents a —$(CH_2)_n$—CO—$R_6$ chain, n is equal to 0, $R_{12}$ represents an alkyl, phenylalkyl or —$(CH_2)_p$—CO—$R_{17}$ radical and $R_7$ is not a hydroxyl radical can be obtained by hydrogenation of the corresponding derivatives of formula (VIII) for which R and $R_3$ have the same meanings as in the formula (I) and $R_1$, $R_2$ and $R_{12}$ have the same meanings as above.

This hydrogenation is preferably carried out by means of hydrogen in the presence of a catalyst such as platinum oxide in an inert solvent such as ethanol at a temperature in the region of 20° C., or by means of sodium borohydride end potassium carbonate in a water/alcohol (preferably ethanol) mixture at a temperature between 0° and 20° C.

The derivatives of formula (III) for which $R_6$ and/or $R_{17}$ represent a hydroxyl radical can be obtained by hydrolysis or, depending on the situation, hydrogenolysis of the corresponding esters of formula (III).

When alkyl or phenylalkyl esters are used, it is advantageous to carry out the hydrolysis by means of a base such as sodium hydroxide, potassium hydroxide or lithium hydroxide in an inert solvent such as tetrahydrofuran, dioxane, water, methanol or a mixture of these solvents at a temperature between 20° and 40° C. When phenylalkyl esters are used, it can also be advantageous to carry out a hydrogenolysis by means of hydrogen or ammonium formate in the presence of a catalyst such as palladium-on-charcoal in a solvent such as methanol or ethyl acetate.

The derivatives of formula (III) for which $R_2$ represents a —$(CH_2)_m$—O—CO—$R''_6$ chain can be obtained by reacting a derivative of formula:

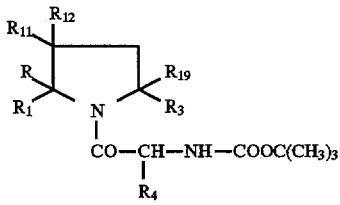
(XVII)

in which R, $R_1$, $R_3$, $R_4$, $R_{11}$ and $R_{12}$ have the same meanings as in the formula (I) and $R_{19}$ represents a —$(CH_2)_m$—OH chain, either with a halide of formula Hal-CO—$R''_6$, in which Hal represents a halogen atom and $R''_6$ has the same meanings as in the formula (I), or with an anhydride of formula $(R''_6CO)_2O$ in which $R''_6$ has the same meanings as in the formula (I).

This reaction is carried out in an inert solvent such as a chlorinated solvent in the presence of a trialkylamine at a temperature between 20° C. and the boiling temperature of the reaction mixture.

The derivatives of formula (XVII) can be obtained by reduction of a corresponding derivative of formula (III) for which $R_2$ represents a —$(CH_2)_n$—CO—$R_6$ chain, n is equal to 0 or 1 and $R_6$ represents a hydroxyl or alkoxy radical.

This reaction is carried out in an alcohol (methanol, ethanol or tert-butanol), tetrahydrofuran or a mixture of these solvents in the presence of sodium borohydride or diborane at a temperature between 20° C. and the boiling temperature of the reaction mixture.

The derivatives of formula (III) for which $R_2$ represents a —$(CH_2)_m$—O—CO—$R''_6$ chain, $R''_6$ represents an —$NR_9R_{10}$ radical and $R_9$ represents a hydrogen atom can also be obtained by condensation of a derivative of formula (XVII) in which $R_{19}$ represents a —$(CH_2)_m$—OH chain, with an isocyanate of formula $R_{10}NCO$.

This reaction is carried out in an inert solvent such as a chlorinated solvent, tetrahydrofuran or N,N-dimethylformamide, optionally in the presence of a catalytic amount of an alkali metal alkoxide, at a temperature between 20° C. and the boiling temperature of the reaction mixture.

The derivatives of formula (III) for which $R_2$ represents a —$(CH_2)_m$—$NR_9R_{10}$ radical can be obtained by reacting an amine $HNR_9R_{10}$, in which $R_9$ and $R_{10}$ have the same meanings as in the formula (I), with a derivative of formula (XVII) in which $R_{19}$ represents a —$(CH_2)_m$—O—$SO_2$—$CH_3$ radical.

This reaction is generally carried out either in the presence of a large excess of amine at a temperature between 0° and 10° C. or, when the hydrochloride of the amine is used, in a chlorinated solvent in the presence of a trialkylamine at a temperature between 20° C. and the boiling temperature of the reaction mixture.

The derivatives of formula (XVII) in which $R_{19}$ represents a —$(CH_2)_m$—O—$SO_2$—$CH_3$ radical can be obtained by reacting a corresponding derivative of formula (XVII), for which $R_{19}$ represents a —$(CH_2)_m$—OH radical, with methanesulphonyl chloride.

This reaction is generally carried out in an inert solvent such as acetonitrile or methylene chloride in the presence of triethylamine at a temperature between 0° C. and the boiling temperature of the reaction mixture.

The derivatives of formula (III) for which $R_2$ represents a —$(CH_2)_n$—CO—$R_6$ radical and $R_6$ represents a hydroxyl radical can be obtained by saponification of a corresponding derivative of formula (III) for which $R_6$ represents an alkoxy radical.

This reaction is carried out in inert solvents such as methanol, dioxane, tetrahydrofuran and water or a mixture of these solvents in the presence of a base such as sodium hydroxide, potassium hydroxide or lithium hydroxide at a temperature between 0° and 25° C.

The derivatives of formula (III) for which $R_2$ represents a —$(CH_2)_n$—CO—$R_6$ radical and $R_6$ represents an alkoxy, cycloalkoxy or cycloalkylalkyloxy radical can be obtained by esterification of the corresponding derivatives of formula (III) for which $R_2$ represents a —$(CH_2)_n$—CO—$R_6$ radical and $R_6$ represents a hydroxyl radical.

This reaction is preferably carried out by means of an alcohol $R_{20}$—OH in which $R_{20}$ represents an alkyl, cycloalkyl or cycloalkylalkyl radical in the presence of tosyl chloride in pyridine at a temperature between 0° and 25° C.

The derivatives of formula (III) for which $R_2$ represents a —$(CH_2)_n$—CO—$R_6$ radical and $R_6$ represents a phenyl radical can be obtained by reacting a corresponding derivative of formula (III) for which $R_2$ represents a —$(CH_2)_n$—CO—$R_6$ radical and $R_6$ represents an alkoxy radical with phenylmagnesium bromide.

This reaction is preferably carried out in an inert solvent such as tetrahydrofuran or ethyl ether at a temperature between −70° C. and the boiling temperature of the reaction mixture.

The derivatives of formula (III) for which $R_2$ represents an optionally substituted oxazolinyl radical can be obtained by reacting a corresponding derivative of formula (III), for which $R_2$ represents a —$(CH_2)_n$—CO—$R_6$ radical, n is equal to 0 and $R_6$ represents a hydroxyl radical, with 2-aminoethanol optionally substituted by one or a number of alkyl radicals.

This reaction is carried out in an inert solvent such as toluene, the water formed being removed, at the boiling temperature of the reaction mixture.

The derivatives of formula (III) for which $R_2$ represents a 3-alkyloxadiazolyl radical can be obtained by reacting a corresponding derivative of formula (III), for which $R_2$ represents a —$(CH_2)_n$—CO—$R_6$ radical, n is equal to 0 and $R_6$ represents an alkoxy radical, with an alkylamidoxime.

This reaction is carried out in an inert solvent such as tetrahydrofuran in the presence of sodium hydride at a temperature between 25° C. and the boiling temperature of the reaction mixture.

The derivatives of formula (III) for which $R_{12}$ represents a —CHX—O—CO-alk radical can be obtained by reacting derivatives of formula (III) in which $R_{12}$ represents a —CHX—OH radical with a derivative of formula Hal-CO-alk in which Hal represents a halogen atom (bromine and chlorine, preferably) and alk represents an alkyl radical or a derivative of formula (alk-CO)$_2$O in which alk represents an alkyl radical.

This reaction is carried out in an inert solvent such as a chlorinated solvent in the presence of an organic base such as a trialkylamine at a temperature between 20° C. and the boiling temperature of the reaction mixture.

The derivatives of formula (III) for which $R_{12}$ represents a —CHX—OH radical can be obtained by reduction of the compounds of formula (III) in which $R_{12}$ represents a —CXO radical.

This reduction is generally carried out by means of sodium borohydride or diborane in a solvent such as an alcohol (methanol, ethanol or tert-butanol, for example), tetrahydrofuran or a mixture of these solvents at a temperature between −20° C. and the boiling temperature of the reaction mixture.

The derivatives of formula (III) for which $R_{12}$ represents a —NH—CO-alk radical can be obtained by reacting the compounds of formula (III) in which $R_{12}$ represents an $NH_2$ radical with a derivative of formula Hal-CO-alk in which Hal represents a halogen atom (bromine and chlorine, preferably) or a derivative of formula (alk-CO)$_2$O.

This reaction is carried out in an inert solvent such as a chlorinated solvent in the presence of an organic base such as a trialkylamine at a temperature between 20° C. and the boiling temperature of the reaction mixture.

The derivatives of formula (III) for which $R_{12}$ represents an —$NH_2$ radical can be obtained by reacting the compounds of formula (III), in which $R_{12}$ represents a —$(CH_2)_p$—CO—$R_{17}$ radical, p is equal to 0 and $R_{17}$ represents a hydroxyl radical, with diphenylphosphoryl azide followed by hydrolysis of the intermediate obtained.

This reaction is generally carried out in the presence of triethylamine in a solvent such as an alcohol (methanol, ethanol or tert-butanol, for example), tetrahydrofuran or a mixture of these solvents at a temperature between –20° C. and the boiling temperature of the reaction mixture. Hydrolysis is generally carried out by addition of water or an acid to the reaction mixture at a temperature between –20° C. and the boiling temperature of the reaction mixture.

The derivatives of formula (III) for which $R_2$ represents a —$(CH_2)_n$—CO—$R_6$ chain and $R_6$ represents an —$NR_9R_{10}$ radical can be obtained by reacting a corresponding derivative of formula (III) for which $R_6$ represents a hydroxyl radical or a reactive derivative of this acid with an amine of formula $HNR_9R_{10}$ in which $R_9$ and $R_{10}$ have the same meanings as in the formula (I).

When the acid is used, the reaction is carried out in the presence of a condensation agent used in peptide chemistry such as a carbodiimide (for example N,N'-dicyclohexylcarbodiimide) or N,N'-carbonyldiimidazole in an inert solvent such as an ether (tetrahydrofuran or dioxane, for example), an amide (N,N-dimethylformamide) or a chlorinated solvent (methylene chloride, 1,2-dichloroethane or chloroform, for example) at a temperature between 0° C. and the reflux temperature of the reaction mixture.

When a reactive derivative of the acid is used, it is possible to react the anhydride, a mixed anhydride or an ester (which can be chosen from the activated or non-activated esters of the acid).

The reaction is then carried out either in organic medium, optionally in the presence of an acid acceptor such as a nitrogenous organic base (trialkylamine, pyridine, 1,8-diazabicyclo[5.4.0]undec-7-ene or 1,5-diazabicyclo[4.3.0]non-5-ene, for example), in a solvent such as mentioned above or a mixture of these solvents at a temperature between 0° C. and the reflux temperature of the reaction mixture, or in a two-phase water/organic medium in the presence of an alkali metal or alkaline-earth metal base (sodium hydroxide, potassium hydroxide) or an alkali metal or alkaline-earth metal carbonate or bicarbonate at a temperature between 0° and 40° C.

The optionally substituted anilines are marketed or can be obtained by application or adaptation of the methods described by R. Schröter, Methoden der organisthen Chemie, Houben Well, Volume XI/1, p 360, G. J. Esselen et al., J. Am. Chem. Soc., 36, 322 (1914), G. Adriant et al., Bull. Soc. Chim. Fr., 1511 (1970), W. A. Jacobs et al., J. Am. Chem. Soc., 39, 2438 (1917) and J. Am. Chem. Soc., 39, 1438 (1917) and in the examples.

The compounds of formula (I) for which $R_5$ represents a phenylamino radical in which the phenyl ring is optionally substituted by one or a number of substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-SO$_3$H (in the salt form), —O-alk-COOX, —CH=CH—COOX, —CO—COOX, —S-alk-COOX, —SO-alk-COOX, —SO$_2$-alk-COOX, —O—CH$_2$-alk'-COOX, —CX=N—O-alk-COOX, -alk-COOX or -alk'-COOX radicals in which X is other than a hydrogen atom can also be prepared by reacting a derivative of formula (II) with a phenyl isocyanate in which the phenyl ring is optionally substituted by one or a number of substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-SO$_3$H (in the salt form), —O-alk-COOX, —CH=CH—COOX, —CO—COOX, —S-alk-COOX, —SO-alk-COOX, —SO$_2$-alk-COOX, —O—CH$_2$-alk'-COOX, —CX—N—O-alk-COOX, -alk-COOX or -alk'-COOX radicals in which X is other than a hydrogen atom.

This reaction is generally carried out in an inert solvent such as tetrahydrofuran, N,N-dimethylformamide, a chlorinated solvent (chloroform or 1,2-dichloroethane, for example) or an aromatic solvent (benzene or toluene, for example) at a temperature between 10° C. and the boiling temperature of the solvent.

The phenyl isocyanates are marketed or can be obtained by application or adaptation of the methods described by R. Richter et al., The Chemistry of Cyanate and their Thio Derivatives, S. Patai, Part 2, Wiley, New York (1977) and in the examples.

The compounds of formula (I) for which $R_5$ represents a naphthyl, indolyl, quinolyl or optionally substituted phenyl radical can be prepared by reacting a derivative of formula (II) with an acid of formula HOOC—$R_5$ in which $R_5$ has the same meanings as above or a reactive derivative of this acid.

When the acid is used, the reaction is carried out in the presence of a condensation agent used in peptide chemistry such as a carbodiimide (for example N,N'-dicyclohexylcarbodiimide) or N,N'-carbonyldiimidazole in an inert solvent such as an ether (tetrahydrofuran or dioxane, for example), an amide (N,N-dimethylformamide) or a chlorinated solvent (methylene chloride, 1,2-dichloroethane or chloroform, for example) at a temperature between 0° C. and the reflux temperature of the reaction mixture.

When a reactive derivative of the acid is used, it is possible to react the anhydride, a mixed anhydride or an ester (which can be chosen from the activated or non-activated esters of the acid).

The reaction is then carried out either in organic medium, optionally in the presence of an acid acceptor such as a nitrogenous organic base (trialkylamine, pyridine, 1,8-diazabicyclo [5.4.0]undec-7-ene or 1,5-diazabicyclo[4.3.0]non-5-ene, for example), in a solvent such as mentioned above or a mixture of these solvents at a temperature between 0° C. and the reflux temperature of the reaction mixture, or in a two-phase water/organic medium in the presence of an alkali metal or alkaline-earth metal base (sodium hydroxide, potassium hydroxide) or an alkali metal or alkaline-earth metal carbonate or bicarbonate at a temperature between 0° and 40° C.

The compounds of formula (I) for which $R_5$ represents a phenylamino radical in which the phenyl ring is substituted by a carboxyl, -alk-COOH, —O-alk-COOH, -alk'-COOH, —CH=CH—COOH, —CO—COOH, —S-alk-COOH, —SO-alk-COOH, —SO$_2$-alk-COOH, —C(=NOH)—COOH, —O—CH$_2$-alk'-COOH or —CX=N—O-alk-COOH radical and/or $R_{12}$ represents a —$(CH_2)_p$—COOH radical, and R, $R_1$, $R_2$, $R_3$, $R_4$, $R_6$, $R_{11}$ and $R_{12}$ are defined as in the formula (I), can also be prepared by hydrolysis or, according to the situation, hydrogenolysis of the corresponding esters of formula (I).

When the alkyl or phenylalkyl esters are used, it is advantageous to carry out the hydrolysis by means of a base such as sodium hydroxide, potassium hydroxide or lithium hydroxide in an inert solvent such as tetrahydrofuran, dioxane, water, methanol or a mixture of these solvents at a temperature between 20° C. and 40° C. When phenylalkyl esters are used, it is can also be advantageous to carry out a hydrogenolysis by means of hydrogen or ammonium formate in the presence of a catalyst such as palladium-on-charcoal in a solvent such as methanol or ethyl acetate. When tert-butyl esters are used, it is advantageous to carry out the hydrolysis by means of an acid such as trifluoroacetic acid.

The compounds of formula (I) for which $R_5$ represents a phenylamino radical in which the phenyl ring is substituted by a hydroxyiminoalkyl or alkoxyiminoalkyl radical can also be prepared by reacting the corresponding acylated derivative of formula (I) with a derivative of formula:

  (XVIII)

in which $R_{21}$ represents a hydrogen atom or an alkyl radical.

This reaction is generally carried out in an inert solvent such as an alcohol (methanol or ethanol, for example), water or a mixture of these solvents at the boiling temperature of the solvent and optionally in the presence of a base such as pyridine.

The compounds of formula (I) for which $R_2$ represents a —$(CH_2)_n$—CO—$R_6$ chain, $R_6$ not being a hydroxyl radical, $R_{12}$ represents an alkyl, phenylalkyl, phenylsulphonyl, cyano, —CXO or —$(CH_2)_p$—CO—$R_{17}$ radical, $R_{17}$ not being a hydroxyl radical, and $R_5$ represents a naphthyl, indolyl, quinolyl or optionally substituted phenyl radical or a phenylamino radical in which the phenyl ring is optionally substituted by one or a number of substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH═CH-alk', -alk-O-alk, trifluoromethylsulphonamido, -alk-$SO_3$H (in the salt form), —O-alk-COOX, —CH═CH—COOX, —CO—COOX, —S-alk-COOX, —SO-alk-COOX, —$SO_2$-alk-COOX, —O—$CH_2$-alk'-COOX, —CX═N—O-alk-COOX, -alk-COOX or -alk'-COOX radicals in which X is other than a hydrogen atom can also be prepared by reacting a derivative of formula (IV) in which $R_2$ and $R_{12}$ have the same meanings as above with an acid of formula:

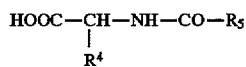  (XIX)

in which $R_5$ has the same meanings as above or a reactive derivative of this acid and $R_4$ has the same meanings as in the formula (I).

This reaction is preferably carried out in the presence of a condensation agent used in peptide chemistry such as a carbodiimide in a solvent such as acetonitrile, tetrahydrofuran or a chlorinated solvent or by means of thionyl chloride in dichloromethane at a temperature between 10° C. and the boiling temperature of the solvent.

The acids of formula (XIX) can be obtained by application or adaptation of the method described by J. R. Johnson et al., J. Am. Chem. Soc., 69, 2370 (1947) or, for the compounds for which $R_5$ represents an optionally substituted phenylamino radical, by reacting a phenyl isocyanate in which the phenyl ring is optionally substituted by one or a number of substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH═CH-alk', -alk-O-alk, trifluoromethylsulphonamido, -alk-$SO_3$H (in the salt form), —O-alk-COOX, —CH═CH—COOX, —CO—COOX, —S-alk-COOX, —SO-alk-COOX, —$SO_2$-alk-COOX, —O—$CH_2$-alk'-COOX, —CX═N—O-alk-COOX, -alk-COOX or -alk'-COOX radicals in which X is other than a hydrogen atom with a derivative of formula:

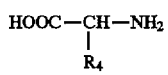

in which $R_4$ has the same meanings as in the formula (I).

This reaction is generally carried out in an aqueous solution in the presence of a base such as an alkali metal bicarbonate or in aqueous dioxane at a temperature in the region of 20° C.

The compounds of formula (I) for which $R_{12}$ represents a —CX═N—O-alk-COOX or —CX—NOH radical can be obtained by condensation of a derivative of formula (XVIII), in which $R_{21}$ represents a hydrogen atom or alk-COOX, with a corresponding compound of formula (I) for which $R_{12}$ represents a —CXO radical.

This reaction is generally carried out in an inert solvent such as an alcohol (methanol or ethanol, for example), water or a mixture of these solvents, optionally in the presence of a base such as pyridine, at a temperature between 20° C. and the boiling temperature of the reaction mixture.

It is understood, for a person skilled in the art, that the use of the processes according to the invention described above it may be necessary, in order to prevent side reactions, to introduce protective groups of the amine, alcohol, acid or ketone functional groups such as those described by T. W. Greene, protective groups in organic synthesis, John Wiley and Sons, New York. For example, the amine functional groups can be blocked in the form of tert-butyl or methyl carbamates and then regenerated by means of iodotrimethylsilane or of benzyl carbamates and then regenerated by hydrogenolysis after having implemented the process according to the invention. The alcohol functional groups can, for example, be blocked in the benzoate form and then regenerated by hydrolysis in alkaline medium after having implemented the process according to the invention. The ketone functional groups can be blocked in the 1,3-dioxolane form and then regenerated by means of a hydrochloric acid/acetic acid mixture.

The enantiomers of the compounds of formula (I) containing at least one asymmetric site can be obtained by resolution of the racemates, for example by chromatography on a chiral column, or by synthesis from chiral precursors.

The compounds of formula (I) can be purified by the standard known methods, for example by crystallization, chromatography or extractions.

The compounds of formula (I) containing a basic residue can optionally be converted to addition salts with an inorganic or organic acid by reacting with such an acid in an organic solvent such as an alcohol, a ketone, an ether or a chlorinated solvent.

The compounds of formula (I) containing an acid residue can optionally be converted to metal salts or to addition salts with nitrogenous bases according to methods known per se. These salts can be obtained by reacting a metal base (alkali metal or alkaline-earth metal, for example), ammonia, an amine or a salt of an amine with a compound of formula (I) in a solvent. The salt formed is separated by the standard methods.

These salts also form part of the invention.

Mention may be made, as examples of pharmaceutically acceptable salts, of the addition salts with inorganic or organic acids (such as acetate, propionate, succinate, benzoate, fumarate, maleate, oxalate, methanesulphouate, isethionate, theophyllineacetate, salicylate, methylenebis(β-oxynaphthoate), hydrochloride, sulphate, nitrate and phosphate), the salts with alkali metals (sodium, potassium or lithium) or with alkaline-earth metals (calcium or magnesium), the ammonium salt or the salts of nitrogenous bases (ethanolamine, trimethylamine, methylamine, benzylamine, N-benzyl-β-phenethylamine, choline, arginine, leucine, lysine or N-methylglucamine).

The compounds of formula (I) have advantageous pharmacological properties. These compounds have a strong affinity for cholecystokinin (CCK) and gastrin receptors and are thus useful in the treatment and prevention of disorders linked to CCK and to gastrin in the nervous system and the gastrointestinal system.

These compounds can therefore be used for the treatment or prevention of psychoses, of anxious disorders, of depression, of neurodegeneration, of panic attacks, of Parkinson's disease, of tardive dyskinesia, of irritable bowel syndrome, of acute pancreatitis, of ulcers, of disorders of intestinal motility, of certain tumours sensitive to CCK, as appetite regulators, in weaning from chronic treatments and alcohol or medicinal abuse and as constrictors of the pupil of the eye.

These compounds also have a potentiating effect on the analgesic activity of narcotic and non-narcotic medicaments. They can additionally have a specific analgesic effect.

Moreover, the compounds having a strong affinity for CCK receptors modify memorizing abilities. These compounds can consequently be effective in memory disorders.

The affinity of the compounds of formula (I) for CCK recaptots was determined according to a technique inspired by that of A. Saito et al. (J. Neuro. Chem., 37, 483–490 (1981)) in the cerebral cortex and in the pancreas.

In these tests, the $IC_{50}$ of the compounds of formula (I) is generally less than or equal to 2000 nM.

Moreover, it is known that the products which recognize the central receptors of CCK have a similar specificity for the recaptors of gastrin in the gastrointestinal tract (Bock et al., J. Med. Chem., 32, 16–23 (1989), Reyfeld et al., Am. J. Physiol., 240, G255–266 (1981), Beinfeld et al., Neuropeptides, 3, 411–427 (1983).

The compounds of formula (I) have a low toxicity. Their subcutaneous $LD_{50}$ in mice is generally greater than 40 mg/kg.

The compounds of formula (I) for which R represents a phenyl radical optionally substituted by one or a number of halogen atoms, $R_1$ represents a hydrogen atom, $R_2$ represents a —$(CH_2)_n$—CO—$R_6$ chain, $R_3$ represents a hydrogen atom, $R_4$ represents a hydrogen atom, $R_5$ represents a phenylamino radical in which the phenyl ring is substituted by one or a number of substituents chosen from carboxyl, —S-alk-COOX, -alk-COOX and 5-tetrazolyl radicals, $R_6$ represents a hydroxyl or alkoxy radical, $R_{11}$ represses a hydrogen atom, $R_{12}$ represents a phenylsulphonyl or —$(CH_2)_p$—CO—$R_{17}$ radical, $R_{17}$ represents a hydroxyl, phenyl or $NR_9R_{10}$ radical, p is equal to 0, n is equal to 0 and X represents a hydrogen atom, their salts and their isomers are particularly advantageous.

The following compounds are particularly advantageous:

(2RS,4SR,5RS)-3-{3-[2-(2-tert-butoxycarbonyl-5-phenyl-4-phenylsulphonyl-1-pyrrolidinyl)-2-oxoethyl]ureido}benzoic acid, 2-tert-butyl hydrogen (2RS,4SR,5SR)-1-{2-[3-(3-(carboxymethylthio)phenyl)ureido]acetyl}-5-phenylpyrrolidine-2,4-dicarboxylate (2RS,4SR,5RS)-3-{-3-[2-(2-tert-butoxycarbonyl-5-(2-fluorophenyl)-4-phenylsulphonyl-1-pyrrolidinyl)-2-oxoethyl]ureido}benzoic acid, (2RS,4SR,5RS)-3-{3-[2-(2-(3,3-dimethylpiperidinocarbonyl)-5-(2-fluorophenyl)-4-phenylsulphonyl-1-pyrrolidinyl)-2-oxoethyl]ureido}benzoic acid, 2-tert-butyl hydrogen (2RS,4SR,5SR)-1-{2-[3-(3-(carboxymethyl)phenyl)ureido]acetyl}-5-2-fluorophenyl)pyrrolidine-2,4-dicarboxylate, 2-tert-butyl hydrogen (2RS,4SR,5SR)-1-{2-[3-(3-(carboxymethyl)phenyl)ureido]acetyl}-5-(2-fluorophenyl)pyrrolidine-2,4-dicarboxylate acid, (2RS,4SR,5SR)-3-{3-[2-(2-tert-butoxycarbonyl-5-phenyl-4-(1-pyrrolidinylcarbonyl)-1-pyrrolidinyl)-2-oxoethyl]ureido}benzoic acid, (2RS,4SR,5SR)-3-{3-[2-(2-tert-butoxycarbonyl-4-dimethylcarbamoyl-5-phenyl-1-pyrrolidinyl)-2-oxoethyl]ureido}benzoic acid, (2RS-4SR,5SR)-3-{3-[2-(4-benzoyl-2-tert-butoxycarbonyl-5-(2-fluorophenyl)-1-pyrrolidinyl)-2-oxoethyl]ureido}benzoic acid, 2-{3-[3-(2-((2R*,4S*,5R*)-2-tert-butoxycarbonyl-5-(2-fluorophenyl)-4-phenylsulphonyl-1-pyrrolidinyl)-2-oxoethyl)ureido]phenyl}propionic acid, (S)-2-{3-[3-(2-((2R*,4S*,5R*)-2-tert-butoxycarbonyl-5-(2-fluorophenyl)-4-phenylsulphonyl-1-pyrrolidinyl)-2-oxoethyl)ureido]phenyl}-2-methoxyacetic acid, (2RS,4SR,5SR)-3-{3-[2-(2-tert-butoxycarbonyl-5-(2-fluorophenyl)-4-morpholinocarbonyl-1-pyrrolidinyl)-2-oxoethyl]ureido}benzoic acid, (2RS,4SR,5SR)-3-{3-[2-(2-tert-butoxycarbonyl-4-diethylaminocarbonyl-5-(2-fluorophenyl)-1-pyrrolidinyl)-2-oxoethyl]ureido}benzoic acid, (2RS,4SR,5RS)-5-{3-[3-(2-(2-tert-butoxycarbonyl-5-(2-fluorophenyl)-4-phenylsulphonyl-1-pyrrolidinyl)-2-oxoethyl)ureido]phenyl}tetrazole, (2RS,4SR,5RS)-3-{3-[2-(5-(2-fluorophenyl)-2-isobutylcarbamoyl-4-phenylsulphonyl-1-pyrrolidinyl)-2-oxoethyl]ureido}phenylacetic acid, (2R*,4S*,5R*)-(−)-3-{3-[2-(2-tert-butoxycarbonyl-5-(2-fluorophenyl)-4-phenylsulphonyl-1-pyrrolidinyl)-2-oxoethyl]ureido}benzoic acid, 2-tert-butyl hydrogen (2R*,4S*,5S*)-(+)-1-{2-[3-(3-(carboxymethyl)phenyl)ureido]acetyl}-5-(2-fluorophenyl)pyrrolidine-2,4-dicarboxylate.

The following examples illustrate the invention without limiting it.

EXAMPLE 1

A 0.1 g of 10% palladium-on-charcoal is added to a solution of 0.54 g of tert-butyl (2S,4R,5R)-1-{2-[3-(3-(benzyloxycarbonyl)phenyl)ureido]acetyl}-4-benzyl-5-phenylpyrrolidine-2-carboxylate in 25 cm³ of ethyl acetate. The suspension is stirred for eighteen hours at a temperature in the region of 20° C. under a hydrogen atmopshere (130 kPa). The catalyst is separated by filtration through Celite and the filtrate is concentrated to dryness under reduced pressure. The residue is chromatographed on silica [eluent: dichloromethane/methanol (99.5/0.5 by volume)]. the fractions containing the expected product are combined and concentrated under reduced pressure. The residue is resuspended in 10 cm³ of diisopropyl ether, filtered and dried under vacuum at a temperature in the region of 40° C. There is thus obtained 0.36 g of (2S,4R,5R)-3-{3-[2-(4-benzyl-2-tert-butoxycarbonyl-5-phenyl-1-pyrrolidinyl)-2-oxoethyl] ureido}benzoic acid ($R_f$=0.25; eluent: methylene chloride/methanol (90/10)).

B tert-Butyl (2S,4R,5R)-1-{2-[3-(3-(benzyloxycarbonyl) phenyl)ureido]acetyl}-4-benzyl-5-phenylpyrrolidine-2-carboxylate can be obtained in the following way: 0.2 g of N,N'-dicyclohexylcarbodiimide is added at a temperature in the region of 20° C. to a solution of 0.32 g of tert-butyl 4-benzyl-5-phenylpyrrolidine-2-carboxylate and 0.31 g of 2-{3-[3-(benzyloxycarbonyl)phenyl]ureido}acetic acid in 25 cm³ of acetonitrile. The reaction mixture is stirred for seventy-two hours at a temperature in the region of 20° C., filtered, rinsed with 5 cm³ of acetonitrile and concentrated under reduced pressure. There is thus obtained 0.54 g of tert-butyl (2S,4R,5R)-1-{2-[3-(3-(benzyloxycarbonyl) phenyl)ureido]acetyl}-4-benzyl-5-phenylpyrrolidine-2-carboxylate in the form of a foam used as is in the subsequent syntheses.

C tert-Butyl 4-benzyl-5-phenylpyrrolidine-2-carboxylate can be prepared in the following way: 0.15 g of platinum oxide is added to a solution of 1.65 g of tert-butyl 4-benzyl-5-phenyl-Δ5-pyrroline-2-carboxylate in 40 cm³ of ethanol. The suspension is stirred for eight hours at a temperature in the region of 20° C. under a hydrogen atmosphere (130 kPa). The catalyst is separated by filtration through Celite and the filtrate is concentrated to dryness under reduced pressure. The residue is chromatographed on silica [eluent: dichloromethane/methanol (100/0 then 99.5/0.5 by volume) ]. The fractions containing the expected product are combined and concentrated under reduced pressure. There is thus obtained 0.32 g of tert-butyl 4-benzyl-5-phenylpyrrolidine-2-carboxylate in the form of a lacquer used as is in the subsequent syntheses.

D tert-Butyl 4-benzyl-5-phenyl-Δ5-pyrroline-2-carboxylate can be prepared in the following way: 2.15 cm³ of trifluoroacetic acid are added, at a temperature in the region of 20° C., to a solution of 2.4 g of tert-butyl 4-benzyl-1-tert-butoxycarbonyl-5-hydroxy-5-phenylpyrrolidine-2-carboxylate in 35 cm³ of dichloromethane. The reaction mixture is stirred for twenty hours at a temperature in the region of 20° C. and then 100 cm³ of dichloromethane are added. The organic phase is washed with two times 80 cm³ of a saturated aqueous sodium hydrogencarbonate solution and then 100 cm³ of distilled water, dried over magnesium sulphate and concentrated under reduced pressure. The residue is purified by chromtography on silica (eluent: dichloromethane). The fractions containing the expected product are combined and concentrated under reduced pressure. There are thus obtained 2 g of tert-butyl 4-benzyl-5-phenyl-Δ⁵-pyrroline-2-carboxylate in the form of an oil used as is in the subsequent syntheses.

E tert-Butyl 4-benzyl-1-tert-butoxycarbonyl-5-hydroxy-5-phenylpyrrolidine-2-carboxylate can be prepared in the following way: a solution of 2.85 cm³ of bromobenzene in 60 cm³ of tetrahydrofuran is added over forty minutes, at a temperature between 20° and 30° C., to a suspension of 0.8 g of magnesium in 20 cm³ of tetrahydrofuran. The reaction mixture is then stirred at a temperature in the region of 24° C. for twenty minutes and then a solution of 8.4 g of tert-butyl 4-benzyl-1-tert-butoxycarbonyl-5-oxopyrrolidine-2-carboxylate in 80 cm³ of tetrahydrofuran maintained at a temperature in the region of 5° C. is added over twenty minutes. The reaction mixture is than stirred for twenty hours at a temperature in the region of 20° C. The reaction mixture is then poured into 150 cm³ of a 10% aqueous ammonium chloride solution. The aqueous phase is extracted with three times 100 cm³ of diethyl ether. The organic phases are combined and washed with 100 cm³ of water, dried over magnesium sulphate and concentrated under reduced pressure at a temperature in the region of 50° C. The residue is purified by chromatography on silica (eluent: dichloromethane). The fractions containing the expected product are combined and concentrated under reduced pressure. There are thus obtained 2.5 g of tert-butyl 4-benzyl-1-tert-butoxycarbonyl-5-hydroxy-5-phenylpyrrolidine-2-carboxylate in the form of a foam used as is in the subsequent syntheses.

F tert-Butyl 4-benzyl-1-tert-butoxycarbonyl-5-oxopyrrolidine-2-carboxylate can be prepared in the following way: 18.8 cm³ of a 1.6M solution of butyllithium in hexane are added over fifteen minutes to a solution of 5.15 cm³ of diisopropylamine in 50 cm³ of tetrahydrofuran cooled to a temperature in the region of −75° C. The reaction mixture is stirred for thirty minutes at a temperature in the region of −78° C. and then a solution of 8.55 g of tert-butyl (S)-1-tert-butoxycarbonyl-5-oxopyrrolidine-2-carboxylate in 60 cm³ of tetrahydrofuran is added over twenty-five minutes. The reaction mixture is stirred at a temperature in the region of −75° C. for one hour and then a solution of 5.13 cm³ of benzyl bromide in 30 cm³ of tetrahydrofuran is added over ten minutes. The reaction mixture is stirred for a further four hours at a temperature in the region of −78° C. and then 200 cm³ of a saturated aqueous ammonium chloride solution and 100 cm³ of diethyl ether are added successively. The organic phase is separated by settling, washed with two times 100 cm³ of distilled water, dried over magnesium sulphate and concentrated under reduced pressure. The residue is resuspended in 70 cm³ of petroleum ether, filtered and dried under reduced pressure at 30° C. There are thus obtained 5.3 g of tert-butyl 4-benzyl-1-tert-butoxycarbonyl-5-oxopyrrolidine-2-carboxylate melting at 125° C. tert-Butyl (S)-1-tert-butoxycarbonyl-5-oxopyrrolidine-2-carboxylate can be obtained according to the method described by J. Ackermann and M. Matthes, Helv. Chim. Acta, 73, 122–132, (1990).

G 2-{3-[3-(Benzyloxycarbonyl)phenyl]ureido}acetic acid can be prepared in the following way: 13.4 g of benzyl 3-isocyanatobenzoate, in solution in 70 cm³ of 1,4-dioxane, are added over fifteen minutes to a solution of 3.97 g of glycine and 14.62 g of potassium carbonate in 90 cm³ of water. The reaction mixture is stirred for four hours at a temperature in the region of 20° C. and then acidified to a pH of 1 with a 4N aqueous hydrochloric acid solution. The insoluble product is separated by filtration, washed with three times 50 cm³ of water and air-dried. There are thus obtained 13 g of 2-{3-[3-(benzyloxycarbonyl)phenyl] ureido}acetic acid, used as is in the subsequent syntheses.

H Benzyl 3-isocyanatobenzoate can be prepared in the following way: a solution of benzyl 3-aminobenzoate in 150 cm³ of toluene, prepared by neutralizing 27 g of benzyl 3-aminobenzoate hydrochloride with 14.4 cm³ of triethylamine in 150 cm³ of toluene and filtering the suspension thus obtained, is added over fifteen minutes at a temperature in the region of −25° C. to a suspension of 2 g of charcoal in a mixture of 12.5 cm³ of trichloromethyl chloroformate and 50 cm³ of toluene. The reaction mixture is stirred at a temperature in the region of 25° C. for two hours and then heated at a temperature in the region of 110° C. for two hours. After cooling to a temperature in the region of 25° C., the reaction mixture is degassed by sparging with nitrogen, filtered through filter paper and concentrated under reduced pressure at a temperature in the region of 25° C. There are thus obtained 27 g of benzyl 3-isocyanatobenzoate in the form of an oil used as is in the subsequent syntheses. Benzyl 3-aminobenzoate can be prepared according to the method described by H. A. Shonle et al., J. Amer. Chem. Soc., 43, 361 (1921).

EXAMPLE 2

A 0.2 g of 5% palladium-on-charcoal is added to a solution of 1.25 g of 2-tert-butyl 4-methyl (2RS,4RS,5SR)-1-{2-[3-(3-(benzyloxycarbonyl)phenyl)ureido]acetyl}-5-phenylpyrrolidine-2,4-dicarboxylate in 100 cm³ of ethyl acetate. The suspension is stirred for four hours at a temperature in the region of 25° C. under a hydrogen atmosphere (130 kPa). The catalyst is separated by filtration through Celite, rinsed with two times 10 cm³ of methanol and the filtrate is concentrated to dryness under reduced pressure. The residue is crystallized from ethyl acetate, taken up in 25 cm³ of a decinormal aqueous hydrochloric acid solution, filtered, washed with two times 10 cm³ of water and dried under vacuum at a temperature in the region of 40° C. There is thus obtained 0.9 g of (2RS,4RS,5SR)-3-{3-[2-(2-tert-butoxycarbonyl-4-methoxycarbonyl-5-phenyl-1-pyrrolidinyl)-2-oxoethyl]ureido}benzoic acid, melting at 243° C.

B 2-tert-Butyl 4-methyl (2RS,4RS,5SR)-1-{2-[3-(3-(benzyloxycarbonyl)phenyl)ureido]acetyl}-5-phenylpyrrolidine-2,4-dicarboxylate can be prepared in the following way: 2.3 g of N,N'-dicyclohexylcarbodiimide are added at a temperature in the region of 20° C. to a solution of 3.06 g of 2-tert-butyl 4-methyl (2RS,4RS,5SR)-5-phenylpyrrolidine-2,4-dicarboxylate and 3.3 g of 2-{3-[3-(benzyloxycarbonyl)phenyl]ureido}acetic acid in 100 cm³ of acetonitrile. The reaction mixture is stirred for twenty hours at a temperature in the region of 20° C., concentrated under reduced pressure, taken up in 100 cm³ of ethyl acetate and filtered. The precipitate is rinsed with two times 25 cm³ of ethyl acetate and the filtrate is then concentrated under reduced pressure. The residue is purified by chromatography on silica [eluent: cyclohexane/ethyl acetate (70/30 by volume)]. The fractions containing the expected product are combined and concentrated under reduced pressure. There are thus obtained 2 g of 2-tert-butyl 4-methyl (2RS,4RS,5SR)-1-{2-[3-(3-(benzyloxycarbonyl)phenyl)ureido]acetyl}-5-phenylpyrrolidine-2,4-dicarboxylate in the form of an oil used as is in the subsequent syntheses.

C 2-tert-Butyl 4-methyl (2RS,4RS,5SR)-5-phenylpyrrolidine-2,4-dicarboxylate can be prepared in the following way: 2.8 cm³ of triethylamine are added dropwise at a temperature in the region of 20° C. to a suspension of 5 g of silver acetate in a solution of 1.8 cm³ of methyl acrylate and 4.5 g of tert-butyl benzylideneaminoacetate in 200 cm³ of acetonitrile. The reaction mixture is stirred for four hours at a temperature in the region of 20° C. and then poured into 200 cm³ of a saturated aqueous ammmonium chloride solution. The aqueous phase is filtered and extracted with three times 100 cm³ of ethyl acetate. The extracts are combined, washed with 100 cm³ of water, dried over magnesium sulphate, filtered and concentrated under reduced pressure. The residue is purified by chromatography on silica [eluent: cyclohexane/ethyl acetate (70/30 by volume)]. The fractions containing the expected product are combined and concentrated under reduced pressure. There are thus obtained 4.5 g of 2-tert-butyl 4-methyl (2RS,4RS, 5SR)-5-phenylpyrrolidine-2,4-dicarboxylate in the form of an oil used as is in the subsequent syntheses.

D tert-Butyl benzylideneaminoacetate can be prepared in the following way: 2.8 cm³ of triethylamine are added dropwise at a temperature in the region of 20° C. to a suspension of 3 g of 4 Å molecular sieve in a solution of 3.35 g of tert-butyl glycinate hydrochloride in 2.05 cm³ of benzaldehyde and 50 cm³ of dichloromethane. The reaction mixture is stirred for seventy-two hours at a temperature in the region of 20° C. and concentrated under reduced pressure. The residue is taken up in 50 cm³ of diethyl ether, filtered and the precipitate rinsed with two times 50 cm³ of diethyl ether. The filtrate is concentrated under reduced pressure. There are thus obtained 4.4 g of tert-butyl benzylideneaminoacetate in the form of an oil used as is in the subsequent syntheses.

EXAMPLE 3

0.21 g of potassium hydroxide, in solution in 15 cm³ of distilled water, is added to a solution of 1 g of (2RS,4RS, 5SR)-3-{3-[2-(2-tert-butoxycarbonyl-4-methoxycarbonyl-5-phenyl-1-pyrrolidinyl)-2-oxoethyl]ureido}benzoic acid in 50 cm³ of methanol. The reaction mixture is stirred for seventy-two hours at a temperature in the region of 20° C. and then concentrated under reduced pressure. The residue is diluted with 100 cm³ of water, washed with two times 100 cm³ of ethyl acetate, and acidified to a pH of 1 with a 4N aqueous hydrochloric acid solution. The precipitate which appears is separated by filtration, washed with two times 50 cm³ of distilled water and dried under reduced pressure at a temperature in the region of 40° C. The crude product obtained is purified by chromatography on silica [eluent: dichloromethane/methanol (90/10 by volume)]. The fractions containing the expected product are combined and concentrated to dryness under reduced pressure. There is obtained, after crystallization from a 0.1N aqueous hydrochloric acid solution, 0.65 g of 2-tert-butyl hydrogen (2RS, 4SR,5SR)-1-{2-[3-(3-carboxyphenyl)ureido]acetyl}-5-phenylpyrrolidine-2,4-dicarboxylate, melting at 193° C.

EXAMPLE 4

A The reaction is carried out in a way analogous to that described in Example 2B but from 1.7 g of tert-butyl (2RS,4RS,5SR)-4-dimethylcarbamoyl-5-phenylpyrrolidine-2-carboxylate, 1.15 g of 2-[3-(3-methylphenyl)ureido]acetic acid and 1.15 g of N,N'-dicyclohexylcarbodiimide in 50 cm³ of acetonitrile. After treatment, there are obtained 2.2 g of tert-butyl (2RS,4RS,5SR)-4-dimethylcarbamoyl-1-{2-[3-(3-methylphenyl)ureido]acetyl}-5-phenylpyrrolidine-2-carboxylate, melting at 199° C.

B tert-Butyl (2RS,4RS,5SR)-4-dimethylcarbamoyl-5-phenylpyrrolidine-2-carboxylate can be prepared as described in Example 2C, but from 4.4 g of tert-butyl benzylideneaminoacetate, 1.92 cm³ of N,N-dimethylacrylamide, 5 g of silver acetate and 2.8 cm³ of triethylamine in 200 cm³ of acetonitrile. After treatment, there are obtained 1.7 g of tert-butyl (2RS,4RS,5SR)-4-dimethylcarbamoyl-5-phenylpyrrolidine-2-carboxylate, melting at 97° C.

C 2-[3-(3-Methylphenyl)ureido]acetic acid can be prepared as described in Example 1G, but from 18.8 g of glycine and 21 g of sodium hydrogencarbonate in solution in 200 cm³ of water and from 32.3 cm³ of meta-tolyl isocyanate. After treatment, there are obtained 40.3 g of 2-[3-(3-methylphenyl)ureido]acetic acid used as is in the subsequent syntheses.

EXAMPLE 5

A The reaction is carried out in a way analogous to that described in Example 2B, but from 1.7 g of tert-butyl (2RS,4SR,5SR)-4-cyano-5-phenylpyrrolidine-2-carboxylate, 1.3 g of 2-[3-(3-methylphenyl)ureido]acetic acid and 1.3 g of N,N'-dicyclohexylcarbodiimide in 50 cm³ of acetonitrile. After treatment, there are obtained 1.5 g of tert-butyl (2RS,4SR,5SR)-4-cyano-1-{2-[2-(3-methylphenyl)ureido]acetyl}-5-phenylpyrrolidine-2-carboxylate in the form of an amorphous solid [R$_f$=0.17; eluent: cyclohexane/ethyl acetate (50/50)].

B tert-Butyl (2RS,4SR,5SR)-4-cyano-5-phenylpyrrolidine-2-carboxylate can be prepared as described in Example 2C, but from 4.4 g of tert-butyl benzylideneaminoacetate, 1.3 cm³ of acrylonitrile, 5 g of silver acetate and 2.8 cm³ of triethylamine in 200 cm³ of acetonitrile. After treatment, there are obtained 1.7 g of tert-butyl (2RS,4SR,5SR)-4-cyano-5-phenylpyrrolidine-2-carboxylate, melting at 112° C., and 1 g of tert-butyl (2RS,4RS,5SR)-4-cyano-5-phenylpyrrolidine-2-carboxylate, melting at 70° C.

EXAMPLE 6

The reaction is carried out in a way analogous to that described in Example 2B, but from 1 g of tert-butyl (2RS,4RS,5SR)-4-cyano-5-phenylpyrrolidine-2-carboxylate, 0.76 g of 2-[3-(3-methylphenyl)ureido]acetic acid and 0.76 g of N,N'-dicyclohexylcarbodiimide in 50 cm³ of acetonitrile. After treatment, there are obtained 1.2 g of tert-butyl (2RS,4RS,5SR)-4-cyano-1-{2-[3-(3-methylphenyl)ureido]acetyl}-5-phenylpyrrolidine-2-carboxylate, melting at 150° C.

EXAMPLE 7

The reaction is carried out in a way analogous to that described in Example 2B, but from 4.5 g of tert-butyl (2RS,4RS,5SR)-4-acetyl-5-phenylpyrrolidine-2-carboxylate, 3.2 g of 2-[3-(3-methylphenyl)ureido]acetic acid and 3.5 g of N,N'-dicyclohexylcarbodiimide in 50 cm³ of acetonitrile. After treatment, there is obtained 1 g of tert-butyl (2RS,4RS,5SR)-4-acetyl-1-{2-[3-(3-methylphenyl)ureido]acetyl}-5-phenylpyrrolidine-2-carboxylate, melting at 100° C.

B tert-Butyl (2RS,4RS,5SR)-4-acetyl-5-phenylpyrrolidine-2-carboxylate can be prepared as described in Example 2C, but from 4.4 g of tert-butyl benzylideneaminoacetate, 1.6 cm³ of methyl vinyl ketone, 5 g of silver acetate and 2.8 cm³ of triethylamine in 200 cm³ of acetonitrile. After treatment, there are obtained 4.6 g of tert-butyl (2RS,4RS,5SR)-4-acetyl-5-phenylpyrrolidine-2-carboxylate in the form of an oil used as is in the subsequent syntheses.

EXAMPLE 8

A The reaction is carried out in a way analogous to that described in Example 3, but from 1.6 g of 2-tert-butyl 4-methyl (2RS,4RS,5SR)-1-{2-[3-(3-methylphenyl)ureido]acetyl}-5-phenylpyrrolidine-2,4-dicarboxylate and 0.18 g of potassium hydroxide in 20 cm³ of distilled water and 60 cm³ of methanol. After treatment, there is obtained 0.7 g of 2-tert-butyl hydrogen (2RS,4SR,5SR)-1-{2-[3-(3-methylphenyl)ureido]acetyl}-5-phenylpyrrolidine-2,4-dicarboxylate, melting at 160° C.

B 2-tert-Butyl 4-methyl (2RS,4RS,5SR)-1-{2-[3-(3-methylphenyl)ureido]acetyl}-5-phenylpyrrolidine-2,4-dicarboxylate can be prepared as described in Example 2B, but from 1.22 g of 2-tert-butyl 4-methyl (2RS,4RS,5SR)-5-phenylpyrrolidine-2,4-dicarboxylate, 0.83 g of 2-[3-(3-methylphenyl)ureido]acetic acid and 0.83 g of N,N'-dicyclohexylcarbodiimide in 35 cm³ of acetonitrile. After treatment, there are obtained 1.6 g of 2-tert-butyl 4-methyl (2RS,4RS,5SR)-1-{2-[3-(3-methylphenyl)ureido]acetyl}-5-phenylpyrrolidine-2,4-dicarboxylate, melting at 130° C.

EXAMPLE 9

A The reaction is carried out in a way analogous to that described in Example 2A, but from 2.5 g of 4-benzyl 2-tert-butyl (2RS,4RS,5SR)-1-{2-[3-(3-(benzyloxycarbonyl)phenyl)ureido]acetyl}-4-methyl-5-phenylpyrrolidine-2,4-dicarboxylate and 0.25 g of 10% palladium-on-charcoal in 100 cm³ of ethanol. After treatment, there are obtained 1.4 g of 2-tert-butyl hydrogen (2RS,4RS,5SR)-1-{2-[3-(3-(carboxyphenyl)ureido]acetyl}-4-methyl-5-phenylpyrrolidine-2,4-dicarboxylate [R$_f$=0.15; eluent: methylene chloride/methanol (80/20)].

B 4-Benzyl 2-tert-butyl (2RS,4RS,5SR)-1-{2-[3-(3-(benzyloxycarbonyl)phenyl)ureido]acetyl}-4-methyl-5-phenylpyrrolidine-2,4-dicarboxylate can be prepared as described in Example 2B, but from 1.98 g of 4-benzyl 2-tert-butyl (2RS,4RS,5SR)-4-methyl-5-phenylpyrrolidine-2,4-dicarboxylate, 1.64 g of 2-{3-[3-(benzyloxycarbonyl)phenyl]ureido}acetic acid and 1.03 g of N,N'-dicyclohexylcarbodiimide in 50 cm³ of acetonitrile. After treatment, there are obtained 2.5 g of 4-benzyl 2-tert-butyl (2RS,4RS,5SR)-1-{2-[3-(3-(benzyloxycarbonyl)phenyl)ureido]acetyl}-4-methyl-5-phenylpyrrolidine-2,4-dicarboxylate in the form of an amorphous solid used as is in the subsequent syntheses.

C 4-Benzyl 2-tert-butyl (2RS,4RS,5SR)-4-methyl-5-phenylpyrrolidine-2,4-dicarboxylate can be prepared as in Example 2C, but from 4.4 g of tert-butyl benzylideneaminoacetate, 3.4 cm³ of benzyl methacrylate, 5 g of silver acetate and 2.8 cm³ of triethylamine in 200 cm³ of acetonitrile. After treatment, there are obtained 2.7 g of 4-benzyl 2-tert-butyl (2RS,4RS,5SR)-4-methyl-5-phenylpyrrolidine-2,4-dicarboxylate in the form of an oil used as is in the subsequent syntheses.

EXAMPLE 10

A solution of 3 g of tert-butyl (2RS,4RS,5SR)-4-acetyl-1-{2-[3-(3-methylphenyl)ureido]acetyl}-5-phenylpyrrolidine-2-carboxylate and 0.48 g of hydroxylammonium chloride in a mixture of 6 cm³ of pyridine, 12 cm³ of methanol and 6 cm³ of distilled water is heated at reflux for two hours. After cooling to a temperature in the region of 20° C., the mixture is concentrated under reduced pressure and diluted with a mixture of 25 cm³ of distilled water and 75 cm³ of ethyl acetate. After separating by settling, the aqueous phase is extracted with two times 50 cm³ of ethyl acetate. The organic phases are combined and washed with 50 cm³ of distilled water, dried over magnesium sulphate and concentrated under reduced pressure. The residue is crystallized from a 1/1 by volume diisopropyl ether/isopropyl acetate mixture. The crystals are filtered and washed with three times 2.5 cm³ of a diisopropyl ether/isopropyl acetate (1/1 by volume) mixture and air-dried to give 1 g of crude E isomer. The filtrates are combined and concentrated under reduced pressure to give 2.1 g of a mixture of Z and E isomers. The crude E isomer is recrystallized from 25 cm³ of isopropanol to give, after filtration and washing with three times 1 cm³ of diisopropyl ether, 0.5 g of tert-butyl (E)-(2RS,4RS,5SR)-4-[1-(hydroxyimino)ethyl]-1-{2-[3-(3-methylphenyl)-ureido]acetyl}-5-phenylpyrrolidine-2-carboxylate, melting at 215° C. The mixture of Z and E isomers is purified by chromatographing four times in succession on silica [eluents: diethyl ether, diethyl ether/diisopropyl ether (70/30 by volume), diethyl ether/diisopropyl ether (40/60 by volume), diethyl ether/diisopropyl ether (50/50 by volume)]. The fractions containing the expected product are combined and concentrated under reduced pressure. The residue is crystallized from 35 cm$^3$ of diethyl ether. There is thus obtained 0.4 g of 2-tert-butyl (Z)-(2RS,4RS,5SR)-4-[1-(hydroxyimino)ethyl]-1-{2-[3-(3-methylphenyl)ureido]acetyl}-5-phenylpyrrolidine-2-carboxylate, melting at 166° C.

EXAMPLE 11

A The reaction is carried out in a way analogous to that described in Example 2A, but from 3.3 g of tert-butyl (2RS,4SR,5RS)-1-{2-[3-(3-(benzyloxycarbonyl)phenyl)ureido]acetyl}-5-phenyl-4-(phenylsulphonyl)pyrrolidine-2-carboxylate and 0.35 g of 10% palladium-on-charcoal in 100 cm$^3$ of ethanol. After treatment, there are obtained 1.45 g of (2RS,4SR,5RS)-3-{3-[2-(2-tert-butoxycarbonyl-5-phenyl-4-phenylsulphonyl-1-pyrrolidinyl)-2-oxoethyl]ureido}benzoic acid, melting at 213° C.

B tert-Butyl (2RS,4SR,5RS)-1-{2-[3-(3-(benzyloxycarbonyl)phenyl)ureido]acetyl}-5-phenyl-4-(phenylsulphonyl)pyrrolidine-2-carboxylate can be prepared as described in Example 2B, but from 1.94 g of tert-butyl (2RS,4SR,5RS)-5-phenyl-4-(phenylsulphonyl)pyrrolidine-2-carboxylate, 1.64 g of 2-{3-[3-(benzyloxycarbonyl)phenyl]ureido}acetic acid and 1.03 g of N,N'-dicyclohexylcarbodiimide in 60 cm$^3$ of acetonitrile. After treatment, there are obtained 3.3 g of tert-butyl (2RS,4SR,5RS)-1-{2-[3-(3-(benzyloxycarbonyl)phenyl)ureido]acetyl}-5-phenyl-4-(phenylsulphonyl)pyrrolidine-2-carboxylate in the form of a solid used as is in the subsequent syntheses.

C tert-Butyl (2RS,4SR,5RS)-5-phenyl-4-(phenylsulphonyl)pyrrolidine-2-carboxylate can be prepared as described in Example 2C, but from 4.4 g of tert-butyl benzylideneaminoacetate, 3.4 g of phenyl vinyl sulphone, 5 g of silver acetate and 2.8 cm$^3$ of triethylamine in 200 cm$^3$ of acetonitrile. After treatment, there are obtained 3.35 g of tert-butyl (2RS,4SR,5RS)-5-phenyl-4-(phenylsulphonyl)pyrrolidine-2-carboxylate, melting at 112° C., and 1.1 g of tert-butyl (2RS,4RS,4RS)-5-phenyl-4-(phenylsulphonyl)pyrrolidine-2-carboxylate, melting at 204° C.

EXAMPLE 12

A The reaction is carried out in a way analogous to that described in Example 2A, but from 1.9 g of tert-butyl (2RS,4RS,5RS)-1-{2-[3-(3-(benzyloxycarbonyl)phenyl)ureido]acetyl}-5-phenyl-4-(phenylsulphonyl)pyrrolidine-2-carboxylate and 0.2 g of 10% palladium-on-charcoal in 75 cm$^3$ of ethanol. After treatment, there are obtained 1.1 g of (2RS,4RS,5RS)-3-{3-[2-(2-tert-butoxycarbonyl-5-phenyl-4-phenylsulphonyl-1-pyrrolidinyl)-2-oxoethyl]ureido}benzoic acid [R$_f$=0.22; eluent: methylene chloride/methanol (80/20)].

B tert-Butyl (2RS,4RS,5RS)-1-{2-[3-(3-(benzyloxycarbonyl)phenyl)ureido]acetyl}-5-phenyl-4-(phenylsulphonyl)pyrrolidine-2-carboxylate can be prepared as described in Example 2B, but from 1.1 g of tert-butyl (2RS,4RS,5RS)-5-phenyl-4-(phenylsulphonyl)pyrrolidine-2-carboxylate, 0.95 g of 2-{3-[3-(benzyloxycarbonyl)phenyl]ureido}acetic acid and 0.6 g of N,N'-dicyclohexylcarbodiimide in 40 cm$^3$ of acetonitrile.

After treatment, there are obtained 1.9 g of tert-butyl (2RS,4RS,5RS)-1-{2-[3-(3-(benzyloxycarbonyl)phenyl)ureido]acetyl}-5-phenyl-4-(phenylsulphonyl)pyrrolidine-2-carboxylate, melting at 212° C.

EXAMPLE 13

A The reaction is carried out in a way analogous to that described in Example 2A, but from 1.62 g of tert-butyl (2RS,4SR,5RS)-4-benzyloxycarbonylamino-1-{2-[3-(3-(benzyloxycarbonyl)phenyl)ureido]acetyl}-5-phenylpyrrolidine-2-carboxylate and 0.16 g of 10% palladium-on-charcoal in 100 cm$^3$ of ethanol. After treatment, there is obtained 0.43 g of tert-butyl (2RS,4SR,5RS)-4-amino-1-{2-[3-(3-carboxyphenyl)ureido]acetyl}pyrrolidine-2-carboxylate in the form of an amorphous solid [R$_f$=0.24; eluent: methylene chloride/methanol (80/20)].

B tert-Butyl (2RS,4SR,5RS)-4-benzyloxycarbonylamino-1-{2-[3-(3-(benzyloxycarbonyl)phenyl)ureido]acetyl}-5-phenylpyrrolidine-2-carboxylate can be obtained in the following way: a solution of 2.1 g of tert-butyl (2RS,4SR,5RS)-1-(2-aminoacetyl)-4-benzyloxycarbonylamino-5-phenylpyrrolidine-2-carboxylate in 20 cm$^3$ of 1,2-dichloroethane is added to a solution of 0.83 g of N,N'-carbonyldiimidazole in 30 cm$^3$ of 1,2-dichloroethane. The mixture is stirred for two hours at a temperature in the region of 20° C. and then 1.05 g of benzyl 3-aminobenzoate are added. The mixture is heated at a temperature in the region of 80° C. for fourteen hours. After cooling to a temperature in the region of 20° C., the reaction mixture is diluted with 75 cm$^3$ of dichloromethane. The organic phase is washed with two times 100 cm$^3$ of distilled water, then two times 100 cm$^3$ of a decinormal aqueous hydrochloric acid solution, two times 100 cm$^3$ of distilled water and two times 100 cm$^3$ of a saturated aqueous sodium chloride solution, dried over magnesium sulphate and concentrated under reduced pressure. The residue is purified by chromatography on silica (eluent: methylene chloride). The fractions containing the expected product are combined and concentrated under reduced pressure. There are thus obtained 1.6 g of tert-butyl (2RS,4SR,5RS)-4-benzyloxycarbonylamino-1-{2-[3-(3-(benzyloxycarbonyl)phenyl)ureido]acetyl}-5-phenylpyrrolidine-2-carboxylate in the form of a foam used as is in the subsequent syntheses.

C tert-Butyl (2RS,4SR,5RS)-1-(2-aminoacetyl)-4-benzyloxycarbonylamino-5-phenylpyrrolidine-2-carboxylate can be obtained in the following way: 1.22 cm$^3$ of iodotrimethylsilane are added to a solution of 4.75 g of tert-butyl (2RS,4SR,5RS)-4-benzyloxycarbonylamino-1-[2-(tert-butoxycarbonylamino)acetyl]-5-phenylpyrrolidine-2-carboxylate in 125 cm$^3$ of chloroform. The reaction mixture is stirred for twenty hours at a temperature in the region of 20° C. and is then brought to a pH in the region of 7 by addition of a saturated aqueous sodium hydrogencarbonate solution. The organic phase is separated by settling, washed with two times 100 cm$^3$ of saturated aqueous sodium chloride solution, dried over magnesium sulphate and concentrated under reduced pressure. The residue purified by chromatography on silica [eluent: dichloromethane/methanol (99/1 by volume)]. The fractions containing the expected product are combined and concentrated under reduced pressure. There are thus obtained 2.1 g of tert-butyl (2RS,4SR,5RS)-1-(2-aminoacetyl)-4-benzyloxycarbonylamino-5-phenylpyrrolidine2-carboxylate in the form of a foam used as is in the subsequent syntheses.

D tert-Butyl (2RS,4SR,5RS)-4-benzyloxycarbonylamino-1-[2-(tert-butoxycarbonylamino)

acetyl]-5-phenylpyrrolidine-2-carboxylate can be obtained in the following way: a solution of 5.38 g of 2-tert-butyl hydrogen (2RS,4SR,5SR)-1-[2-(tert-butoxycarbonylamino) acetyl]-5-phenylpyrrolidine-2,4-dicarboxylate, 3.1 cm³ of diphenylphosphoryl azide and 1.86 cm³ of triethylamine in 80 cm³ of toluene is stirred for thirty minutes at a temperature in the region of 20° C. and then for thirty minutes at a temperature in the region of 80° C. A solution of 1.49 cm³ of benzyl alcohol in 40 cm³ of toluene containing 57 mg of sodium hydride is then added dropwise. The reaction mixture is stirred for twenty hours at a temperature in the region of 50° C. After returning to a temperature in the region of 20° C., the organic phase is washed with three times 75 cm³ of distilled water and then 50 cm³ of a saturated aqueous sodium chloride solution, dried over magnesium sulphate and concentrated under reduced pressure. The residue is purified by chromatography on silica [eluent: dichloromethane and then dichloromethane/methanol (99/1 by volume)]. The fractions containing the expected product are combined and concentrated under reduced pressure. There are thus obtained 3.75 g of tert-butyl (2RS,4SR,5RS)-4-benzyloxycarbonylamino-1-[2-(tert-butoxycarbonylamino) acetyl]-5-phenylpyrrolidine-2-carboxylate in the form of a foam used as is in the subsequent syntheses.

E 2-tert-Butyl hydrogen (2RS,4SR,5SR)-1-[2-(tert-butoxycarbonylamino)acetyl]-5-phenylpyrrolidine-2,4-dicarboxylate can be prepared in the following way: a solution of 34.7 g of 2-tert-butyl 4-methyl (2RS,4RS,5SR)-1-[2-(tert-butoxycarbonylamino)acetyl]-5-phenylpyrrolidine-2,4-dicarboxylate and 4.81 g of potassium hydroxide in a mixture of 600 cm³ of methanol and 20 cm³ of water is stirred for twenty hours at a temperature in the region of 20° C. The mixture is then concentrated under reduced pressure and diluted with water. The aqueous phase is washed with three times 200 cm³ of diethyl ether, then brought to a pH in the region of 1 with a 4N aqueous hydrochloric acid solution and extracted with three times 200 cm³ of dichloromethane. The combined organic phase is washed with two times 200 cm³ of a saturated aqueous sodium chloride solution, dried over magnesium sulphate and concentrated under reduced pressure. The residue is taken up in diisopropyl ether, filtered and dried under reduced pressure. There are thus obtained 27.5 g of 2-tert-butyl hydrogen (2RS,4SR,5SR)-1-[2-(tert-butoxycarbonylamino)acetyl]-5-phenylpyrrolidine-2,4-dicarboxylate, melting at 105° C.

F 2-tert-Butyl 4-methyl (2RS,4RS,5SR)-1-[2-(tertbutoxycarbonylamino)acetyl]-5-phenylpyrrolidine-2,4-dicarboxylate can be prepared in the following ways 11.5 g of N,N'-dicyclohexylcarbodiimide are added to a solution of 17 g of 2-tert-butyl 4-methyl (2RS,4RS,5SR)-5-phenylpyrrolidine-2,4-dicarboxylate and 9.75 g of 2-(tert-butoxycarbonylamino)acetic acid in 200 cm³ of acetonitrile. The reaction mixture is stirred for twenty hours at a temperature in the region of 20° C. and then concentrated under reduced pressure. The residue is taken up in 100 cm³ of ethyl acetate and filtered. The solid is rinsed with two times 50 cm³ of ethyl acetate and the combined filtrates are concentrated under reduced pressure. The residue is crystallized from pentane and dried under reduced pressure at a temperature in the region of 40° C. There are thus obtained 22.5 g of 2-tert-butyl 4-methyl (2RS,4RS,5SR)-1-[2-(tert-butoxycarbonylamino)acetyl]-5-phenylpyrrolidine-2,4-dicarboxylate, melting at 137° C.

EXAMPLE 14

A The reaction is carried out in a way analogous to that described in Example 2A, but from 3.45 g of 4-benzyl 2-tert-butyl (2RS,4RS,5SR)-1-{2-[3-(3-(benzyloxycarbonyl)phenyl)ureido]acetyl}-5-phenylpyrrolidine-2,4-dicarboxylate and 0.5 g of 10% palladium-on-charcoal in 150 cm³ of ethanol. After treatment, there are obtained 2 g of 2-tert-butyl hydrogen (2RS,4RS,5SR)-1-{2-[3-(3-(carboxyphenyl)ureido] acetyl}pyrrolidinedicarboxylate, melting at 180° C.

B 4-Benzyl 2-tert-butyl (2RS,4RS,5SR)-1-{2-[3-(3-(benzyloxycarbonyl)phenyl)ureido]acetyl}-5-phenylpyrrolidine-2,4-dicarboxylate can be prepared as described in Example 2B, but from 3.05 g of 4-benzyl 2-tert-butyl (2RS,4RS,5SR)-5-phenylpyrrolidine-2,4-dicarboxylate, 2.6 g of 2-{3-[3-(benzyloxycarbonyl)phenyl) ureido}acetic acid and 1.65 g of N,N'-dicyclohexylcarbodiimide in 75 cm³ of acetonitrile. After treatment, there are obtained 1.35 g of 4-benzyl 2-tert-butyl (2RS,4RS,5SR)-1-{2-[3-(3-(benzyloxycarbonyl)phenyl) ureido]acetyl}-5-phenylpyrrolidine-2,4-dicarboxylate, melting at 110° C.

C 4-Benzyl 2-tert-butyl (2RS,4RS,5SR)-5-phenylpyrrolidine-2,4-dicarboxylate can be prepared as described in Example 2C, but from 17 g of tert-butyl benzylideneaminoacetate, 12.25 cm³ of benzyl acrylate, 20 g of silver acetate and 11.2 cm³ of triethylamine in 600 cm³ of acetonitrile. After treatment, there are obtained 18.9 g of 4-benzyl 2-tert-butyl (2RS,4RS,5SR)-5-phenylpyrrolidine-2,4-dicarboxylate, melting at 70° C.

EXAMPLE 15

A The reaction is carried out in a way analogous to that described in Example 3, but from 2.1 g of 2-tert-butyl 4-methyl (2RS,4RS,5SR)-1-{2-[3-(4-chlorophenyl)ureido] acetyl}-5-phenylpyrrolidine-2,4-dicarboxylate in a mixture of 4 cm³ of a normal aqueous potassium hydroxide solution, 20 cm³ of distilled water and 60 cm³ of methanol. After treatment, there are obtained 1.4 g of 2-tert-butyl hydrogen (2RS,4SR,5SR)-1-{2-[3-(4-chlorophenyl)ureido]acetyl}-5-phenylpyrrolidine-2,4-dicarboxylate, melting at 248° C.

B 2-tert-Butyl 4-methyl (2RS,4RS,5SR)-1-{2-[3-(4-chlorophenyl)ureido]acetyl}-5-phenylpyrrolidine-2,4-dicarboxylate can be prepared as described in Example 2B, but from 1.53 g of 2-tert-butyl 4-methyl (2RS,4RS,5SR)-5-phenyl pyrrolidine-2,4-dicarboxylate, 1.14 g of 2-[3-(4-chlorophenyl)ureido]acetic acid and 1.03 g of N,N'-dicyclohexylcarbodiimide in 45 cm³ of acetonitrile. After treatment, there are obtained 2.3 g of 2-tert-butyl 4-methyl (2RS,4RS,5SR)-1-{2-[3-(4-chlorophenyl)ureido]acetyl}-5-phenylpyrrolidine-2,4-dicarboxylate, melting at 125° C.

C 2-[3-(4-Chlorophenyl)ureido]acetic acid can be prepared as described in Example 1G, but from 2.25 g of glycine and 2.5 g of sodium bicarbonate in solution in 35 cm³ of water and from 4.6 g of para-chlorophenyl isocyanate. After treatment, there are obtained 5 g of 2-[3-(4-chlorophenyl)ureido]acetic acid, melting at 218° C.

EXAMPLE 16

A The reaction is carried out in a way analogous to that described in Example 3, but from 1.8 g of 2-tert-butyl 4-methyl (2RS,4RS,5SR)-1-{2-[3-(3-((RS)-1-hydroxyethyl)phenol)ureido]acetyl}-5-phenylpyrrolidine-2, 4-dicarboxylate (mixture of forms A and B) and 0.19 g of potassium hydroxide in a mixture of 15 cm³ of distilled water and 50 cm³ of methanol. After treatment, there are obtained 0.8 g of 2-tert-butyl hydrogen (2RS,4SR,5SR)-1-{2-[3-(3-(1-hydroxyethyl)phenyl)ureido]acetyl}-5-phenylpyrrolidine-2,4-dicarboxylate (mixture of forms A and B) [$R_f$=0.05; eluent: methylene chloride/methanol (90/10)].

27

B 2-tert-Butyl 4-methyl (2RS,4RS,5SR)-1-{2-[3-(3-((RS)-1-hydroxyethyl)phenyl)ureido]acetyl}-5-phenylpyrrolidine-2,4-dicarboxylate (mixture of forms A and B) can be prepared in the following way: a solution of 2.2 g of 2-tert-butyl 4-methyl (2RS,4RS,5SR)-1-(2-aminoacetyl)-5-phenylpyrrolidine-2,4-carboxylate in 25 cm³ of 1,2-dichloroethane is added to a solution of 1.1 g of N,N'-carbonyldiimidazole in 50 cm³ of 1,2-dichloroethane. The mixture is stirred for one hour at a temperature in the region of 20° C. and then 0.92 g of (RS)-3-(1-hydroxyethyl) aniline is added. The mixture is heated at a temperature in the region of 80° C. for four hours. After cooling to a temperature in the region of 20° C., the reaction mixture is diluted with 100 cm³ of dichloromethane. The organic phase is washed with two times 50 cm³ of distilled water and then two times 50 cm³ of a decinormal aqueous hydrochloric acid solution, dried over magnesium sulphate and concentrated under reduced pressure. The residue is purified by chromatography on silica [eluent: ethyl acetate/cyclohexane (70/30 by volume)]. The fractions containing the expected product are combined and concentrated under reduced pressure. There are thus obtained 1.9 g of 2-tert-butyl 4-methyl (2RS,4RS,5SR)-1-{2-[3-(3-((RS)-1-hydroxyethyl)phenyl)ureido]acetyl}-5-phenylpyrrolidine-2,4-dicarboxylate (mixture of forms A and B) in the form of an amorphous solid used as is in the subsequent syntheses.

C 2-tert-Butyl 4-methyl (2RS,4RS,5SR)-1-(2-aminoacetyl)-5-phenylpyrrolidine-2,4-dicarboxylate can be prepared in the following way: 2.85 cm³ of iodotrimethylsilane are added to a solution of 9.25 g of 2-tert-butyl 4-methyl (2RS,4RS,5SR)-1-[2-(tert-butoxycarbonylamino)acetyl]-5-phenylpyrrolidine-2,4-dicarboxylate in 200 cm³ of chloroform. The reaction mixture is stirred for two hours at a temperature in the region of 20° C. and is then brought to a pH in the region of 7 by addition of a saturated aqueous sodium hydrogencarbonate solution. The organic phase is separated by settling, washed with a saturated aqueous sodium chloride solution, dried over magnesium sulphate and concentrated under reduced pressure. There are thus obtained 5 g of 2-tert-butyl 4-methyl (2RS,4RS,5SR)-1-(2-aminoacetyl)-5-phenylpyrrolidine-2,4-dicarboxylate in the form of an oil used as is in the subsequent syntheses.

D 2-tert-Butyl 4-methyl (2RS,4RS,5SR)-1-[2-(tert-butoxycarbonylamino)acetyl]-5-phenylpyrrolidine-2,4-dicarboxylate can be prepared in the following way: 11.5 g of N,N'-cyclohexylcarbodiimide are added to a solution of 17 g of 2-tert-butyl 4-methyl (2RS,4RS,5SR)-5-phenylpyrrolidine-2,4-dicarboxylate and 9.75 g of 2-(tert-butoxycarbonylamino)acetic acid in 200 cm³ of acetonitrile. The reaction mixture is stirred for twenty hours at a temperature in the region of 20° C. and then concentrated under reduced pressure. The residue is taken up in 100 cm³ of ethyl acetate and filtered. The solid is rinsed with two times 50 cm³ of ethyl acetate and the combined filtrates are concentrated under reduced pressure. The residue is crystallized from pentane and dried under reduced pressure at a temperature in the region of 40° C. There are thus obtained 22.5 g of 2-tert-butyl 4-methyl (2RS,4RS,5SR)-1-[2-(tert-butoxycarbonylamino)acetyl]-5-phenylpyrrolidine-2,4-dicarboxylate, melting at 137° C.

EXAMPLE 17

A The reaction is carried out in a way analogous to that described in Example 3, but from 2.6 g of 2-tert-butyl 4-methyl (2RS,4RS,5SR)-1-{2-[3-(3-(methoxycarbonylmethylthio)phenyl)ureido]acetyl}-5-phenylpyrrolidine-2,4-dicarboxylate and 0.5 g of potassium hydroxide in a mixture of 15 cm³ of distilled water and 50 cm³ of methanol. After treatment, there are obtained 1.8 g of 2-tert-butyl hydrogen (2RS,4RS,5SR)-1-{2-[3-(3-(carboxymethylthio)phenyl)ureido]acetyl}-5-phenylpyrrolidine-2,4-dicarboxylate [$R_f$=0.1; eluent: methylene chloride/methanol (90/10)].

B 2-tert-Butyl 4-methyl (2RS,4RS,5SR)-1-{2-[3-(3-(methoxycarbonylmethylthio)phenyl)ureido]acetyl}-5-phenylpyrrolidine-2,4-dicarboxylate can be obtained in the following way: a solution of 1.48 g of methyl 2-[3-(isocyanato)phenylthio]acetate in 10 cm³ of tetrahydrofuran is added to a solution of 2.4 g of 2-tert-butyl 4-methyl (2RS,4RS,5SR)-1-(2-aminoacetyl)-5-phenylpyrrolidine-2,4-dicarboxylate in 50 cm³ of tetrahydrofuran. The mixture is stirred for twenty hours at a temperature in the region of 20° C. and then concentrated under reduced pressure. The residue is purified by chromatography on silica [eluent: ethyl acetate/cyclohexane (50/50 by volume)]. The fractions containing the expected product are combined and concentrated under reduced pressure. There are thus obtained 2.6 g of 2-tert-butyl 4-methyl (2RS,4RS,5SR)-1-{2-[3-(3-(methoxycarbonylmethylthio)phenyl)ureido]acetyl}-5-phenylpyrrolidine-2,4-dicarboxylate in the form of an amorphous solid used as is in the subsequent syntheses.

C Methyl 2-[3-(isocyanato)phenylthio]acetate can be prepared in the following way: a solution of 21.7 g of methyl 2-(3-aminophenylthio)acetate in 300 cm³ of toluene is added, at a temperature in the region of −20° C., to a suspension of 2.2 g of 3S charcoal in 300 cm³ of toluene and 13.3 cm³ of trichloromethyl chloroformate. The reaction mixture is stirred at a temperature in the region of −20° C. for two hours, then at a temperature in the region of 20° C. for two hours and finally at reflux for two hours. After cooling to a temperature in the region of 20° C., the mixture is degassed by sparging with nitrogen, filtered through supercel and concentrated under reduced pressure. There are thus obtained 25 g of methyl 2-(3-isocyanatophenylthio)acetate in the form of an oil used as is in the subsequent syntheses.

D Methyl 2-(3-aminophenylthio)acetate can be prepared in the following way: 20 cm³ of methyl bromoacetate are added to a solution of 25 g of 3-aminothiophenol in 400 cm³ of ethanol. The mixture is stirred for one hour and a half at a temperature in the region of 20° C. and then concentrated under reduced pressure. The residue is diluted with 300 cm³ of ethyl acetate; the organic solution is washed with 300 cm³ of a saturated aqueous sodium hydrogencarbonate solution and then 300 cm³ of distilled water, dried over magnesium sulphate and concentrated under reduced pressure. The residue is purified by chromatography on silica [eluent: ethyl acetate/cyclohexane (25/75 by volume)]. The fractions containing the expected product are combined and concentrated under reduced pressure. There are thus obtained 21.8 g of methyl 2-(3-aminophenylthio)acetate in the form of an oil used as is in the subsequent syntheses.

EXAMPLE 18

A The reaction is carried out in a way analogous to that described in Example 3, but from 1.5 g of 2-tert-butyl 4-methyl (2RS,4RS,5SR)-1-{2-[3-(3-(methylthio)phenyl)ureido]acetyl}-5-phenylpyrrolidine-2,4-dicarboxylate in a mixture of 2.8 cm³ of a normal aqueous potassium hydroxide solution, 15 cm³ of distilled water and 60 cm³ of methanol. After treatment, there are obtained 1.05 g of 2-tert-butyl hydrogen (2RS,4SR,5SR)-1-{2-[3-(3-(methylthio)phenyl)ureido]-acetyl}-5-phenylpyrrolidine-2,4-dicarboxylate, melting at 130° C.

B 2-tert-Butyl 4-methyl (2RS,4RS,5SR)-1-{2-[3-(3-(methylthio)phenyl)ureido]acetyl}-5-phenylpyrrolidine-2,4-dicarboxylate can be prepared as described in Example 16B, but from 2.7 g of 2-tert-butyl 4-methyl (2RS,4RS,5SR)-1-(2-aminoacetyl)-5-phenylpyrrolidine-2,4-dicarboxylate, 1.3 g of N,N'-carbonyldiimidazole and 0.9 cm³ of 3-(methylthio)aniline in 90 cm³ of 1,2-dichloroethane. After treatment, there are obtained 1.6 g of 2-tert-butyl 4-methyl (2RS,4RS,5SR)-1-{2-[3-(3-(methylthio)phenyl)ureido]acetyl}-5-phenylpyrrolidine-2,4-dicarboxylate in the form of an amorphous solid used as is in the subsequent syntheses.

EXAMPLE 19

A The reaction is carried out in a way analogous to that described in Example 2A, but from 5.8 g of tert-butyl (2RS,4SR,5RS)-1-{2-[3-(3-(benzyloxycarbonyl)phenyl)ureido]acetyl}-5-(2-fluorophenyl)-4-(phenylsulphonyl)pyrrolidine-2-carboxylate and 0.6 g of 10% palladium-on-charcoal in 200 cm³ of ethanol. After treatment, there are obtained 2.85 g of (2RS,4SR,5RS)-3-{3-[2-(2-tert-butoxycarbonyl-5-(2-fluorophenyl)-4-phenylsulphonyl-1-pyrrolidinyl)2-oxoethyl]ureido}benzoic acid [$R_f$=0.25; eluent: methylene chloride/methanol (90/10)].

B tert-Butyl (2RS,4SR,5RS)-1-{2-[3-(3-(benzyloxycarbonyl)phenol)ureido]acetyl}-5-(2-fluorophenyl)-4-(phenylsulphonyl)pyrrolidine-2-carboxylate can be prepared as described in Example 2B, but from 6 g of tert-butyl (2RS,4SR,5RS)-5-(2-fluorophenyl)-4-(phenolsulphonyl)pyrrolidine-2-carboxylate, 4.5 g of 2-{3-[3-(benzyloxycarbonyl)phenyl]ureido}acetic acid and 2.8 g of N,N'-dicyclohexylcarbodiimide in 200 cm³ of acetonitrile. After treatment, there are obtained 5.8 g of tert-butyl (2RS,4SR,5RS)-1-{2-[3-(3-(benzyloxycarbonyl)phenyl)ureido]acetyl}-5-(2-fluorophenyl)-4-(phenylsulphonyl)pyrrolidine-2-carboxylate in the form of a foam used as is in the subsequent syntheses.

C tert-Butyl (2RS,4SR,5RS)-5-(2-fluorophenyl)-4-(phenylsulphonyl)pyrrolidine-2-carboxylate can be prepared as described in Example 2C, but from 9.5 g of tert-butyl (2-fluorobenzylideneamino)acetate, 6.7 g of phenyl vinyl sulphone, 10 g of silver acetate and 5.6 cm³ of triethylamine in 200 cm³ of acetonitrile. After treatment, there are obtained 6 g of tert-butyl (2RS,4SR,5RS)-5-(2-fluorophenyl)-4-(phenylsulphonyl)pyrrolidine-2-carboxylate, melting at 134° C., and 5.5 g of tert-butyl (2RS,4RS,5RS)-5-(2-fluorophenyl)-4-(phenylsulphonyl)pyrrolidine-2-carboxylate, melting at 200° C.

D tert-Butyl (2-fluorobenzylideneamino)acetate can be prepared as described in Example 2D, but from 4.2 cm³ of 2-fluorobenzaldehyde, 6.7 g of tert-butyl glycinate hydrochloride, 6 g of 4 Å sieve and 5.6 cm³ of triethylamine in 60 cm³ of dichloromethane. After treatment, there are obtained 9.5 g of tert-butyl (2-fluorobenzylideneamino)acetate in the form of an oil used as is in the subsequent syntheses.

EXAMPLE 20

A The reaction is carried out in a way analogous to that described in Example 3, but from 4 g of tert-butyl (2RS,4SR,5SR)-1-{2-[3-(3-(methoxycarbonyl)phenyl)ureido]acetyl}-5-phenyl-4-(phenylcarbamoyl)pyrrolidine-2-carboxylate in a mixture of 6.7 cm³ of a normal aqueous potassium hydroxide solution, 30 cm³ of distilled water and 120 cm³ of methanol. After treatment, there is obtained 0.55 g of (2RS,4SR,5SR)-3-{3-[2-(2-tert-butoxycarbonyl-5-phenyl-4-phenylcarbamoyl-1-pyrrolidinyl)-2-oxoethyl]ureido}benzoic acid, melting at 160° C.

B tert-Butyl (2RS,4SR,5SR)-1-{2-[3-(3-(methoxycarbonyl)phenyl)ureido]acetyl}-5-phenyl-4-(phenylcarbamoyl)pyrrolidine-2-carboxylate can be prepared as described in Example 17B, but from 3.9 g of tert-butyl (2RS,4SR,5SR)-1-(2-aminoacetyl)-5-phenyl-4-(phenylcarbamoyl)pyrrolidine-2-carboxylate and 4.6 g of methyl 3-isocyanatobenzoate in 150 cm³ of tetrahydrofuran. After treatment, there are obtained 4 g of tert-butyl (2RS,4SR,5SR)-1-{2-[3-(3-(methoxycarbonyl)phenyl)ureido]acetyl}-5-phenyl-4-(phenylcarbamoyl)pyrrolidine-2-carboxylate in the form of a foam used as is in the subsequent syntheses.

C tert-Butyl (2RS,4SR,5SR)-1-(2-aminoacetyl)-5-phenyl-4-(phenylcarbamoyl)pyrrolidine-2-carboxylate can be prepared as described in Example 16C, but from 4.7 g of tert-butyl (2RS,4SR,5SR)-1-[2-(tert-butoxycarbonylamino)acetyl]-5-phenyl-4-(phenylcarbamoyl)pyrrolidine-2-carboxylate and 1.73 cm³ of iodotrimethylsilane in 150 cm³ of chloroform. After treatment, there are obtained 3.9 g of tert-butyl (2RS,4SR,5SR)-1-(2-aminoacetyl)-5-phenyl-4-(phenylcarbamoyl)pyrrolidine-2-carboxylate in the form of an oil used as is in the subsequent syntheses.

D tert-Butyl (2RS,4SR,5SR)-1-[2-(tert-butoxycarbonylamino)acetyl]-5-phenyl-4-(phenylcarbamoyl)pyrrolidine-2-carboxylate can be prepared in the following way: 2.06 g of N,N'-dicyclohexylcarbodiimide are added to a solution of 4.48 g of 2-tert-butyl hydrogen (2RS,4SR,5SR)-1-[2-(tert-butoxycarbonylamino)acetyl3-5-phenylpyrrolidine-2,4-dicarboxylate and 0.9 cm³ of aniline in 150 cm³ of acetonitrile. The reaction mixture is stirred for twenty hours at a temperature in the region of 20° C. and then filtered through Celite. The filtrate is concentrated under reduced pressure and the residue purified by chromatography on silica [eluent: dichloromethane/methanol (98.5/1.5 by volume)]. The fractions containing the expected product are combined and concentrated under reduced pressure. There are thus obtained 4.8 g of tert-butyl (2RS,4SR,5SR)-1-[2-(tert-butoxycarbonylamino)acetyl]-5-phenyl-4-(phenylcarbamoyl)pyrrolidine-2-carboxylate in the form of a foam used as is in the subsequent syntheses.

E 2-tert-Butyl hydrogen (2RS,4SR,5SR)-1-[2-(tert-butoxycarbonylamino)acetyl]-5-phenylpyrrolidine-2,4-dicarboxylate can be prepared in the following way: a solution of 34.7 g of 2-tert-butyl 4-methyl (2RS,4RS,5SR)-1-[2-(tert-butoxycarbonylamino)acetyl]-5-phenylpyrrolidine-2,4-dicarboxylate and 4.81 g of potassium hydroxide in a mixture of 600 cm³ of methanol and 20 cm³ of water is stirred for twenty hours at a temperature in the region of 20° C. The mixture is then concentrated under reduced pressure and diluted with water. The aqueous phase is washed with three times 200 cm³ of diethyl ether, then through to a pH in the region of 1 with a 4N aqueous hydrochloric acid solution and extracted with three times 200 cm³ of dichloromethane. The combined organic phases are washed with two times 200 cm³ of a saturated aqueous sodium chloride solution, dried over magnesium sulphate and concentrated under reduced pressure. The residue is taken up in diisopropyl ether, filtered and dried under reduced pressure. There are thus obtained 27.5 g of 2-tert-butyl hydrogen (2RS,4SR,5SR)-1-[2-(tert-butoxycarbonylamino)acetyl]-5-phenylpyrrolidine-2,4-dicarboxylate, melting at 105° C.

EXAMPLE 21

A The reaction is carried out in a way analogous to that described in Example 3, but from 3.6 g of tert-butyl (2RS, 4RS,5SR)-1-{2-[3-(3-(methoxycarbonyl)phenyl)ureido]acetyl}-4-methylphenylcarbamoyl-5-phenylpyrrolidine-2-carboxylate and 0.33 g of potassium hydroxide in a mixture of 20 cm³ of distilled water and 60 cm³ of methanol. After treatment, there are obtained 1.1 g of (2RS,4RS,5SR)-3-{3-[2-(2-tert-butoxycarbonyl-5-phenyl-4-methylphenylcarbamoyl-1-pyrrolidinyl)-2-oxoethyl]ureido}benzoic acid, melting at 238° C.

B tert-Butyl (2RS,4RS,5SR)-1-{2-[3-(3-(methoxycarbonyl)phenyl)ureido]acetyl}-4-methylphenylcarbamoyl-5-phenylpyrrolidine-2-carboxylate can be prepared as described in Example 17B, but from 2.8 g of tert-butyl (2RS,4RS,5SR)-1-(2-aminoacetyl)-4-methylphenylcarbamoyl-5-phenylpyrrolidine-2-carboxylate and 1.15 g of methyl 3-isocyanatobenzoate in 120 cm³ of tetrahydrofuran. After treatment, there are obtained 3.6 g of tert-butyl (2RS,4RS,5SR)-1-{2-[3-(3-(methoxycarbonyl)phenyl)ureido]acetyl}-4-methylphenylcarbamoyl-5-phenylpyrrolidine-2-carboxylate in the form of a foam used as is in the subsequent syntheses.

C tert-Butyl (2RS,4RS,5SR)-1-(2-aminoacetyl)-4-methylphenylcarbamoyl-5-phenylpyrrolidine-2-carboxylate can be prepared in Example 16C, but from 4.6 g of tert-butyl (2RS,4RS,5SR)-1-[2-(tert-butoxycarbonylamino)acetyl]-4-methylphenylcarbamoyl-5-phenylpyrrolidine-2-carboxylate and 1.2 cm³ of iodotrimethylsilane in 100 cm³ of chloroform. After treatment, there are obtained 2.8 g of tert-butyl (2RS,4RS,5SR)-1-(2-aminoacetyl)-4-methylphenylcarbamoyl-5-phenylpyrrolidine-2-carboxylate in the form of a foam used as is in the subsequent syntheses.

D tert-Butyl (2RS,4RS,5SR)-1-[2-(tert-butoxycarbonylamino)acetyl]-4-methylphenylcarbamoyl-5-phenylpyrrolidine-2-carboxylate can be prepared in the following way: 2.1 g of N,N'-dicyclohexylcarbodiimide and 0.1 g of b3-hydroxybenzotriazole are added to a solution of 4.5 g of 2-tert-butyl hydrogen (2RS,4SR,5SR)-1-[2-(tert-butoxycarbonylamino)acetyl]-5-phenylpyrrolidine-2,4-dicarboxylate and 1.1 cm³ of N-methylaniline in 60 cm³ of acetonitrile. The reaction mixture is stirred for twenty hours at a temperature in the region of 20° C. and then concentrated under reduced pressure. The residue is taken up in 50 cm³ of ethyl acetate, filtered through Celite and the precipitate rinsed with two times 50 cm³ of ethyl acetate. The filtrate is concentrated under reduced pressure. The residue is taken up in diisopropyl ether and filtered. The precipitate is washed with diisopropyl ether, dried under reduced pressure and purified by chromatography on silica [eluent: cyclohexane/ethyl acetate (50/50 by volume)]. The fractions containing the expected product are combined and concentrated under reduced pressure. There are thus obtained 2.8 g of tert-butyl (2RS,4RS,5SR)-1-[2-(tert-butoxycarbonylamino)acetyl]-4-methylphenylcarbamoyl-5-phenylpyrrolidine-2-carboxylate, melting at 182° C.

EXAMPLE 22

A The reaction is carried out in a way analogous to that described in Example 2A, but from 3.6 g of benzyl (2RS,4SR,5RS)-3-{3-[2-(2-(3,3-dimethylpiperidino)carbonyl-5-(2-fluorophenyl)-4-phenylsulphonyl-1-pyrrolidinyl)-2-oxoethyl]ureido}benzoate and 0.35 g of 10% palladium-on-charcoal in 200 cm³ of ethanol. After treatment, there are obtained 1.1 g of (2RS,4SR,5RS)-3-{3-[2-(2-(3,3-dimethylpiperidino)carbonyl-5-(2-fluorophenyl)-4-phenylsulphonyl-1-pyrrolidinyl)-2-oxoethyl]ureido}benzoic acid [$R_f$=0.21; eluent: methylene chloride/methanol (90/10)].

B Benzyl (2RS,4SR,5RS)-3-{3-[2-(2-(3,3-dimethylpiperidino)carbonyl-5-(2-fluorophenyl)-4-phenylsulphonyl-1-pyrrolidinyl)-2-oxoethyl]ureido}benzoate can be prepared as described in Example 2B, but from 2.6 g of (2RS,4SR,5RS)-2-(3,3-dimethylpiperidimo)carbonyl-5-(2-fluorophenyl)-4-phenylsulphonyl)pyrrolidine, 1.92 g of 2-{3-[3-(benzyloxycarbonyl)phenyl]ureido}acetic acid and 1.21 g of N,N'-dicyclohexylcarbodiimide in 50 cm³ of acetonitrile. After treatment, there are obtained 3.6 g of benzyl (2RS,4SR,5RS)-3-{3-[2-(2-(3,3-dimethylpiperidino)carbonyl-5-(2-fluorophenyl)-4-phenylsulphonyl-1-pyrrolidinyl)-2-oxoethyl]ureido}-benzoate in the form of a foam used as is in the subsequent syntheses.

C (2RS,4SR,5RS)-2-(3,3-Dimethylpiperidino)carbonyl-5-(2-fluorophenyl)-4-(phenylsulphonyl)pyrrolidine can be prepared as described in Example 2C, but from 2.5 g of 3,3-dimethyl-1-[2-{2-fluorobenzylideneamino)acetyl]piperidine, 1.48 g of phenyl vinyl sulphone, 2.2 g of silver acetate and 1.24 cm³ of triethylamine in 75 cm³ of acetonitrile. After treatment, there are obtained 2.3 g of (2RS,4SR,5RS)-2-(3,3-dimethylpiperidino)carbonyl-5-(2-fluorophenyl)-4-(phenylsulphonyl)pyrrolidine in the form of an oil used as is in the subsequent syntheses and 1 g of (2RS,4SR,5RS)-2-(3,3-dimethylpiperidino)carbonyl-5-(2-fluorophenyl)-4-(phenylsulphonyl)pyrrolidine, melting at 210° C.

D 1-[2-(2-Fluorobenzylideneamino)acetyl]-3,3-dimethylpiperidine can be prepared as described in Example 2D, but from 0.92 cm³ of 2-fluorobenzaldehyde, 1.5 g of 1-(2-aminoacetyl)-3,3-dimethylpiperidine and 2 g of 4 Å sieve in 50 cm³ of dichloromethane. After treatment, there are obtained 2.5 g of 1-[2-(2-fluorobenzylideneamino)acetyl]-3,3-dimethylpiperidine in the form of an oil used as is in the subsequent syntheses.

E 1-(2-Aminoacetyl)-3,3-dimethylpiperidine can be prepared in the following way: 11.9 cm³ of trifluoroacetic acid are added to a solution of 7 g of 1-[2-(tert-butoxycarbonylamino)acetyl]-3,3-dimethylpiperidine in 200 cm³ of dichloromethane. The reaction mixture is stirred for twenty hours at a temperature in the region of 20° C. and is then brought to a pH in the region of 7 by addition of a saturated aqueous sodium hydrogencarbonate solution. The organic phase is separated by settling and the saturated aqueous sodium chloride phase then extracted with two times 100 cm³ of dichloromethane. The organic phases are combined, dried over magnesium sulphate and concentrated under reduced pressure. The residue is purified by chromatography on silica [eluent: dichloromethane/methanol (90/10 by volume)]. The fractions containing the expected product are combined and concentrated under reduced pressure. There are thus obtained 1.5 g of 1-(2-aminoacetyl)-3,3-dimethylpiperidine in the form of an oil used as is in the subsequent syntheses.

F 1-[2-(tert-Butoxycarbonylamino)acetyl]-3,3-dimethylpiperidine can be prepared in the following way: a solution of 7 g of 2-(tert-butoxycarbonylamino)acetic acid and 7.15 g of N,N-carbonyldiimidazole in 100 cm³ of dichloromethane is stirred for two hours at a temperature in the region of 20° C. 5.4 cm³ of 3,3-dimethylpiperidine and 0.1 g of 4-dimethylaminopyridine are then added. The reaction mixture is stirred for seventy-two hours at a temperature in the region of 20° C. and then poured into 100 cm³ of distilled water. The organic phase is separated by settling, washed with two times 50 cm³ of a normal aqueous hydrochloric acid solution and 100 cm³ of distilled water and then dried over magnesium sulphate and concentrated under reduced pressure. There are thus obtained 7 g of 1-[2-(tert-butoxycarbonylamino)acetyl]-3,3-dimethylpiperidine in the form of an oil used as is in the subsequent syntheses.

EXAMPLE 23

A The reaction is carried out in a way analogous to that described in Example 2A, but from 1.6 g of benzyl (2RS, 4RS,5RS)-3-{3-[2-(2-(3,3-dimethylpiperidino)carbonyl-5-(2-fluorophenyl)-4-phenylsulphonyl-1-pyrrolidinyl)-2-oxoethyl]ureido}benzoate and 0.15 g of 10% palladium-on-charcoal in 100 cm³ of ethanol. After treatment, there is obtained 0.35 g of (2RS,4RS,5RS)-3-{3-[2-(2-(3,3-dimethylpiperidino)carbonyl-5-(2-fluorophenyl)-4-phenylsulphonyl-1-pyrrolidinyl)-2-oxoethyl}ureido}benzoic acid, melting at 258° C.

B Benzyl (2RS,4RS,5RS)-3-{3-[2-(2-(3,3-dimethylpiperidino)carbonyl-5-(2-fluorophenyl)-4-phenylsulphonyl-1-pyrrolidinyl)-2-oxoethyl]ureido}benzoate can be prepared as described in Example 2B, but from 1.12 g of (2RS,4RS,5RS)-2-(3,3-dimethylpiperidino)carbonyl-5-(2-fluorophenyl)-4-(phenylsulphonyl)pyrrolidine, 0.82 g of 2-{3-[3-(benzyloxycarbonyl)phenyl]ureido}acetic acid and 0.52 g of N,N'-dicyclohexylcarbodiimide in 50 cm³ of acetonitrile. After treatment, there are obtained 1.6 g of benzyl (2RS, 4RS,5RS)-3-{3-[2-(2-(3,3-dimethylpiperidino)carbonyl-5-(2-fluorophenyl)-4-phenylsulphonyl-1-pyrrolidinyl)-2-oxoethyl]ureido}benzoate in the form of a foam used as is in the subsequent syntheses.

EXAMPLE 24

A The reaction is carried out in a way analogous to that described in Example 3, but from 3.6 g of 2-tert-butyl 4-methyl (2RS,4RS,5SR)-5-(2-fluorophenyl)-1-{2-[3-(3-(methoxycarbonylmethyl)phenyl)ureido]acetyl}pyrrolidine-2,4-dicarboxylate and 0.75 g of potassium hydroxide in a mixture of 20 cm³ of distilled water and 60 cm³ of methanol. After treatment, there is obtained 1 g of 2-tert-butyl hydrogen (2RS,4SR,5SR)-1-{2-[3-(3-(carboxymethyl)phenyl)ureido]acetyl}-5-2-fluorophenyl) pyrrolidine-2,4-dicarboxylate [$R_f$=0.06; eluent: methylene chloride/methanol (80/20)].

B 2-tert-Butyl 4-methyl (2RS,4RS,5SR)-5-(2-fluorophenyl)-1-{2-[3-(3-(methoxycarbonylmethyl)phenyl) ureido]acetyl}pyrrolidine-2,4-dicarboxylate can be prepared as described in Example 2B, but from 2.3 g of 2-tert-butyl 4-methyl (2RS,4RS,5SR)-5-(2-fluorophenyl)pyrrolidine-2, 4-dicarboxylate, 1.89 g of 2-{3-[3-(methoxycarbonylmethyl)phenyl]ureido}acetic acid and 1.47 g of N,N'-dicyclohexylcarbodiimide in 50 cm³ of acetonitrile. After treatment, there are obtained 3.8 g of 2-tert-butyl 4-methyl (2RS,4RS,5SR)-5-(2-fluorophenyl)-1-{2-[3-(3-(methoxycarbonylmethyl)phenyl)ureido] acetyl}pyrrolidine-2,4-dicarboxylate in the form of a foam used as is in the subsequent syntheses.

C 2-tert-Butyl 4-methyl (2RS,4RS,5SR)-5-(2-fluorophenyl)pyrrolidine-2,4-dicarboxylate can be prepared as described in Example 2C, but from 24 g of tert-butyl (2-fluorobenzylideneamino)acetate, 9 cm³ of methyl acrylate, 25 g of silver acetate and 14 cm³ of triethylamine in 400 cm³ of acetonitrile. After treatment, there are obtained 29 g of 2-tert-butyl 4-methyl (2RS,4RS,5SR)-5-(2-fluorophenyl)pyrrolidine-2,4-dicarboxylate in the form of an oil used as is in the subsequent syntheses.

D 2-{3-[3-(Methoxycarbonylmethyl)phenyl] ureido}acetic acid can be prepared as described in Example 1G, but from 9.42 g of glycine and 34.69 g of potassium carbonate in 220 cm³ of water and from 24 g of methyl 3-isocyanatophenylacetate dissolved in 170 cm³ of 1,4-dioxane. After treatment and recrystallization from ethyl acetate, there are obtained 46.85 g of 2-{3-[3-(methoxycarbonylmethyl)phenyl]ureido}acetic acid, melting at 136° C.

E Methyl 3-isocyanatophenylacetate can be prepared in the following way: 8.25 g of methyl 3-aminophenylacetate, in solution in 100 cm³ of toluene, are added, at a temperature in the region of −20° C. and under argon, to a suspension of 1 g of charcoal and 6 cm³ of trichloromethyl chloroformate in 70 cm³ of toluene. The reaction mixture is stirred and maintained at −20° C. for fifteen minutes and then, after returning to a temperature in the region of 20° C., heated at reflux for two hours thirty minutes. The mixture is then degassed by sparging with argon for thirty minutes, filtered through Celite, rinsed with 50 cm³ of dichloromethane and concentrated under reduced pressure at a temperature in the region of 50° C. There are thus obtained 9.30 g of methyl 3-isocyanatophenylacetate in the form of an oil used as is in the subsequent syntheses. Methyl 3-aminophenylacetate can be prepared according to the method described by W. A. Jacobs et al., J. Amer. Chem. Soc., 34, 2420 (1917).

EXAMPLE 25

A The reaction is carried out in a way analogous to that described in Example 2A, but from 3.6 g of benzyl (2RS, 4SR,5RS)-3-{3-[2-(2-tert-butoxycarbonyl-5-(2-fluorophenyl)-4-phenylsulphonyl-1-pyrrolidinyl)-2-oxoethyl]ureido}phenylacetate 0.4 g of 10% palladium-on-charcoal in 200 cm³ of ethanol. After treatment, there are obtained 1.45 g of (2RS,4SR,5RS)-3-{3-[2-(2-tert-butoxycarbonyl-5-(2-fluorophenyl)-4-phenylsulphonyl-1-pyrrolidinyl)-2-oxoethyl]ureido}phenylacetic acid [$R_f$= 0.27; eluent: methylene chloride/methanol (80/20)].

B Benzyl (2RS,4SR,5RS)-3-{3-[2-(2-tert-butoxycarbonyl-5-(2-fluorophenyl)-4-phenylsulphonyl-1-pyrrolidinyl)-2-oxoethyl]ureido}phenylacetate can be prepared as described in Example 2B, but from 1.02 g of tert-butyl (2RS,4SR,5RS)-5-(2-fluorophenyl)-4-(phenylsulphonyl)pyrrolidine-2-carboxylate, 0.86 g of 2-{3-[3-(benzyloxycarbonylmethyl)phenyl]ureido}acetic acid and 0.52 g of N,N'-dicyclohexylcarbodiimide in 50 cm³ of acetonitrile. After treatment, there are obtained 1.8 g of benzyl (2RS,4SR,5RS)-3-{3-[2-(2-tert-butoxycarbonyl-5-(2-fluorophenyl)-4-phenylsulphonyl-1-pyrrolidinyl)-2-oxoethyl]ureido}phenylacetate in the form of a foam used as is in the subsequent syntheses.

C 2-{3-[3-(Benzyloxycarbonylmethyl)phenyl] ureido}acetic acid can be prepared as described in Example 1G, but from 2.5 g of glycine and 9.21 g of potassium carbonate in solution in 90 cm³ of water and from 8.96 g of benzyl 3-isocyanatophenylacetate in solution in 75 cm³ of 1,4-dioxane. After treatment, there are obtained 6.75 g of 2-{3-[3-(benzyloxycarbonylmethyl)phenyl]ureido}acetic acid used as is in the subsequent syntheses.

D Benzyl 3-isocyanatophenylacetate can be prepared as described in Example 17C, but from 8.55 g of benzyl 3-aminophenylacetate, 4.74 cm³ of trichloromethyl chloroformate and 0.9 g of vegetable charcoal in 130 cm³ of toluene. After treatment, there are obtained 8.96 g of benzyl 3-isocyanatophenylacetate in the form of an oil used as is in the subsequent syntheses.

E Benzyl 3-aminophenylacetate can be prepared in the following way: 197.96 g of ammonium chloride and 97.11 g of zinc powder are added to a solution of 20.25 g of benzyl 3-nitrophenylacetate in a mixture of 100 cm$^3$ of methanol and 1 l of distilled water. The suspension is heated at reflux for one hour and then cooled to a temperature in the region of 20° C. The reaction mixture is then filtered and the filtrate extracted with three times 500 cm$^3$ of diethyl ether. The extracts are combined and washed with 250 cm$^3$ of a saturated aqueous sodium chloride solution, dried over magnesium sulphate and concentrated under reduced pressure. The residue is purified by chromatography on silica [eluent: cyclohexane/ethyl acetate (85/15 then 70/30 by volume)]. The fractions containing the expected product are combined and concentrated under reduced pressure. There are thus obtained 8.58 g of benzyl 3-aminophenylacetate in the form of an oil used as is in the subsequent syntheses.

F Benzyl 3-nitrophenylacetate can be prepared in the following way: 0.1 cm$^3$ of N,N-dimethylformamide and then 16.6 cm$^3$ of oxalyl chloride are added to a solution of 13.6 g of 3-nitrophenylacetic acid in 130 cm$^3$ of 1,2-dichloroethane. The mixture is stirred for three hours at a temperature in the region of 20° C. and then 17.8 cm$^3$ of benzyl alcohol are added. The reaction mixture is stirred for twenty hours at a temperature in the region of 20° C. and diluted with 100 cm$^3$ of dichloromethane and 200 cm$^3$ of a saturated aqueous sodium hydrogencarbonate solution. The organic phase is separated by settling, washed with two times 100 cm$^3$ of a saturated aqueous sodium hydrogencarbonate solution and then 100 cm$^3$ of a saturated aqueous sodium chloride solution. The aqueous phases are extracted with two times 100 cm$^3$ of dichloromethane. The organic phases are combined, dried over magnesium sulphate and concentrated under reduced pressure. The residue is purified by chromatography on silica [eluent: cyclohexane/ethyl acetate (50/50 by volume)]. The fractions containing the expected product are combined and concentrated under reduced pressure. There are thus obtained 20.26 g of benzyl 3-nitrophenylacetate in the form of an oil used as is in the subsequent syntheses.

EXAMPLE 26

A The reaction is carried out in a way analogous to that described in Example 3, but from 1.85 g of tert-butyl (2RS,4SR,5SR)-1-{2-[3-(3-(ethoxycarbonyl)phenyl)ureido]acetyl}-5-phenyl-4-(1-pyrrolidinylcarbonyl)pyrrolidine-2-carboxylate and 0.18 g of potassium hydroxide in a mixture of 20 cm$^3$ of distilled water and 50 cm$^3$ of methanol. After treatment, there is obtained 0.76 g of (2RS,4SR,5SR)-3-{3-[2-(2-tert-butoxycarbonyl-5-phenyl-4-(1-pyrrolidinylcarbonyl)-1-pyrrolidinyl)-2-oxoethyl]ureido}benzoic acid [R$_f$=0.17; eluent: methylene chloride/methanol (97.5/2.5)].

B tert-Butyl (2RS,4SR,5SR)-1-{2-[3-(3-(ethoxycarbonyl)phenyl)ureido]acetyl}-5-phenyl-4-(1-pyrrolidinylcarbonyl)pyrrolidine-2-carboxylate can be prepared as described in Example 17B, but from 2.3 g of tert-butyl (2RS,4SR,5SR)-1-(2-aminoacetyl)-5-phenyl-4-(1-pyrrolidinylcarbonyl)pyrrolidine-2-carboxylate and 1.1 g of ethyl 3-isocyanatobenzoate in 120 cm$^3$ of tetrahydrofuran. After treatment, there are obtained 1.87 g of tert-butyl (2RS,4SR,5SR)-1-{2-[3-(3-(ethoxycarbonyl)phenyl)ureido]acetyl}-5-phenyl-4-(1-pyrrolidinylcarbonyl)pyrrolidine-2-carboxylate in the form of a foam used as is in the subsequent syntheses.

C tert-Butyl (2RS,4SR,5SR)-1-(2-aminoacetyl)-5-phenyl-4-(1-pyrrolidinylcarbonyl)pyrrolidine-2-carboxylate can be prepared as described in Example 16C, but from 3.65 g of tert-butyl (2RS,4SR,5SR)-1-[2-(tert-butoxycarbonylamino)acetyl]-5-phenyl-4-(1-pyrrolidinylcarbonyl)pyrrolidine-2-carboxylate and 1.04 cm$^3$ of iodotrimethylsilane in 100 cm$^3$ of chloroform. After treatment, there are obtained 2.3 g of tert-butyl (2RS,4SR,5SR)-1-(2-aminoacetyl)-5-phenyl-4-(1-pyrrolidinylcarbonyl)pyrrolidine-2-carboxylate in the form of a foam used as is in the subsequent syntheses.

D tert-Butyl (2RS,4SR,5SR)-1-[2-(tert-butoxycarbonylamino)acetyl]-5-phenyl-4-(1-pyrrolidinylcarbonyl)pyrrolidine-2-carboxylate can be prepared in the following way: 2.23 g of N,N-carbonyldiimidazole are added to a solution of 5.61 g of 2-tert-butyl hydrogen (2RS,4SR,5SR)-1-[2-(tert-butoxycarbonylamino)acetyl]-5-phenylpyrrolidine-2,4-dicarboxylate in 75 cm$^3$ of 1,2-dichloroethane. The reaction mixture is stirred for three hours at a temperature in the region of 20° C. and then 1.05 cm$^3$ of pyrrolidine and 0.1 g of 4-dimethylaminopyridine are added. The reaction mixture is stirred for twenty hours at a temperature in the region of 20° C. The organic phase is then washed with 100 cm$^3$ of distilled water, two times 100 cm$^3$ of a normal aqueous hydrochloric acid solution, two times 100 cm$^3$ of a normal aqueous sodium hydroxide solution and two times 100 cm$^3$ of a saturated aqueous sodium chloride solution, dried over sodium sulphate and concentrated under reduced pressure. The residue is purified by chromatography on silica [eluent: cyclohexane/ethyl acetate (30/70 by volume)]. The fractions containing the expected product are combined and concentrated under reduced pressure. There are thus obtained 3.67 g of tert-butyl (2RS,4SR,5SR)-1-[2-(tert-butoxycarbonylamino)acetyl]-5-phenyl-4-(1-pyrrolidinylcarbonyl)pyrrolidine-2-carboxylate in the form of a foam used as is in the subsequent syntheses.

EXAMPLE 27

A The reaction is carried out in a way analogous to that described in Example 3, but from 2.3 g of tert-butyl (2RS,4SR,5SR)-4-(3,3-dimethylpiperidinocarbonyl)-1-{2-[3-(3-(ethoxycarbonyl)phenyl)ureido]acetyl}-5-phenylpyrrolidine-2-carboxylate and 0.2 g of potassium hydroxide in a mixture of 20 cm$^3$ of distilled water and 50 cm$^3$ of methanol. After treatment, there are obtained 1.16 g of (2RS,4SR,5SR)-3-{3-[2-(2-tert-butoxycarbonyl-4-(3,3-dimethylpiperidinocarbonyl)-5-phenyl-1-pyrrolidinyl)-2-oxoethyl]ureido}benzoic acid [R$_f$=0.2; eluent=methylene chloride/methanol (97.5/2.5)].

B tert-Butyl (2RS,4SR,5SR)-4-(3,3-dimethylpiperidinocarbonyl-1-{2-[3-(3-(ethoxycarbonyl)phenyl)ureido]acetyl}-5-phenylpyrrolidine-2-carboxylate can be prepared as described in Example 17B, but from 2.7 g of tert-butyl (2RS,4SR,5SR)-1-(2-aminoacetyl)-4-(4-(3,3-dimethylpiperidinocarbonyl)-5-phenylpyrrolidine-2-carboxylate and 1.17 g of ethyl 3-isocyanatobenzoate in 120 cm$^3$ of tetrahydrofuran. After treatment, there are obtained 2.3 g of tert-butyl (2RS,4SR,5SR)-4-(3,3-dimethylpiperidinocarbonyl)-1-{2-[3-(3-(ethoxycarbonyl)phenyl)ureido]acetyl}-5-phenylpyrrolidine-2-carboxylate in the form of a foam used as is in the subsequent syntheses.

C tert-Butyl (2RS,4SR,5SR)-1-(2-aminoacetyl)-4-(3,3-dimethylpiperidinocarbonyl)-5-phenylpyrrolidine-2-carboxylate can be prepared as described in Example 16C, but from 3.85 g of tert-butyl (2RS,4SR,5SR)-1-[2-(tert-butoxycarbonylamino)acetyl]-4-(3,3-dimethylpiperidinocarbonyl)-5-phenylpyrrolidine-2-carboxylate and 1.01 cm$^3$ of iodotrimethylsilane in 100 cm$^3$ of chloroform. After treatment, there are obtained 2.7 g of tert-butyl (2RS,4SR,5SR)-1-(2-aminoacetyl)-4-(3,3-dimethylpiperidinocarbonyl)-5-phenylpyrrolidine-2-carboxylate in the form of a foam used as is in the subsequent syntheses.

D tert-Butyl (2RS,4SR,5SR)-1-[2-(tert-butoxycarbonylamino)acetyl]-4-(3,3-dimethylpiperidinocarbonyl)-5-phenylpyrrolidine-2-carboxylate can be prepared as described in Example 26D, but from 4.5 g of 2-tert-butyl hydrogen (2RS,4SR,5SR)-1-[2-(tert-butoxycarbonylamino)acetyl]-5-phenylpyrrolidine-2,4-dicarboxylate, 1.78 g of N,N-carbonyldiimidazole, 1.35 cm³ of 3,3-dimethylpiperidine and 0.1 g of 4-dimethylaminopyridine in 75 cm³ of 1,2-dichloroethane. After treatment, there are obtained 3.86 g of tert-butyl (2RS,4SR,5SR)-1-[2-(tert-butoxycarbonylamino)acetyl]-4-(3,3-dimethylpiperidinocarbonyl)-5-phenylpyrrolidine-2-carboxylate in the form of a foam used as is in the subsequent syntheses.

EXAMPLE 28

A The reaction is carried out in a way analogous to that described in Example 3, but from 2.62 g of tert-butyl (2RS,4RS,5SR)-4-acetyl-1-{2-[3-(3-(methoxycarbonyl)phenyl)ureido]acetyl}-5-phenylpyrrolidine-2-carboxylate in a mixture of 5 cm³ of a normal aqueous potassium hydroxide solution, 25 cm³ of distilled water and 100 cm³ of methanol. After treatment, there is obtained 0.6 g of (2RS,4SR,5SR)-3-{3-[2-(4-acetyl-2-tert-butoxycarbonyl-5-phenyl-1-pyrrolidinyl)-2-oxoethyl]ureido}benzoic acid, melting at 145° C.

B tert-Butyl (2RS,4RS,5SR)-4-acetyl-1-{2-[3-(3-(methoxycarbonyl)phenyl)ureido]acetyl}-5-phenylpyrrolidine-2-carboxylate can be prepared as described in Example 2B, but from 4.35 g of tert-butyl (2RS,4RS,5SR)-4-acetyl-5-phenylpyrrolidine-2-carboxylate, 3.8 g of 2-{3-[3-(methoxycarbonyl)phenyl]ureido}acetic acid and 3.1 g of N,N'-dicyclohexylcarbodiimide in 120 cm³ of acetonitrile. After treatment, there are obtained 8 g of tert-butyl (2RS,4RS,5SR)-4-acetyl-1-{2-[3-(3-(methoxycarbonyl)phenyl)ureido]acetyl}-5-5-phenylpyrrolidine-2-carboxylate in the form of a foam used as is in the subsequent syntheses.

C 2-{3-[3-(Methoxycarbonyl)phenyl]ureido}acetic acid can be prepared as described in Example 1G, but from 5.88 g of methyl 3-isocyanatobenzoate, 2.5 g of glycine and 9.2 g of potassium carbonate in 75 cm³ of 1,4-dioxane and 90 cm³ of distilled water. After treatment, there are obtained 5.27 g of 2-{3-[3-(methoxycarbonyl)phenyl]ureido}acetic acid, melting at 220° C.

EXAMPLE 29

A The reaction is carried out in a way analogous to that described in Example 3, but from 1.1 g of methyl (2RS,4RS,5SR)-5-(2-fluorophenyl)-1-{2-[3-(3-(methoxycarbonylmethyl)phenyl)ureido]acetyl}-2-(methylphenylcarbamoyl)pyrrolidine-4-carboxylate and 0.21 g of potassium hydroxide in a mixture of 20 cm³ of distilled water and 40 cm³ of methanol. After treatment, there is obtained 0.5 g of (2RS,4SR,5SR)-5-(2-fluorophenyl)-1-{2-[3-(3-(carboxymethyl)phenyl)ureido]acetyl}-2-(methylphenylcarbamoyl)pyrrolidine-4-carboxylic acid, melting at 164° C.

B Methyl (2RS,4RS,5SR)-5-(2-fluorophenyl)-1-{2-[3-(3-(methoxycarbonylmethyl)phenyl)ureido]acetyl}-2-(methylphenylcarbamoyl)pyrrolidine-4-carboxylate can be prepared as described in Example 2B, but from 0.95 g of methyl (2RS,4RS,5SR)-5-(2-fluorophenyl)-2-(methylphenylcarbamoyl)pyrrolidine 4-carboxylate, 0.69 g of 2-{3-[3-(methoxycarbonylmethyl)phenyl]ureido}acetic acid and 0.54 g of N,N'-dicyclohexylcarbodiimide in 50 cm³ of acetonitrile. After treatment, there are obtained 1.1 g of methyl (2RS,4RS,5SR)-5-(2-fluorophenyl)-1-{2-[3-(3-(methoxycarbonylmethyl)phenyl)ureido]acetyl}-2-(methylphenylcarbamoyl)pyrrolidine-4-carboxylate in the form of a foam used as is in the subsequent syntheses.

C Methyl (2RS,4RS,5SR)-5-(2-fluorophenyl)-2-(methylphenylcarbamoyl)pyrrolidine-4-carboxylate can be prepared in the following way: 0.37 cm³ of iodotrimethylsilane is added to a solution of 1.2 g of methyl (2RS,4RS,5SR)-1-tert-butoxycarbonyl-5-(2-fluorophenyl)-2-(methylphenylcarbamoyl)pyrrolidine-4-carboxylate in 50 cm³ of chloroform. The reaction mixture is stirred for twenty hours at a temperature in the region of 20° C. and then 100 cm³ of a saturated aqueous sodium hydrogencarbonate solution is added. The organic phase is separated by settling, washed with a saturated aqueous sodium chloride solution, dried over magnesium sulphate and concentrated under reduced pressure. There is thus obtained 0.95 g of methyl (2RS,4RS,5SR)-5-(2-fluorophenyl)-2-(methylphenylcarbamoyl)pyrrolidine-4-carboxylate in the form of an oil used as is in the subsequent syntheses.

D Methyl (2RS,4RS,5SR)-1-tert-butoxycarbonyl-5-(2-fluorophenyl)-2-(methylphenylcarbamoyl)pyrrolidine-4-carboxylate can be prepared in the following way: 2.1 g of N,N'-dicyclohexylcarbodiimide are added to a solution of 3.68 g of 4-methyl hydrogen (2RS,4RS,5SR)-1-tert-butoxycarbonyl-5-(2-fluorophenyl)pyrrolidine-2,4-dicarboxylate in a mixture of 1.1 cm³ of N-methylaniline and 50 cm³ of acetonitrile. The reaction mixture is stirred for four hours at a temperature in the region of 20° C. and is then concentrated under reduced pressure. The residue is taken up in 100 cm³ of ethyl acetate and filtered. The precipitate is rinsed with 50 cm³ of ethyl acetate and the filtrates are then combined and concentrated under reduced pressure. The residue is purified by chromatography on silica [eluent: ethyl acetate/cyclohexane (50/50 by volume)]. The fractions containing the expected product are combined and concentrated under reduced pressure. There are thus obtained 1.2 g of methyl (2RS,4RS,5SR)-1-tert-butoxycarbonyl-5-(2-fluorophenyl)-2-(methylphenylcarbamoyl)pyrrolidine-4-carboxylate in the form of an oil used as is in the subsequent syntheses.

E 4-Methyl hydrogen (2RS,4RS,5SR)-1-tert-butoxycarbonyl-5-(2-fluorophenyl)pyrrolidine-2,4-dicarboxylate can be prepared in the following way: a solution of 5.2 g of di-tert-butyl dicarbonate in 30 cm³ of 1,2-dioxane is added, at a temperature in the region of 10° C., to a solution of 7.2 g of 4-methyl hydrogen (2RS,4RS,5SR)-5-(2-fluorophenyl)pyrrolidine-2,4-dicarboxylate hydrochloride and 4.9 g of sodium carbonate in 40 cm³ of water. The reaction mixture is stirred for two hours at a temperature in the region of 20° C. 100 cm³ of distilled water are then added end washing is carried out with two times 50 cm³ of ethyl acetate. The aqueous phase is acidified to a pH in the region of 1 by addition of a normal aqueous hydrochloric acid solution and extracted with three times 100 cm³ of dichloromethane. The organic extracts are combined, washed with a saturated aqueous sodium chloride solution, dried over magnesium sulphate and concentrated under reduced pressure. The residue is crystallized from diisopropyl ether. There are thus obtained 7.35 g of 4-methyl hydrogen (2RS,4RS,5SR)-1-tert-butoxy-carbonyl-5-(2-fluorophenyl)pyrrolidine-2,4-dicarboxylate, melting at 172° C.

F 4-Methyl hydrogen (2RS,4RS,5SR)-5-(2-fluorophenyl) pyrrolidine-2,4-dicarboxylate hydrochloride can be prepared in the following way: 0.6 g of 10% palladium-on-charcoal is added to a solution of 12 g of 2-benzyl 4-methyl (2RS,4RS,5SR)-5-(2-fluorophenyl)pyrrolidine-2,4-dicarboxylate in 150 cm³ of ethanol. The reaction mixture is stirred for twenty hours at a temperature in the region of 20° C. under a hydrogen pressure of 129 kPa and is then purged with nitrogen. The catalyst is separated by filtration and rinsed with three times 25 cm³ of a normal aqueous hydrochloric acid solution. The combined aqueous phases are concentrated under reduced pressure and the residue taken up in dichloromethane and filtered. The filtrate is concentrated under reduced pressure and the residue is crystallized from acetonitrile. There are thus obtained 7.2 g of 4-methyl hydrogen (2RS,4RS,5SR)-5-(2-fluorophenyl)pyrrolidine-2,4-dicarboxylate hydrochloride, melting at 212° C.

G 2-Benzyl 4-methyl (2RS,4RS,5SR)-5-(2-fluorophenyl)-pyrrolidine-2,4-dicarboxylate can be prepared as described in Example 2C, but from 11 g of benzyl (2-fluorobenzylideneamino)acetate, 3.6 cm³ of methyl acrylate, 10 g of silver acetate and 5.6 cm³ of triethylamine in 200 cm³ of acetonitrile. After treatment, there are obtained 12 g of 2-benzyl 4-methyl (2RS,4RS,5SR)-5-(2-fluorophenyl)pyrrolidine-2,4-dicarboxylate in the form of an oil used as is in the subsequent syntheses.

H Benzyl (2-fluorobenzylideneamino)acetate can be prepared as described in Example 2D, but from 4.2 cm³ of 2-fluorobenzaldehyde, 8.07 g of benzyl glycinate hydrochloride, 6 g of 4 Å sieve and 5.6 cm³ of triethylamine in 75 cm³ of dichloromethane. After treatment, there are obtained 11 g of benzyl (2-fluorobenzylideneamino)acetate in the form of an oil used as is in the subsequent syntheses.

EXAMPLE 30

A The reaction is carried out in a way analogous to that described in Example 3, but from 1.6 g of methyl (2RS,4RS,5SR)-2-(3,3-dimethylpiperidinocarbonyl)-5-(2-fluorophenyl)-1-{2-[3-(3-(methoxycarbonylmethyl)phenyl)ureido]acetyl}pyrrolidine-4-carboxylate and 0.3 g of potassium hydroxide in a mixture of 20 cm³ of distilled water and 40 cm³ of methanol. After treatment, there is obtained 0.55 g of (2RS,4SR,5SR)-1-{2-[3-(3-(carboxymethyl)phenyl)ureido]acetyl}-2-(3,3-dimethylpiperidinocarbonyl)-5-(2-fluorophenyl) pyrrolidine-4-carboxylic acid, melting at 173° C.

B Methyl (2RS,4RS,5SR)-2-(3,3-dimethylpiperidinocarbonyl)-5-(2-fluorophenyl)-1-{2-[3-(3-(methoxycarbonylmethyl)phenyl)ureido]acetyl}pyrrolidine-4-carboxylate can be prepared as described in Example 2B, but from 1.2 g of methyl (2RS,4RS,5SR)-2-(3,3-dimethylpiperidinocarbonyl)-5-(2-fluorophenyl)pyrrolidine-4-carboxylate, 0.86 g of 2-{3-[3-(methoxycarbonylmethyl)phenyl]ureido}acetic acid and 0.67 g of N,N'-dicyclohexylcarbodiimide in 50 cm³ of acetonitrile. After treatment, there are obtained 1.6 g methyl (2RS,4RS,5SR)-2-(3,3-dimethylpiperidinocarbonyl)-5-(2-fluorophenyl)-1-{2-[3-(3-(methoxycarbonylmethyl)phenyl)ureido]acetyl}pyrrolidine-4-carboxylate in the form of a foam used as is in the subsequent syntheses.

C Methyl (2RS,4RS,5SR)-2-(3,3-dimethylpiperidinocarbonyl)-5-(2-fluorophenyl) pyrrolidine-4-carboxylate can be prepared as described in Example 29C, but from 1.5 g of methyl (2RS,4RS,5SR)-1-tert-butoxycarbonyl-2-(3,3-dimethylpiperidinocarbonyl)-5-(2-fluorophenyl)pyrrolidine-4-carboxylate and 0.47 g of iodotrimethylsilane in 50 cm³ of chloroform. After treatment, there are obtained 1.2 g of methyl (2RS,4RS,5SR)-2-(3,3-dimethylpiperidinocarbonyl)-5-(2-fluorophenyl)pyrrolidine-4-carboxylate in the form of an oil used as is in the subsequent syntheses.

D Methyl (2RS,4RS,5SR)-1-tert-butoxycarbonyl-2-(3,3-dimethylpiperidinocarbonyl)-5-(2-fluorophenyl)-pyrrolidine-4-carboxylate can be prepared in the following way: 1.78 g of N,N-carbonyldiimidazole are added to a solution of 3.48 g of 4-methyl hydrogen (2RS,4RS,5SR)-1-tert-butoxycarbonyl-5-(2-fluorophenyl)pyrrolidine-2,4-dicarboxylate in 50 cm³ of 1,2-dichloroethane. The mixture is stirred for two hours at a temperature in the region of 20° C. and then 1.35 cm³ of 3,3-dimethylpiperidine, diluted in 20 cm³ of 1,2-dichloroethane, and 0.1 g of 4-dimethylaminopyridine are added. The reaction mixture is stirred for twenty hours at a temperature in the region of 20° C. and then poured into 100 cm³ of distilled water. The organic phase is separated by settling, washed with two times 50 cm³ of a decinormal aqueous hydrochloric acid solution and then with a saturated aqueous sodium chloride solution, dried over magnesium sulphate and concentrated under reduced pressure. The residue is purified by chromatography on silica [eluent: ethyl acetate/cyclohexene (30/70 by volume)]. The fractions containing the expected product are combined and concentrated under reduced pressure. There are thus obtained 1.5 g of methyl (2RS,4RS,5SR)-1-tert-butoxycarbonyl-2-(3,3-dimethylpiperidinocarbonyl)-5-(2-fluorophenyl)pyrrolidine-4-carboxylate in the form of a foam used as is in the subsequent syntheses.

EXAMPLE 31

The reaction is carried out in a way analogous to that described in Example 3, but from 1.34 g of tert-butyl (2RS,4SR,5SR)-4-dimethylcarbamoyl-1-{2-[3-(3-(methoxycarbonyl)phenyl)ureido]acetyl}-5-phenylpyrrolidine-2-carboxylate and 0.14 g of potassium hydroxide in a mixture of 40 cm³ of distilled water and 60 cm³ of methanol. After treatment, there is obtained 0.6 g of (2RS,4SR,5SR)-3-{3-[2-(2-tert-butoxycarbonyl-4-dimethylcarbamoyl-5-phenyl-1-pyrrolidinyl)-2-oxoethyl] ureido}benzoic acid [R$_f$=0.2; eluent: methylene chloride/methanol (90/10)].

B tert-Butyl (2RS,4SR,5SR)-4-dimethylcarbamoyl-1-{2-[3-(3-(methoxycarbonyl)phenyl)ureido]acetyl}-5-phenylpyrrolidine-2-carboxylate can be prepared as described in Example 17B, but from 0.92 g of tert-butyl (2RS,4SR,5SR)-1-(2-aminoacetyl)-4-dimethylcarbamoyl-5-phenylpyrrolidine-2-carboxylate and 0.46 g of methyl 3-isocyanatobenzoate in 70 cm³ of tetrahydrofuran. After treatment, there are obtained 1.34 g of tert-butyl (2RS,4SR,5SR)-4-dimethylcarbamoyl-1-{2-[3-(3-(methoxycarbonyl) phenyl)ureido]acetyl}-5-phenylpyrrolidine-2-carboxylate in the form of a foam used as is in the subsequent syntheses.

C tert-Butyl (2RS,4SR,5SR)-1-(2-aminoacetyl)-4-dimethylcarbamoyl-5-phenylpyrrolidine-2-carboxylate can be prepared as described in Example 16C, but from 1.7 g of tert-butyl (2RS,4SR,5SR)-1-[2-(tert-butoxycarbonylamino) acetyl]-4-dimethylcarbamoyl-5-phenylpyrrolidine-2-carboxylate and 0.51 cm³ of iodotrimethylsilane in 50 cm³ of chloroform. After treatment, there is obtained 0.97 g of tert-butyl (2RS,4SR,5SR)-1-(2-aminoacetyl)-4-dimethylcarbamoyl-5-phenylpyrrolidine-2-carboxylate in the form of an oil used as is in the subsequent syntheses.

D tert-Butyl (2RS,4SR,5SR)-1-[2-(tert-butoxycarbonylamino)acetyl]-4-dimethylcarbamoyl-5- phenylpyrrolidine-2-carboxylate can be prepared in the following way: 0.1 g of N,N-dimethylformamide and then 0.42 cm³ of oxalyl chloride are added to a solution of 2 g of 2-tert-butyl hydrogen (2RS,4SR,5SR)-1-[2-(tert-butoxycarbonylamino)acetyl]-5-phenylpyrrolidine-2,4-dicarboxylate in 60 cm³ of diethyl ether. The reaction mixture is stirred for four hours at a temperature in the region of 20° C. and than dimethylamine is introduced by sparging for forty-five minutes. The mixture is stirred for twenty hours at a temperature in the region of 20° C. The precipitate which is formed is separated by filtration and is washed with three times 20 cm³ of dichloromethane. The organic phases are combined, diluted with 100 cm³ of dichloromethane and washed successively with two times 150 cm³ of water, two times 150 cm³ of a decinormal aqueous hydrochloric acid solution, 150 cm³ of water and two times 150 cm³ of a saturated aqueous sodium chloride solution. The organic phase is dried over magnesium sulphate and concentrated under reduced pressure. The residue is purified by chromatography on silica [eluent: dichloromethane/methanol (90/10 by volume)]. The fractions containing the expected product are combined and concentrated under reduced pressure. There is thus obtained 1 g of tert-butyl (2RS,4SR,5SR)-1-[2-(tert-butoxycarbonylamino)acetyl]-4-dimethylcarbamoyl-5-phenylpyrrolidine-2-carboxylate in the form of a foam used as is in the subsequent syntheses.

EXAMPLE 32

A The reaction is carried out in a way analogous to that described in Example 2A, but from 2.6 g of tert-butyl (2RS,4RS,5SR)-1-{2-[3-(3-(benzyloxycarbonyl)phenyl)ureido]acetyl}-5-phenyl-4-(phenylcarbamoyl)pyrrolidine-2-carboxylate and 0.3 g of 10% palladium-on-charcoal in 150 cm³ of ethanol. After treatment, there are obtained 2.05 g of (2RS,4RS,5SR)-3-{3-[2-(2-tert-butoxycarbonyl-5-phenyl-4-phenylcarbamoyl-1-pyrrolidinyl)-2-oxoethyl]ureido}benzoic acid [$R_f$=0.15; eluent: methylene chloride/methanol (80/20)].

B tert-Butyl (2RS,4RS,5SR)-1-{2-[3-(3-(benzyloxycarbonyl)phenyl)ureido]acetyl}-5-phenyl-4-(phenylcarbamoyl)pyrrolidine-2-carboxylate can be prepared in the following way: a solution of 2.69 g of tert-butyl (2RS,4RS,5SR)-1(2-aminoacetyl)-5-phenyl-4-(phenylcarbamoyl)pyrrolidine-2-carboxylate in 20 cm³ of dichloromethane is added to a solution of 1.13 g of N,N'-carbonyldiimidazole in 30 cm³ of dichloromethane. The reaction mixture is stirred for two hours at a temperature in the region of 20° C. and then a solution of 1.44 g of benzyl 3-aminobenzoate in 25 cm³ of dichloromethane is added. The reaction mixture is then heated at a temperature in the region of 40° C. for twenty hours. After cooling to a temperature in the region of 20° C., the reaction mixture is diluted with 150 cm³ of dichloromethane. The organic phase is then washed successively with two times 150 cm³ of distilled water, two times 150 cm³ of a decinormal aqueous hydrochloric acid solution, 150 cm³ of distilled water and two times 150 cm³ of a saturated aqueous sodium chloride solution. The organic phase is dried over magnesium sulphate and concentrated under reduced pressure. The residue is purified by chromatographing twice on silica [eluents: cyclohexane/ethyl acetate (30/70 then 50/50 by volume)]. The fractions containing the expected product are combined and concentrated under reduced pressure. There are thus obtained 2.6 g of tert-butyl (2RS,4RS,5SR)-1-{2-[3-(3-(benzyloxycarbonyl)phenyl)ureido]acetyl}-5-phenyl-4-(phenylcarbamoyl)pyrrolidine-2-carboxylate in the form of a foam used as is in the subsequent syntheses.

C tert-Butyl (2RS,4RS,5SR)-1-(2-aminoacetyl)-5-phenyl-4-(phenylcarbamoyl)pyrrolidine-2-carboxylate can be prepared as described in Example 16C, but from 5.05 g of tert-butyl (2RS,4RS,5SR)-1-[2-(tert-butoxycarbonylamino)acetyl]-5-phenyl-4-(phenylcarbamoyl)pyrrolidine-2-carboxylate and 0.83 cm³ of iodotrimethylsilane in 100 cm³ of chloroform. After treatment, there are obtained 2.69 g of tert-butyl (2RS,4RS,5SR)-1-(2-aminoacetyl)-5-phenyl-4-(phenylcarbamoyl) pyrrolidine-2-carboxylate in the form of an oil used as is in the subsequent syntheses.

D tert-Butyl (2RS,4RS,5SR)-1-[2-(tert-butoxycarbonylamino)acetyl]-5-phenyl-4-(phenylcarbamoyl)pyrrolidine-2-carboxylate can be prepared as described in Example 20D, but from 4.74 g of 2-tert-butyl hydrogen (2RS,4RS,5SR)-1-[2-(tert-butoxycarbonylamino)acetyl]-5-phenylpyrrolidine-2,4-carboxylate, 1 cm³ of aniline and 2.2 g of N,N'-dicyclohexylcarbodiimide in 50 cm³ of acetonitrile. After treatment, there are obtained 3.07 g of tert-butyl (2RS,4RS,5SR)-1-[2-(tert-butoxycarbonylamino)acetyl]-5-phenyl-4-(phenylcarbamoyl)pyrrolidine-2-carboxylate in the form of a foam used as is in the subsequent syntheses.

E 2-tert-Butyl hydrogen (2RS,4RS,5SR)-1-[2-(tert-butoxycarbonylamino)acetyl]-5-phenylpyrrolidine-2,4-dicarboxylate can be prepared in the following way: a suspension of 0.6 g of 5% palladium-on-charcoal in a solution of 5.74 g of 4-benzyl 2-tert-butyl (2RS,4RS,5SR)-1-[2-(tert-butoxycarbonylamino)acetyl]-5-phenylpyrrolidine-2,4-dicarboxylate in 350 cm³ of methanol is stirred for one hour under a hydrogen atmosphere (130 kPa) and at a temperature in the region of 20° C. The catalyst is separated by filtration and rinsed with three times 50 cm³ of methanol. The filtrate is concentrated under reduced pressure. There are thus obtained 4.74 g of 2-tert-butyl hydrogen (2RS,4RS,5SR)-1-[2-(tert-butoxycarbonylamino)acetyl]-5-phenylpyrrolidine-2,4-dicarboxylate in the form of a foam used as is in the subsequent syntheses.

F 4-Benzyl 2-tert-butyl (2RS,4RS,5SR)-1-[2-(tert-butoxycarbonylamino)acetyl]-5-phenylpyrrolidine-2,4-dicarboxylate can be prepared as described in Example 16D, but from 3.8 g of 4-benzyl 2-tert-butyl (2RS,4RS,5SR)-5-phenylpyrrolidine-2,4-dicarboxylate, 1.75 g of 2-(tert-butoxycarbonylamino)acetic acid and 2.06 g of N,N'-dicyclohexylcarbodiimide in 50 cm³ of acetonitrile. After treatment, there are obtained 2.06 g of 4-benzyl 2-tert-butyl (2RS,4RS,5SR)-1-[2-(tert-butoxycarbonylamino)acetyl]-5-phenylpyrrolidine-2,4-dicarboxylate in the form of a foam used as is in the subsequent syntheses.

EXAMPLE 33

The reaction is carried out in a way analogous to that described in Example 10, but from 1.7 g of (2RS,4SR,5SR)-3-{3-[2-(4-acetyl-2-tert-butoxycarbonyl-5-phenyl-1-pyrrolidinyl)-2-oxoethyl]ureido}benzoic acid and 0.26 g of hydroxylammonium chloride in a mixture of 3 cm³ of pyridine, 6 cm³ of methanol and 3 cm³ of distilled water. After treatment, there is obtained 0.43 g of (2RS,4SR,5SR)-3-{3-[2-(2-tert-butoxycarbonyl-4-(1-(hydroxyimino)ethyl)-5-phenyl-1-pyrrolidinyl)-2-oxoethyl]ureido}benzoic acid, melting at 180° C.

EXAMPLE 34

A The reaction is carried out in a way analogous to that described in Example 3, but from 1.1 g of tert-butyl (2RS,4SR,5SR)-1-{2-[3-(3-(ethoxycarbonyl)phenyl)ureido]

acetyl}-5-(2-fluorophenyl)-4-(2-phenyl-1,3-dioxalan-2-yl) pyrrolidine-2-carboxylate and 0.09 g of potassium hydroxide in 10 cm³ of distilled water and 30 cm³ of methanol. After treatment, there is obtained 0.15 g of (2RS,4SR,5SR)-3-{3-[2-(4-benzoyl-2-tert-butoxycarbonyl-5-(2-fluorophenyl)-1-pyrrolidinyl)-2-oxoethyl] ureido}benzoic acid ($R_f$=0.275 eluent: methylene chloride/methanol (90/10)] and 0.35 g of tert-butyl (2RS,4SR,5SR)-4-benzoyl-5-(2-fluorophenyl)-1-{2-[3-(3-(methoxycarbonyl)phenyl)ureido]acetyl}pyrrolidine-2-carboxylate [$R_f$=0.13; eluent: cyclohexane/ethyl acetate (70/30)].

B tert-Butyl (2RS,4SR,5SR)-1-{2-[3-(3-(ethoxycarbonyl)phenyl)ureido]acetyl}-5-(2-fluorophenyl)-4-(2-phenyl-1,3-dioxalan-2-yl)pyrrolidine-2-carboxylate can be prepared in the following way: a solution of 1 g of tert-butyl (2RS,4SR,5SR)-4-benzoyl-1-{2-[3-(3-(methoxycarbonyl)phenyl) ureido]acetyl}-5-(2-fluorophenyl)pyrrolidine-2-carboxylate and 0.05 g of para-toluenesulphonic acid in a mixture of 0.09 cm³ of ethylene glycol and 100 cm³ of toluene is heated at reflux for four hours. After cooling to a temperature in the region of 20° C., the organic phase is washed with water, dried over magnesium sulphate and concentrated under reduced pressure. There are thus obtained 1.1 g of tert-butyl (2RS,4SR,5SR)-1-{2-[3-(3-(ethoxycarbonyl)phenyl)ureido] acetyl}-5-(2-fluorophenyl)-4-(2-phenyl-1,3-dioxalan-2-yl) pyrrolidine-2-carboxylate in the form of an oil used as is in the subsequent syntheses.

C tert-Butyl (2RS,4SR,5SR)-4-benzoyl-1-{2-[3-(3-(ethoxycarbonyl)phenyl)ureido]acetyl}-5-(2-fluorophenyl) pyrrolidine-2-carboxylate can be prepared in the following way: a solution of 1.3 g of tert-butyl (2RS,4RS,5SR)-4-benzoyl-1-{2-[3-(3-(ethoxycarbonyl)phenyl)ureido]acetyl}-5-(2-fluorophenyl)pyrrolidine-2-carboxylate and 0.12 g of potassium hydroxide in a mixture of 30 cm³ of methanol and 10 cm³ of distilled water is stirred at a temperature in the region of 20° C. for four days. The reaction mixture is concentrated under reduced pressure, diluted with 100 cm³ of distilled water and brought to a pH in the region of 1 with a normal aqueous hydrochloric acid solution. The aqueous phase is extracted with three times 100 cm³ of ethyl acetate. The organic extracts are combined, washed with a saturated aqueous sodium chloride solution and concentrated under reduced pressure. The residue is purified by chromatography on silica [eluent: dichloromethane/methanol (90/10 by volume)]. The fractions containing the expected product are combined and concentrated under reduced pressure. There is thus obtained 1 g of tert-butyl (2RS,4SR,5SR)-4-benzoyl-1-{2-[3-(3-(ethoxycarbonyl)phenyl)ureido]acetyl}-5-(2-fluorophenyl)pyrrolidine-2-carboxylate in the form of an amorphous solid used as is in the subsequent syntheses.

D tert-Butyl (2RS,4RS,5SR)-4-benzoyl-1-{2-[3-(3-(ethoxycarbonyl)phenyl)ureido]acetyl}-5-(2-fluorophenyl) pyrrolidine-2-carboxylate can be prepared as described in Example 2B, but from 1.26 g of tert-butyl (2RS,4RS,5SR) -4-benzoyl-5-(2-fluorophenyl)pyrrolidine-2-carboxylate, 0.91 g of 2-{3-[3-(ethoxycarbonyl)phenyl]ureido}acetic acid and 0.7 g of N,N'-dicyclohexylcarbodiimide in 50 cm³ of acetonitrile. After treatment, there are obtained 2 g of tert-butyl (2RS,4RS,5SR)-4-benzoyl-1-{2-[3-(3-(ethoxycarbonyl)phenyl)ureido]acetyl}-5-(2-fluorophenyl) pyrrolidine-2-carboxylate in the form of an amorphous solid used as is in the subsequent syntheses.

E tert-Butyl (2RS,4RS,5SR)-4-benzoyl-5-(2-fluorophenyl)pyrrolidine-2-carboxylate can be prepared as described in Example 2C, but from 7.1 g of tert-butyl (2-fluorobenzylideneamino)acetate, 3.9 g of phenyl vinyl ketone, 7.5 g of silver acetate and 4.2 cm³ of triethylamine in 200 cm³ of acetonitrile. After treatment, there are obtained 2.5 g of tert-butyl (2RS,4RS,5SR)-4-benzoyl-5-(2-fluorophenyl)pyrrolidine-2-carboxylate in the form of an amorphous solid used as is in the subsequent syntheses. Phenyl vinyl ketone can be prepared according to the method described by R. T. Parfit et al., Eur. J. Med. Chem., 20, 228 (1985).

F 2-{3-[3-(Ethoxycarbonyl)phenyl]ureido}acetic acid can be prepared as described in Example 1G, but from 10 g of ethyl 3-isocyanatobenzoate, 3.95 g of glycine and 4.4 g of sodium hydrogencarbonate in 60 cm³ of distilled water. After treatment, there are obtained 5.3 g of 2-{3-[3-(ethoxycarbonyl)phenyl]ureido}acetic acid, melting at 174° C.

EXAMPLE 35

A The reaction is carried out in a way analogous to that described in Example 3, but from 2.1 g of methyl (2RS, 4SR,5RS)-3-{3-[2-(5-(2-fluorophenyl)-2-(methylphenylcarbamoyl)-4-phenylsulphonyl-1-pyrrolidinyl)-2-oxoethyl]ureido}phenylacetate and 0.17 g of potassium hydroxide in a mixture of 20 cm³ of distilled water and 60 cm³ of methanol. After treatment, there is obtained 0.8 g of (2RS,4SR,5RS)-3-{3-[2-(5-(2-fluorophenyl)-2-(methylphenylcarbamoyl)-4-phenylsulphonyl-1-pyrrolidinyl)-2-oxoethyl] ureido}phenylacetic acid [$R_f$=0.26; eluent: methylene chloride/methanol (90/10)].

B Methyl (2RS,4SR,5RS)-3-{3-[2-(5-(2-fluorophenyl)-2-(methylphenylcarbamoyl)-4-phenylsulphonyl-1-pyrrolidinyl)-2-oxoethyl]ureido}phenylacetate can be prepared as described in Example 2B, but from 1.9 g of (2RS,4SR,5RS)-5-(2-fluorophenyl)-4-phenylsulphonyl-N-methyl-N-phenylpyrrolidine-2-carboxamide, 1.15 g of 2-{3-[3-(methoxycarbonylmethyl)phenyl]ureido}acetic acid and 0.9 g of N,N'-dicyclohexylcarbodiimide in 50 cm³ of acetonitrile. After treatment, there are obtained 2.1 g of methyl (2RS,4SR,5RS)-3-{3-[2-(5-(2-fluorophenyl)-2-(methylphenylcarbamoyl)-4-phenylsulphonyl-1-pyrrolidinyl)-2-oxoethyl]ureido}phenylacetate in the form of a foam used as is in the subsequent syntheses.

C (2RS,4SR,5RS)-5-(2-Fluorophenyl)-4-phenylsulphonyl-N-methyl-N-phenylpyrrolidine-2-carboxamide can be prepared as described in Example 29C, but from 2.5 g of (2RS,4SR,4RS)-1-tert-butoxycarbonyl-5-(2-fluorophenyl)-4-phenylsulphonyl-N-methyl-N-phenylpyrrolidine-2-carboxamide and 0.66 cm³ of iodotrimethylsilane in 50 cm³ of chloroform. After treatment, there are obtained 1.9 g of (2RS,4SR,5RS)-5-(2-fluorophenyl)-4-phenylsulphonyl-N-methyl-N-phenylpyrrolidine-2-carboxamide in the form of a foam used as is in the subsequent syntheses.

D (2RS,4SR,4RS)-1-tert-Butoxycarbonyl-5-(2-fluorophenyl)-4-phenylsulphonyl-N-methyl-N-phenylpyrrolidine-2-carboxamide can be prepared as described in Example 29D, but from 4.5 g of (2RS,4SR,5RS)-1-tert-butoxycarbonyl-5-(2-fluorophenyl)-4-(phenylsulphonyl)pyrrolidine-2-carboxylic acid, 1.1 cm³ of N-methylaniline and 2.1 g of N,N'-dicyclohexylcarbodiimide in 100 cm³ of acetonitrile. After treatment, there are obtained 2.5 g of (2RS,4SR,4RS)-1-tert-butoxycarbonyl-5-(2-fluorophenyl)-4-phenylsulphonyl-N-methyl-N-phenylpyrrolidine-2-carboxamide in the form of a foam used as is in the subsequent syntheses.

E (2RS,4SR,5RS)-1-tert-Butoxycarbonyl-5-(2-fluorophenyl)-4-(phenylsulphonyl)pyrrolidine-2-carboxylic acid can be prepared as described in Example 29E, but from 5 g of (2RS,4SR,5RS)-5-(2-fluorophenyl)-4-(phenylsulphonyl)pyrrolidine-2-carboxylic acid hydrochloride, 6.5 g of di-tert-butyl dicarbonate and 5.8 g of sodium carbonate in a mixture of 60 cm³ of distilled water and 30 cm³ of 1,4-dioxane. After treatment, there are obtained 5 g of (2RS,4SR,5RS)-1-tert-butoxycarbonyl-5-(2-fluorophenyl)-4-(phenylsulphonyl)pyrrolidine-2-carboxylic acid, melting at 186° C.

F (2RS,4SR,5RS)-5-(2-Fluorophenyl)-4-(phenylsulphonyl)pyrrolidine-2-carboxylic acid hydrochloride can be prepared in the following way: 3.6 g of potassium hydroxide are added to a solution of 15.3 g of benzyl (2RS,4SR,5RS)-5-(2-fluorophenyl)-4-(phenylsulphonyl) pyrrolidine-2-carboxylate hydrochloride in a mixture of 250 cm³ of methanol and 80 cm³ of distilled water. The reaction mixture is stirred for twenty hours at a temperature in the region of 20° C. and is then concentrated under reduced pressure. The residue is taken up in 100 cm³ of distilled water. The aqueous phase is washed with two times 100 cm³ of ethyl acetate, acidified to a pH in the region of 1 with a 4N aqueous hydrochloric acid solution and cooled for fifteen minutes at a temperature in the region of 4° C. The solid which precipitates is separated by filtration, washed with three times 50 cm³ of distilled water an6 dried under reduced pressure at a temperature in the region of 40° C. There are thus obtained 10.3 g of (2RS,4SR,5RS)-5-(2-fluorophenyl)-4-(phenylsulphonyl)pyrrolidine-2-carboxylic acid hydrochloride, melting at 212° C.

G Benzyl (2RS,4SR,5RS)-5-(2-fluorophenyl)-4-(phenylsulphonyl)pyrrolidine-2-carboxylate hydrochloride can be prepared as described in Example 2C, but from 27.4 g of benzyl (2-fluorobenzylideneamino)acetate, 16.85 g of phenyl vinyl sulphone, 25.1 g of silver acetate and 12 cm³ of triethylamine in 400 cm³ of acetonitrile. After treatment, there are obtained 15.3 g of benzyl (2RS,4SR,5RS)-5-(2-fluorophenyl)-4-(phenylsulphonyl)pyrrolidine-2-carboxylate hydrochloride.

EXAMPLE 36

A The reaction is carried out in a way analogous to that described in Example 3, but from 2.5 g of methyl (2RS,4SR,5RS)-3-{3-[2-(5-(2-fluorophenyl)-4-phenylsulphonyl-2-(1-pyrrolidinylcarbonyl)-1-pyrrolidinyl)-2-oxoethyl]ureido}phenylacetate and 0.22 g of potassium hydroxide in a mixture of 20 cm³ of distilled water and 60 cm³ of methanol. After treatment, there are obtained 1.6 g of (2RS,4SR,5RS)-3-{3-[2-(5-(2-fluorophenyl)-4-phenylsulphonyl-2-(1-pyrrolidinylcarbonyl)-1-pyrrolidinyl)-2-oxoethyl]ureido}phenylacetic acid [R$_f$=0.2; eluent: methylene chloride/methanol (90/10)].

B Methyl (2RS,4SR,5RS)-3-{3-[2-(5-(2-fluorophenyl)-4-phenylsulphonyl-2-(1-pyrrolidinylcarbonyl)-1-pyrrolidinyl)-2-oxoethyl]ureido}phenylacetate can be prepared as described in Example 2B, but from 2.3 g of (2RS,4SR,5RS)-5-(2-fluorophenyl)-4-phenylsulphonyl-N,N-tetramethylenepyrrolidine-2-carboxamide, 1.52 g of 2-{3-[3-(methoxycarbonylmethyl)phenyl]ureido}acetic acid and 1.18 g of N,N'-dicyclohexylcarbodiimide in 50 cm³ of acetonitrile. After treatment, there are obtained 2.5 g of methyl (2RS,4SR,5RS)-3-{3-[2-(5-(2-fluorophenyl)-4-phenylsulphonyl-2-(1-pyrrolidinylcarbonyl)-1-pyrrolidinyl)-2-oxoethyl]ureido}phenylacetate, melting at 156° C.

C (2RS,4SR,5RS)-5-(2-Fluorophenyl)-4-phenylsulphonyl-N,N-tetramethylenepyrrolidine-2-carboxamide, can be prepared as described in Example 29C, but from 3 g of (2RS,4SR,5RS)-1-tert-butoxycarbonyl-5-(2-fluorophenyl)-4-phenylsulphonyl-N,N-tetramethylenepyrrolidine-2-carboximide and 0.85 cm³ of iodotrimethylsilane in 50 cm³ of chloroform. After treatment, there are obtained 2.3 g of (2RS,4SR,5RS)-5-(2-fluorophenyl)-4-phenylsulphonyl-N,N-tetramethylenepyrrolidine-2-carboxamide in the form of a foam used as is in the subsequent syntheses.

D (2RS,4SR,5RS)-1-tert-Butoxycarbonyl-5-(2-fluorophenyl)-4-phenylsulphonyl-N,N-tetramethylenepyrrolidine-2-carboximide can be prepared as described in Example 30D, but from 2.8 g of (2RS,4SR,5RS)-1-tert-butoxycarbonyl-5-(2-fluorophenyl)-4-(phenylsulphonyl)pyrrolidine-2-carboxylic acid, 0.85 cm³ of pyrrolidine, 0.05 g of 4-dimethylaminopyridine and 1.1 g of N,N'-carbonyldiimidazole in 50 cm³ of acetonitrile. After treatment, there are obtained 3 g of (2RS,4SR,5RS)-1-tert-butoxycarbonyl-5-(2-fluorophenyl)-4-phenylsulphonyl-N,N-tetramethylenepyrrolidine-2-carboximide in the form of a foam used as is in the subsequent syntheses.

EXAMPLE 37

A The reaction is carried out in a way analogous to that described in Example 2A, but from 0.4 g of tert-butyl (2R*,4S*,5R*)-1-{2-[3-(3-(1-(benzyloxycarbonyl)ethyl (form B))phenyl)ureido]acetyl}-5-(2-fluorophenyl)-4-(phenylsulphonyl)pyrrolidine-2-carboxylate and 0.05 g of 10% palladium-on-charcoal in 30 cm³ of ethanol. After treatment, there is obtained 0.23 g of (2R*,4S*,5R*)-2-{3-[3-(2-(2-tert-butoxycarbonyl-5-(2-fluorophenyl)-4-phenylsulphonyl-1-pyrrolidinyl)-2-oxoethyl)ureido]phenyl}proprionic acid (form B) [R$_f$=0.69; eluent: methylene chloride/methanol (90/10)].

B tert-Butyl (2R*,4S*,5R*)-1-{2-[3-(3-(1-(benzyloxycarbonyl)ethyl(form B))phenyl)ureido]acetyl}-5-(2-fluorophenyl)-4-(phenylsulphonyl)pyrrolidine-2-carboxylate can be prepared as described in Example 17B, but from 0.75 g of tert-butyl (2R*,4S*,5R*)-1-(2-aminoacetyl)-5-(2-fluorophenyl)-4-(phenylsulphonyl) pyrrolidine-2-carboxylate and 0.9 g of benzyl 2-(3-isocyanatophenyl)propionate (form B) in 50 cm³ of tetrahydrofuran. After treatment, there is obtained 0.4 g of tert-butyl (2R*,4S*,5R*)-1-{2-[3-(3-(1-(benzyloxycarbonyl)ethyl (form B))phenyl)-ureido]acetyl}-5-(2-fluorophenyl)-4-(phenylsulphonyl)pyrrolidine-2-carboxylate in the form of a foam used as is in the subsequent syntheses.

C tert-Butyl (2R*,4S*,5R*)-1-(2-aminoacetyl)-5-(2-fluorophenyl)-4-(phenylsulphonyl)pyrrolidine-2-carboxylate can be prepared as described in Example 16C, but from 4.5 g of tert-butyl (2R*,4S*,5R*)-1-[2-(tert-butoxycarbonylamino)acetyl]-5-(2-fluorophenyl)-4-(phenylsulphonyl)pyrrolidine-2-carboxylate and 1.15 cm³ of iodotrimethylsilane in 240 cm³ of chloroform. After treatment, there are obtained 3.75 g of tert-butyl (2R*,4S*,5R*)-1-(2-aminoacetyl)-5-(2-fluorophenyl)-4-(phenylsulphonyl)pyrrolidine-2-carboxylate in the form of an oil used as is in the subsequent syntheses.

D tert-Butyl (2R*,4S*,5R*)-1-[2-(tert-butoxycarbonylamino)acetyl]-5-(2-fluorophenyl)-4-(phenylsulphonyl)pyrrolidine-2-carboxylate can be prepared in the following way: 11.35 g of tert-butyl (2RS,4SR,5RS)-1-[2-(tert-butoxycarbonylamino)acetyl]-5-(2-fluorophenyl)-4-(phenylsulphonyl)pyrrolidine-2-carboxylate are separated by high performance liquid chromatography in 37 injections on 400 g of support consisting of silica coated with cellulose tris(3,5-dimethylphenyl)carbamate prepared according to J. Amer. Chem. Soc., 106, 5357 (1984) and contained in a column with a length of 23 cm and a diameter of 6 cm with, as mobile phase, a 95/5 hexane/ethanol mixture at a flow rate of 40 cm³/minute, the laevorotatory and then the dextrorotatory enantiomer being successively eluted. The fractions containing each of the two enantiomers are combined and concentrated under reduced pressure. There are thus obtained:

5.25 g of tert-butyl (2R*,4S*,5R*)-(–)-1-[2-(tert-butoxycarbonylamino)acetyl]-5-(2-fluorophenyl)-4-(phenylsulphonyl)pyrrolidine-2-carboxylate, the optical rotation of which is $[\alpha]_D^{20}=-7.5°$ (c=1.0, methanol), then 4.76 g of tert-butyl (2R*,4S*,5R*)-(+)-1-[2-(tert-butoxycarbonylamino)acetyl]-5-(2-fluorophenyl)-4-(phenylsulphonyl)pyrrolidine-2-carboxylate, the optical rotation of which is $[\alpha]_D^{20}=+7.2°$ (c=0.72, methanol).

E tert-Butyl (2RS,4SR,5RS)-1-[2-(tert-butoxycarbonylamino)acetyl]-5-(2-fluorophenyl)-4-(phenylsulphonyl)pyrrolidine-2-carboxylate can be prepared as described in Example 16D, but from 16 g of tert-butyl (2RS,4SR,5RS)-5-(2-fluorophenyl)-4-(phenylsulphonyl) pyrrolidine-2-carboxylate, 6.9 g of 2-(tert-butoxycarbonylamino)acetic acid and 8.14 g of N,N'-dicyclohexylcarbodiimide in 400 cm³ of acetonitrile. After treatment, there are obtained 18 g of tert-butyl (2RS,4SR,5RS)-1-[2-(tert-butoxycarbonylamino)acetyl]-5-(2-fluorophenyl)-4-(phenylsulphonyl)pyrrolidine-2-carboxylate, melting at 134° C.

F Benzyl 2-(3-isocyanatophenyl)propionate (form B) can be prepared as in Example 17C, but from 2.85 g of benzyl (+)-2-(3-aminophenyl)propionate, 1.48 cm³ of trichloromethyl chloroformate and 0.24 g of charcoal. There are thus obtained 3.1 g of benzyl 2-(3-isocyanatophenyl)propionate (form B) in the form of an oil used as is in the subsequent syntheses.

G Benzyl (+)-2-(3-aminophenyl)propionate can be prepared in the following way: 75 g of ammonium chloride and 37.0 g of zinc powder are added to a solution of 8.0 g of benzyl (+)-2-(3-nitrophenyl)propionate in a mixture of 35 cm³ of methanol and 300 cm³ of water. The reaction mixture is heated at reflux for one hour, then cooled to a temperature in the region of 0° C. and filtered. The filtrate is extracted with three times 200 cm³ of diethyl ether. The organic phases are combined, washed successively with 100 cm³ of water and then 100 cm³ of a saturated aqueous sodium chloride solution, dried over magnesium sulphate and concentrated under reduced pressure. There are thus obtained 6.7 g of benzyl (+)-2-(3-aminophenyl)propionate in the form of a yellow oil used as is in the subsequent syntheses.

H Benzyl (+)-2-(3-nitrophenyl)propionate can be prepared in the following way: 4.72 cm³ of oxalyl chloride are added to a mixture containing 9.75 g of (+)-2-(3-nitrophenyl)propionic acid and 0.5 cm³ of N,N-dimethylformamide in 100 cm³ of 1,2-dichloroethane. The reaction mixture is stirred for three hours at a temperature in the region of 25° C. and then 5.4 g of benzyl alcohol are added. Stirring is continued for 12 h at this same temperature and then the reaction mixture is washed successively with 2 times 200 cm³ of saturated aqueous sodium hydrogencarbonate solution, 100 cm³ of water and 100 cm³ of a saturated aqueous sodium chloride solution. The organic phases are combined, washed successively with 100 cm³ of water and then 100 cm³ of a saturated aqueous sodium chloride solution, dried over magnesium sulphate and concentrated under reduced pressure. The residue is purified by chromatography on silica [eluent: ethyl acetate/cyclohexane (30/70 by volume)]. The fractions containing the expected product are combined and concentrated under reduced pressure. There are thus obtained 11.5 g of benzyl (+)-2-(3-nitrophenyl)propionate in the form of a yellow oil used as is in the subsequent syntheses.

I (+)-2-(3-Nitrophenyl)propionic acid can be prepared in the following way: a solution of 21.5 g of 2-(3-nitrophenyl)-N-[(R)-2-hydroxy-1-phenylethyl]propionamide (form B) in a mixture of 450 cm³ of 1,4-dioxane and 450 cm³ of a 4N aqueous hydrochloric acid solution is heated at a temperature in the region of 80° C. for five hours and then stirred for twelve hours at a temperature in the region of 20° C. The reaction mixture is concentrated by half by evaporation under reduced pressure, diluted by addition of 500 cm³ of distilled water and extracted with two times 500 cm³ of diethyl ether. The organic phases are combined, washed successively with three times 250 cm³ of water and then 250 cm³ of a saturated aqueous sodium chloride solution, dried over magnesium sulphate and concentrated under reduced pressure. There are thus obtained 14 g of (+)-2-(3-nitrophenyl)propionic acid (form B) in the form of a cream solid used as is in the subsequent syntheses.

J 2-(3-Nitrophenyl)-N-[(R)-2-hydroxy-1-phenylethyl] propionamide (form B) can be prepared in the following way: 17.2 cm³ of oxalyl chloride are slowly added to a mixture containing 39.0 g of (RS)-2-(3-nitrophenyl) propionic acid and 0.5 cm³ of N,N-dimethylformamide in 400 cm³ of 1,2-dichloroethane. The reaction mixture is stirred for three hours at a temperature in the region of 20° C. and than concentrated under reduced pressure. The residue is dissolved in 150 cm³ of 1,2-dichloroethane and added to a solution of 27.4 g of (R)-2-phenylglycinol, the temperature of the reaction mixture being maintained below 10° C. The reaction mixture is stirred for twelve hours at a temperature in the region of 20° C. and is then washed successively with 1000 cm³ of distilled water, 500 cm³ of a normal aqueous hydrochloric acid solution, two times 500 cm³ of distilled water and 500 cm³ of a saturated aqueous sodium chloride solution. The organic phase is dried over magnesium sulphate and concentrated under reduced pressure. The two diastereoisomers obtained are separated by chromatography on silica [eluent: methylene chloride/ethyl acetate (70/30 by volume)]. The fractions containing each of the two diastereoisomers are combined and concentrated under reduced pressure. There are thus obtained 21.0 g of 2-(3-nitrophenyl)-N-[(R)-2-hydroxy-1-phenylethyl] propionamide (form A) (first solution product), melting at 135° C., and 19.0 g of 2-(3-nitrophenyl)-N-[(R)-2-hydroxy-1-phenylethyl]propionamide (form B) (second solution product), melting at 150° C. (RS)-2-(3-Nitrophenyl) propionic acid can be prepared according to the method described by E. Felder et al., J. Med. Chem., 13, 559 (1970).

EXAMPLE 38

A The reaction is carried out in a way analogous to that described in Example 2A, but from 1.95 g of tert-butyl (2R*,4S*,5R*)-1-{2-[3-(3-((S)-1-benzyloxycarbonyl-1-methoxymethyl)phenyl)ureido]acetyl}-5-(2-fluorophenyl)-4-(phenylsulphonyl)pyrrolidine-2-carboxylate and 0.2 g of 10% palladium-on-charcoal in 100 cm³ of ethanol. After treatment, there is obtained 0.72 g of (S)-(2R*,4S*,5R*)-2-{3-[3-(2-2-tert-butoxycarbonyl-5-(2-fluorophenyl)-4-phenylsulphonyl-1-pyrrolidinyl)-2-oxoethyl)ureido] phenyl}-2-methoxyacetic acid [$R_f$=0.27; eluent: methylene chloride/methanol (90/10)].

B tert-Butyl (2R*,4S*,5R*)-1-{2-[3-(3-((S)-1-benzyloxycarbonyl-1-methoxymethyl)phenyl)ureido]acetyl}-5-(2-fluorophenyl)-4-(phenylsulphonyl)pyrrolidine-2-carboxylate can be prepared as described in Example 17B, but from 2.95 g of tert-butyl (2R*,4S*,5R*)-1-(2-aminoacetyl)-5-(2-fluorophenyl)-4-(phenylsulphonyl)pyrrolidine-2-carboxylate and 2.1 g of benzyl (S)-2-(3-isocyanatophenyl)-2-methoxyacetate in 100 cm³ of tetrahydrofuran. After treatment, there are obtained 2.05 g of benzyl (S)-2-{3-[3-(2-((2R*,4S*,5R*)-2-tert-butoxycarbonyl-5-(2-fluorophenyl)-4-phenylsulphonyl-1-pyrrolidinyl)-2-oxoethyl)ureido]phenyl}-2-methoxyacetate in the form of a foam used as is in the subsequent syntheses.

C Benzyl (S)-2-(3-isocyanatophenyl)-2-methoxyacetate can be prepared as in Example 17C, but from 2.6 g of benzyl (S)-2-(3-aminophenyl)-2-methoxyacetate, 1.16 cm³ of trichloromethyl chloroformate and 0.4 g of charcoal in 75 cm³ of toluene. There are thus obtained 3 g of benzyl (S)-2-(3-isocyanatophenyl)-2-methoxyacetate in the form of an oil used as is in the subsequent syntheses.

D Benzyl (S)-2-(3-aminophenyl)-2-methoxyacetate can be prepared as in Example 37G, but from 8 g of benzyl (S)-2-methoxy-2-(3-nitrophenyl)acetate, 72.7 g of ammonium chloride and 34.6 g of zinc powder in a mixture of 35 cm³ of methanol and 350 cm³ of distilled water. After treatment, there are obtained 2.6 g of benzyl (S)-2-(3-aminophenyl)-2-methoxyacetate in the form of a yellow oil used as is in the subsequent syntheses.

E Benzyl (S)-2-methoxy-2-(3-nitrophenyl)acetate can be prepared as described in Example 37H, but from 7.1 g of (S)-2-methoxy-2-(3-nitrophenyl)acetic acid, 4.25 cm² of oxalyl chloride, 0.5 cm³ of N,N-dimethylformamide and 6.0 cm³ of benzyl alcohol in 120 cm³ of 1,2-dichloroethane. After treatment, there are obtained 11.5 g of benzyl (S)-2-methoxy-2-(3-nitrophenyl)acetate in the form of a yellow oil used as is in the subsequent syntheses.

F (S)-2-Methoxy-2-(3-nitrophenyl)acetic acid can be prepared as described in Example 37I, but from 16.5 g of (S)-2-methoxy-2-(3-nitrophenyl)-N-[(R)-2-hydroxy-1-phenylethyl]acetamide and 200 cm³ of a 4N aqueous hydrochloric acid solution in 260 cm³ of 1,4-dioxane. After treatment, there are obtained 9.5 g of (S)-2-methoxy-2-(3-nitrophenyl)acetic acid, melting at 112° C.

G (S)-2-Methoxy-2-(3-nitrophenyl)-N-[(R)-2-hydroxy-1-phenylethyl]acetamide can be prepared as described in Example 37J, but from 42.2 g of (RS)-2-methoxy-2-(3-nitrophenyl)acetic acid, 0.5 cm³ of N,N-dimethylformamide and 17.2 cm³ of oxalyl chloride in 200 cm³ of 1,2-dichloroethane and then 27.4 g of (R)-2-phenylglycinol in 200 cm³ of 1,2-dichloroethane. After treatment, there are obtained 20 g of (S)-2-methoxy-2-(3-nitrophenyl)-N-[(R)-2-hydroxy-1-phenylethyl]acetamide in the form of a solid used as is in the subsequent syntheses. (RS)-2-Methoxy-2-(3-nitrophenyl)acetic acid can be prepared according to the method described by A. Takeda, Contribs. Boyce Thompson Institute, 20, 197–203 (1959).

EXAMPLE 39

A The reaction is carried out in a way analogous to that described in Example 2B, but from 3.05 g of 2-tert-butyl 4-methyl (2RS,4RS,5SR)-5-phenylpyrrolidine-2,4-dicarboxylate, 2.32 g of (RS)-2-(2-indolylcarbonylamino)propionic acid and 2.1 g of N,N'-dicyclohexylcarbodiimide in 50 cm³ of acetonitrile. After treatment, there are obtained 2.35 g of 2-tert-butyl 4-methyl (2RS,4RS,5SR)-1-[2-(2-indolylcarbonylamino)propionyl-(form A)]-5-phenylpyrrolidine-2,4-dicarboxylate, melting at 182° C., and 1.38 g of 2-tert-butyl 4-methyl (2RS,4RS,5SR)-1-[2-(2-indolylcarbonylamino)propionyl-(form B)]-5-phenylpyrrolidine-2,4-dicarboxylate, melting at 207° C.

B (RS)-2-(2-Indolylcarbonylamino)propionic acid can be prepared in the following way: a solution of 9.75 g of 2-indolecarboxylic acid chloride in 70 cm³ of 1,4-dioxane is added, at a temperature between 5° and 10° C., to a solution of 4.4 g of (RS)-alanine and 14.34 g of potassium carbonate in 90 cm³ of distilled water. The mixture is stirred for twenty hours at a temperature in the region of 20° C., diluted by addition of 50 cm³ of distilled water and than acidified to a pH in the region of 1 by addition of a normal aqueous hydrochloric acid solution. The solid which precipitates is separated by filtration, rinsed with two times 25 cm³ of distilled water, drained and dried under reduced pressure at a temperature in the region of 40° C. There are thus obtained 8.3 g of (RS)-2-(2-indolylcarbonylamino)propionic acid, melting at 240° C.

EXAMPLE 40

A The reaction is carried out in a way analogous to that described in Example 3, but from 1.15 g of 2-tert-butyl 4-methyl (2RS,4RS,5SR)-1-[2-(2-indolylcarbonylamino)propionyl-(form A)]-5-phenylpyrrolidine-2,4-dicarboxylate (form A) and 0.12 g of potassium hydroxide in 40 cm³ of distilled water and 60 cm³ of methanol. After treatment, there is obtained 0.46 g of 2-tert-butyl hydrogen (2RS,4SR,5SR)-1-[2-(2-indolylcarbonylamino)propionyl-(form A)]-5-phenylpyrrolidine-2,4-dicarboxylate (form A) [R$_f$=0.22; eluent: methylene chloride/methanol (90/10)].

EXAMPLE 41

A The reaction is carried out in a way analogous to that described in Example 3, but from 1.5 g of tert-butyl (2RS,4SR,5SR)-1-{2-[3-(3-(ethoxycarbonyl)phenyl)ureido]acetyl}-5-(2-fluorophenyl)-4-(morpholinocarbonyl)pyrrolidine-2-carboxylate and 2.4 cm³ of a normal aqueous potassium hydroxide solution in a mixture of 12.5 cm³ of distilled water and 50 cm³ of methanol. After treatment, there is obtained 0.28 g of (2RS,4SR,5SR)-3-{3-[2-(2-tert-butoxycarbonyl-5-(2-fluorophenyl)-4-(morpholinocarbonyl)-1-pyrrolidine)-2-oxoethyl]ureido}benzoic acid [R$_f$=0.195 eluent: methylene chloride/methanol (90/10)].

B tert-Butyl (2RS,4SR,5SR)-1-{2-[3-(3-(ethoxycarbomyl)phenyl)ureido]acetyl}-5-(2-fluorophenyl)-4-(morpholinocarbonyl)pyrrolidine-2-carboxylate can be prepared as described in Example 17B, but from 1.7 g of tert-butyl (2RS,4SR,5SR)-1-(2-aminoacetyl)-5-(2-fluorophenyl)-4-(morpholinocarbonyl)pyrrolidine-2-carboxylate and 0.75 g of ethyl 3-isocyanatobenzoate in 80 cm³ of tetrahydrofuran. After treatment, there are obtained 1.5 g of tert-butyl (2RS,4SR,5SR)-1-{2-[3-(3-(ethoxycarbonyl)phenyl)ureido]acetyl}-5-(2-fluorophenyl)-4-(morpholinocarbonyl)pyrrolidine-2-carboxylate in the form of a foam used as is in the subsequent syntheses.

C tert-Butyl (2RS,4SR,5SR)-1-(2-aminoacetyl)-5-(2-fluorophenyl)-4-(morpholinocarbonyl)pyrrolidine-2-carboxylate can be prepared as described in Example 16C, but from 2.6 g of tert-butyl (2RS,4SR,5SR)-1-[2-(tert-butoxycarbonylamino)acetyl]-5-(2-fluorophenyl)-4-(morpholinocarbonyl)pyrrolidine-2-carboxylate and 0.93 cm³ of iodotrimethylsilane in 20 cm³ of chloroform. After treatment, there are obtained 1.7 g of tert-butyl (2RS,4SR,5SR)-1-(2-aminoacetyl)-5-(2-fluorophenyl)-4-

(morpholinocarbonyl)pyrrolidine-2-carboxylate in the form of a foam used as is in the subsequent syntheses.

D tert-Butyl (2RS,4SR,5SR)-1-[2-(tert-butoxycarbonylamino)acetyl]-5-(2-fluorophenyl)-4-(morpholinocarbonyl)pyrrolidine-2-carboxylate can be prepared as described in Example 20D, but from 3.73 g of 2-tert-butyl hydrogen (2RS,4SR,5SR)-1-[2-(tert-butoxycarbonylamino)acetyl]-5-(2-fluorophenyl) pyrrolidine-2,4-dicarboxylate, 0.70 g of morpholine and 1.65 g of N,N'-dicyclohexylcarbodiimide in 120 cm³ of acetonitrile. After treatment, there are obtained 2.65 g of tert-butyl (2RS,4SR,5SR)-1-[2-(tert-butoxycarbonylamino) acetyl]-5-(2-fluorophenyl)-4-(morpholinocarbonyl) pyrrolidine-2-carboxylate in the form of a foam used as is in the subsequent syntheses.

E 2-tert-Butyl hydrogen (2RS,4SR,5SR)-1-[2-(tert-butoxycarbonylamino)acetyl]-5-(2-fluorophenyl) pyrrolidine-2,4-dicarboxylate can be prepared in a way analogous to that described in Example 20E, but from 24 g of 2-tert-butyl 4-methyl (2RS,4RS,5SR)-1-[2-(tert-butoxycarbonylamino)acetyl]-5-(2-fluorophenyl) pyrrolidine-2,4-dicarboxylate and 50 cm³ of a normal aqueous sodium hydroxide solution in a mixture of 750 cm³ of methanol and 200 cm³ of water. After treatment, there are obtained 21.4 g of -tert-butyl hydrogen (2RS,4SR,5SR)-1-[2-(tert-butoxycarbonylamino)acetyl]-5-(2-fluorophenyl) pyrrolidine-2,4-dicarboxylate in the form of a solid used as is in the subsequent syntheses.

F 2-tert-Butyl 4-methyl (2RS,4RS,5SR)-1-[2-(tert-butoxycarbonylamino)acetyl]-5-(2-fluorophenyl) pyrrolidine-2,4-dicarboxylate can be prepared in a way analogous to that described in Example 16D, but from 29 g of 2-tert-butyl 4-methyl (2RS,4RS,5SR)-5-(2-fluorophenyl) pyrrolidine-2,4-dicarboxylate, 15.7 g of 2-(tert-butoxycarbonylamino)acetic acid and 18.5 g of N,N'-dicyclohexylcarbodiimide in 200 cm³ of acetonitrile. After treatment, there are obtained 34 g of 2-tert-butyl 4-methyl (2RS,4RS,5SR)-1-[2-(tert-butoxycarbonylamino)acetyl]-5-(2-fluorophenyl)pyrrolidine-2,4-dicarboxylate, melting at 142° C.

EXAMPLE 42

A The reaction is carried out in a way analogous to that described in Example 3, but from 1.75 g of tert-butyl (2RS,4SR,5SR)-1-{2-[3-(3-(ethoxycarbonyl)phenyl)ureido]acetyl}-4-diethylaminocarbonyl-5-(2-fluorophenyl) pyrrolidine-2-carboxylate and 2.8 cm³ of a normal aqueous potassium hydroxide solution in a mixture of 15 cm³ of distilled water and 65 cm³ of methanol. After treatment, there is obtained 0.50 g of (2RS,4SR,5SR)-3-{3-[2-(2-tert-butoxycarbonyl-4-diethylaminocarbonyl-5-(2-fluorophenyl)-1-pyrrolidinyl)-2-oxoethyl]ureido}-benzoic acid, melting at 150° C.

B tert-Butyl (2RS,4SR,5SR)-1-{2-[3-(3-(ethoxycarbonyl) phenyl)ureido]acetyl}-4-diethylaminocarbonyl-5-(2-fluorophenyl)pyrrolidine-2-carboxylate can be prepared as described in Example 17B, but from 2.7 g of tert-butyl (2RS,4SR,5SR)-1-(2-aminoacetyl)-4-diethylaminocarbonyl-5-(2-fluorophenyl)pyrrolidine-2-carboxylate and 1.21 g of ethyl 3-isocyanatobenzoate in 80 cm³ of tetrahydrofuran. After treatment, there are obtained 1.75 g of tert-butyl (2RS,4SR,5SR)-1-{2-[3-(3-(ethoxycarbonyl)phenyl)ureido]acetyl}-4-diethylaminocarbonyl-5-(2-fluorophenyl)pyrrolidine-2-carboxylate in the form of a foam used as is in the subsequent syntheses.

C tert-Butyl (2RS,4SR,5SR)-1-(2-aminoacetyl)-4-diethylaminocarbonyl-5-(2-fluorophenyl)pyrrolidine-2-carboxylate can be prepared as described in Example 16C, but from 4.5 g of tert-butyl (2RS,4SR,5SR)-1-[2-(tert-butoxycarbonylamino)acetyl]-4-diethylaminocarbonyl-5-(2-fluorophenyl)pyrrolidine-2-carboxylate and 1.2 cm³ of iodotrimethylsilane in 180 cm³ of chloroform. After treatment, there are obtained 2.7 g of tert-butyl (2RS,4SR, 5SR)-1-(2-aminoacetyl)-4-diethylaminocarbonyl-5-(2-fluorophenyl)pyrrolidine-2-carboxylate in the form of a foam used as is in the subsequent syntheses.

D tert-Butyl (2RS,4SR,5SR)-1-[2-(tert-butoxycarbonylamino)acetyl]-4-diethylaminocarbonyl-5-(2-fluorophenyl)pyrrolidine-2-carboxylate can be prepared as described in Example 20D, but from 4.66 g of 2-tert-butyl hydrogen (2RS,4SR,5SR)-1-[2-(tert-butoxycarbonylamino) acetyl]-5-(2-fluorophenyl)pyrrolidine-2,4-dicarboxylate, 0.73 g of diethylamine, 10 mg of 4-dimethylaminopyridine and 1.78 g of N,N'-dicyclohexylcarbodiimide in 120 cm³ of acetonitrile. After treatment, there are obtained 4.5 g of tert-butyl (2RS,4SR,5SR)-1-[2-(tert-butoxycarbonylamino) acetyl]-4-diethylaminocarbonyl-5-(2-fluorophenyl) pyrrolidine-2-carboxylate in the form of a foam used as is in the subsequent syntheses.

EXAMPLE 43

A The reaction is carried out in a way analogous to that described in Example 3, but from 3.1 g of 2-tert-butyl 4-methyl (2RS,4RS,5SR)-1-{2-[3-(3-(methoxycarbonylmethyl)phenyl)ureido]acetyl}-5-phenyl-2-methylpyrrolidine-2,4-dicarboxylate and 0.62 g of potassium hydroxide in a mixture of 100 cm³ of distilled water and 150 cm³ of methanol. After treatment, there is obtained 0.85 g of (2RS,4RS,5SR)-3-{3-[2-(2-tert-butoxycarbonyl-4-methoxycarbonyl-2-methyl-5-phenyl-1-pyrrolidinyl)-2-oxoethyl]ureido}phenylacetic acid [$R_f$=0.29; eluent: methylene chloride/methanol (90/10)].

B 2-tert-Butyl 4-methyl (2RS,4RS,5SR)-1-{2-[3-(3-(methoxycarbonylmethyl)phenyl)ureido]acetyl}-5-phenyl-2-methylpyrrolidine-2,4-dicarboxylate can be prepared as described in Example 2B, but from 5.2 g of 2-tert-butyl 4-methyl (2RS,4RS,5SR)-2-methyl-5-phenylpyrrolidine-2,4-dicarboxylate, 4.34 g of 2-{3-[3-(methoxycarbonylmethyl)phenyl]ureido}acetic acid and 3.36 g of N,N'-dicyclohexylcarbodiimide in 90 cm³ of acetonitrile. After treatment, there are obtained 3.1 g of 2-tert-butyl 4-methyl (2RS,4RS,5SR)-1-{2-[3-(3-(methoxycarbonylmethyl)phenyl)ureido]acetyl}-5-phenyl-2-methylpyrrolidine-2,4-dicarboxylate in the form of an amorphous solid used as is in the subsequent syntheses.

C 2-tert-Butyl 4-methyl (2RS,4RS,5SR)-2-methyl-5-phenylpyrrolidine-2,4-dicarboxylate can be prepared as described in Example 2C, but from 4.5 g of tert-butyl 2-(benzylideneamino)propionate, 1.74 cm³ of methyl acrylate, 4.84 g of silver acetate and 3.26 cm³ of triethylamine in 200 cm³ of acetonitrile. After treatment, there are obtained 5.2 g of 2-tert-butyl 4-methyl (2RS,4RS,5SR)-2-methyl-5-phenylpyrrolidine-2,4-dicarboxylate in the form of an oil used as is in the subsequent syntheses.

D tert-Butyl-2-(benzylideneamino)propionate can be prepared as described in Example 2D, but from 2.03 cm³ of benzaldehyde, 3.63 g of tert-butyl alaninate hydrochloride, 3 g of 4 Å sieve and 2.8 cm³ of triethylamine in 50 cm³ of dichloromethane. After treatment, there are obtained 4.5 g of tert-butyl 2-(benzylideneamino)propionate in the form of an oil used as is in the subsequent syntheses.

EXAMPLE 44

A The reaction is carried out in a way analogous to that described in Example 2A, but from 2.83 g of (2RS,4SR, 5RS)-1-{2-[3-(3-(benzyloxycarbonylmethyl)phenyl)ureido] acetyl}-5-(2-fluorophenyl)-2-(1,2,3,4-tetrahydro-1-quinolylcarbonyl)-4-(phenylsulphonyl)pyrrolidine and 0.36 g of 10% palladium-on-charcoal in 150 cm³ of ethanol. After treatment, there are obtained 1.67 g of (2RS,4RS,5SR)-3-{3-[2-(5-(2-fluorophenyl)-2-(1,2,3,4-tetrahydro-1-quinolylcarbonyl)-4-(phenylsulphonyl)-1-pyrrolidinyl)-2-oxoethyl]ureido}phenylacetic acid [$R_f$=0.49; eluent: methylene chloride/methanol (90/10)].

B (2RS,4SR,5RS)-1-{2-[3-(3-(Benzyloxycarbonylmethyl)phenyl)ureido]acetyl}-5-(2-fluorophenyl)-4-phenylsulphonyl-2-(1,2,3,4-tetrahydro-1-quinolylcarbonyl)pyrrolidine can be prepared as described in Example 2B, but from 2.3 g of (2RS,4RS,5RS)-5-(2-fluorophenyl)-4-phenylsulphonyl-2-(1,2,3,4-tetrahydro-1-quinolylcarbonyl)pyrrolidine, 1.69 g of 2-{3-[3-(benzyloxycarbonylmethyl)phenyl]ureido}acetic acid and 1.02 g of N,N'-dicyclohexylcarbodiimide in 50 cm³ of acetonitrile. After treatment, there are obtained 2.83 g of (2RS,4SR,5RS)-1-{2-[3-(3-(benzyloxycarbonylmethyl) phenyl)ureido]acetyl}-5-(2-fluorophenyl)-4-phenylsulphonyl-2-(1,2,3,4-tetrahydro-1-quinolylcarbonyl) pyrrolidine in the form of an amorphous solid used as is in the subsequent syntheses.

C (2RS,4RS,5RS)-5-(2-Fluorophenyl)-4-phenylsulphonyl-2-(1,2,3,4-tetrahydroquinolyl) carbonylpyrrolidine can be prepared as described in Example 2C, but from 3.68 g of 1-[2-(2-fluorobenzylideneamino)acetyl]-1,2,3,4-tetrahydroquinoline, 2.1 g of phenyl vinyl sulphone, 3.12 g of silver acetate and 1.75 cm³ of triethylamine in 100 cm³ of acetonitrile. After treatment, there are obtained 2.3 g of (2RS,4SR,5RS)-5-(2-fluorophenyl)-4-phenylsulphonyl-2-(1,2,3,4-tetrahydro-1-quinolylcarbonyl)pyrrolidine in the form of a foam used as is in the subsequent syntheses.

D 1-[2-(2-Fluorobenzylideneamino)acetyl]-1,2,3,4-tetrahydroquinoline can be prepared as described in Example 2D, but from 1.53 cm³ of 2-fluorobenzaldehyde, 3.95 g of 1-(2-aminoacetyl)-1,2,3,4-tetrahydroquinoline hydrobromide, 2.2 g of 4 Å sieve and 2.05 cm³ of triethylamine in 50 cm³ of dichloromethane. After treatment, there are obtained 3.68 g of 1-[2-(2-fluorobenzylideneamino) acetyl]-1,2,3,4-tetrahydroquinoline in the form of an oil used as is in the subsequent syntheses.

E 1-(2-Aminoacetyl)-1,2,3,4-tetrahydroquinoline hydrobromide can be prepared in the following way: a solution of 5.08 g of 1-(2-bromoacetyl)-1,2,3,4-tetrahydroquinoline in 150 cm³ of a 7N methanolic ammonia solution is stirred for eight hours at a temperature in the region of 20° C. The reaction mixture is then concentrated under reduced pressure and the residue crystallized from 150 cm³ of acetonitrile. The solid is separated by filtration end dried under reduced pressure. There are thus obtained 3.95 g of 1-(2-aminoacetyl)-1,2,3,4-tetrahydroquinoline hydrobromide, melting at 241° C.

F 1-(2-Bromoacetyl)-1,2,3,4-tetrahydroquinoline can be prepared in the following way: a solution of 27.5 cm³ of bromoacetyl bromide in 30 cm³ of dichloromethene is added dropwise, at a temperature in the region of −5° C., to a solution of 39.96 g of 1,2,3,4-tetrahydroquinoline in a mixture of 46.8 cm³ of triethylamine end 195 cm³ of dichloromethene. The reaction mixture is stirred for two hours at a temperature in the region of 20° C. end then poured into 300 cm³ of distilled water. The organic phase is separated by settling, washed with three times 100 cm³ of a saturated aqueous sodium chloride solution, dried over magnesium sulphate end concentrated under reduced pressure. The residue is taken up in 300 cm³ of diisopropyl ether and filtered. The filtrate is concentrated under reduced pressure. There are thus obtained 67.48 g of 1-(2-bromoacetyl)-1,2,3,4-tetrahydroquinoline in the form of an oil used as is in the subsequent syntheses.

EXAMPLE 45

A The reaction is carried out in a way analogous to that described in Example 3, but from 3.4 g of methyl (2RS, 4RS,5SR)-5-(2-fluorophenyl)-1-{2-[3-(3-(methoxycarbonylmethyl)phenyl)ureido]acetyl}2-(1,2,3,4-tetrahydro-1-quinolylcarbonyl)pyrrolidine-4-carboxylate and 0.61 g of potassium hydroxide in a mixture of 30 cm³ of distilled water and 50 cm³ of methanol. After treatment, there are obtained 2.5 g of (2RS,4SR,5SR)-1-{2-[3-(3-(carboxymethyl)phenyl)ureido]acetyl}-5-(2-fluorophenyl)-2-(1,2,3,4-tetrahydro-1-quinolylcarbonyl)pyrrolidine-4-carboxylic acid [$R_f$=0.36; eluent: methylene chloride/methanol (90/10)].

B Methyl (2RS,4RS,5SR)-5-(2-fluorophenyl)-1-{2-[3-(3-(methoxycarbonylmethyl)phenyl)ureido]acetyl}2-(1,2,3,4-tetrahydro-1-quinolylcarbonyl)pyrrolidine-4-carboxylate can be prepared as described in Example 2B, but from 3.23 g of methyl (2RS,4RS,5SR)-5-(2-fluorophenyl)-2-(1,2,3,4-tetrahydro-1-quinolylcarbonyl)pyrrolidine-4-carboxylate, 2.25 g of 2-[3-[3-(methoxycarbonylmethyl)phenyl] ureido}acetic acid and 1.75 g of N,N'-dicyclohexylcarbodiimide in 90 cm³ of acetonitrile. After treatment, there are obtained 3.6 g of methyl (2RS,4RS, 5SR)-5-(2-fluorophenyl)-2-(1,2,3,4-tetrahydro-1-quinolylcarbonyl)-1-{2-[3-(3-(methoxycarbonylmethyl) phenyl)ureido]acetyl}pyrrolidine-4-carboxylate in the form of an amorphous solid used as is in the subsequent syntheses.

C Methyl (2RS,4RS,5SR)-5-(2-fluorophenyl)-2-(1,2,3,4-tetrahydro-1-quinolylcarbonyl)pyrrolidine-4-carboxylate can be prepared as described in Example 2C, but from 4.86 g of 1-[2-(2-fluorobenzylideneamino)acetyl]-1,2,3,4-tetrahydroquinoline, 1.48 cm³ of methyl acrylate, 4.11 g of silver acetate and 2.77 cm³ of triethylamine in 175 cm³ of acetonitrile. After treatment, there are obtained 5.55 g of methyl (2RS,4RS,5SR)-5-(2-fluorophenyl)-2-(1,2,3,4-tetrahydro-1-quinolylcarbonyl)pyrrolidine-4-carboxylate in the form of an oil used as is in the subsequent syntheses.

EXAMPLE 46

A The reaction is carried out in a way analogous to that described in Example 16B, but from 2.3 g of tert-butyl (2RS,4SR,5RS)-1-(2-aminoacetyl)-5-(2-fluorophenyl)-4-(phenylsulphonyl)pyrrolidine-2-carboxylate, 0.9 g of N,N'-carbonyldiimidazole and 0.81 g of 5-(3-aminophenyl) tetrazole in 70 cm³ of 1,2-dichloroethane. After treatment, there is obtained 0.6 g of (2RS,4SR,5RS)-5-{3-[3-(2-(2-tert-butoxycarbonyl-5-(2-flurophenyl)-4-phenylsulphonyl-1-pyrrolidinyl)-2-oxoethyl)ureido]phenyl}tetrazole in the sodium salt form [$R_f$0.17; eluent: methylene chloride/methanol (90/10)].

B tert-Butyl (2RS,4SR,5RS)-1-(2-aminoacetyl)-5-(2-fluorophenyl)-4-(phenylsulphonyl)pyrrolidine-2-carboxylate can be prepared as described in Example 16C, but from 2.82 g of tert-butyl (2RS,4SR,5RS)-1-[2-(tert-butoxycarbonylamino)acetyl]-5-(2-fluorophenyl)-4-

(phenylsulphonyl)pyrrolidine-2-carboxylate and 0.72 cm³ of iodotrimethylsilane in 50 cm³ of chloroform. After treatment, there are obtained 2.3 g of tert-butyl (2RS,4SR, 5RS)-1-(2-aminoacetyl)-5-(2-fluorophenyl)-4-(phenylsulphonyl)pyrrolidine-2-carboxylate in the form of a foam used as is in the subsequent syntheses. 5-(3-Aminophenyl)tetrazole can be prepared according to the method described in Patent Application EP 0,508,796 (Merck & Co Inc.).

EXAMPLE 47

A The reaction is carried out in a way analogous to that described in Example 3, but from 3.5 g of (2RS,4SR,5RS)-5-(2-fluorophenyl)-1-{2-[3-(3-(methoxycarbonylmethyl)phenyl)ureido]acetyl}-2-morpholinocarbonyl-4-(phenylsulphonyl)pyrrolidine and 0.3 g of potassium hydroxide in a mixture of 30 cm³ of distilled water and 50 cm³ of methanol. After treatment, there are obtained 2.45 g of (2RS,4SR,5RS)-3-{3-[2-(5-(2-fluorophenyl)-2-morpholinocarbonyl-4-phenylsulphonyl-1-pyrrolidinyl)-2-oxoethyl]ureido}phenylacetic acid [$R_f$=0.64; eluent: methylene chloride/methanol (80/20)].

B (2RS,4SR,5RS)-5-(2-Fluorophenyl)-1-{2-[3-(3-(methoxycarbonylmethyl)phenyl)ureido]acetyl}-2-morpholinocarbonyl-4-(phenylsulphonyl)pyrrolidine can be prepared as described in Example 2B, but from 2.1 g of (2RS,4SR,5RS)-S-(2-fluorophenyl)-2-morpholinocarbonyl-4-(phenylsulphonyl)pyrrolidine, 1.33 g of 2-{3-[3-(methoxycarbonylmethyl)phenyl]ureido}acetic acid and 1.03 g of N,N'-dicyclohexylcarbodiimide in 75 cm³ of acetonitrile. After treatment, there are obtained 3.56 g of (2RS,4SR,5RS)-5-(2-fluorophenyl)-1-{2-[3-(3-(methoxycarbonylmethyl)phenyl)ureido]acetyl}-2-morpholinocarbonyl -4-(phenylsulphonyl)pyrrolidine in the form of a foam used as is in the subsequent syntheses.

C (2RS,4SR,5RS)-5-(2-Fluorophenyl)-2-morpholinocarbonyl-4-(phenylsulphonyl)pyrrolidine can be prepared as described in Example 2C, but from 6 g of 4-[2-(2-fluorobenzylideneamino)acetyl]morpholine, 4.05 g of phenyl vinyl sulphone, 6 g of silver acetate and 4.05 cm³ of triethylamine in 200 cm³ of acetonitrile. After treatment, there are obtained 2.9 g of (2RS,4SR,5RS)-5-(2-fluorophenyl)-2-morpholinocarbonyl-4-(phenylsulphonyl)pyrrolidine in the form of an oil used as is in the subsequent syntheses.

D 4-[2-(2-Fluorobenzylidaneamino)acetyl]morpholine can be prepared as described in Example 2D, but from 5.3 cm³ of 2-fluorobenzaldehyde, 9.1 g of 4-(2-aminoacetyl)morpholine hydrochloride, 6 g of 4 Å seive and 7 cm³ of triethylamine in 150 cm³ of dichloromethane. After treatment, there are obtained 12 g of 4-[2-(2-fluorobenzylideneamino)acetyl]morpholine in the form of an oil used as is in the subsequent syntheses.

E 4-(2-Aminoacetyl)morpholine hydrochloride can be prepared as described in Example 44E, but from 16 g of 4-(chloroacetyl)morpholine in 140 cm³ of a 7N methanolic ammononia solution. After treatment, there are obtained 9.1 g of 4-(2-aminoacetyl)morpholine hydrochloride, melting at 158° C.

F 4-(Chloroacetyl)morpholine can be prepared in the following way: 25 cm³ of a 20% aqueous sodium hydroxide solution are added to a solution of 8.71 cm³ of morpholine in 50 cm³ of 1,2-dichloroethane. The mixture is cooled to a temperature in the region of −20° C. and then 9.9 cm³ of chloroacetyl chloride are added dropwise. The reaction mixture is stirred for two hours at a temperature in the region of −20° C. and then for twenty hours at a temperature in the region of 20° C. 100 cm³ of distilled water are then added and extraction is carried out with three times 100 cm³ of dichloromethane. The organic phases are combined, washed with three times 100 cm³ of a 3% aqueous hydrochloric acid solution, two times 100 cm³ of a 10% aqueous sodium hydrogencarbonate solution and two times 100 cm³ of a saturated aqueous sodium chloride solution, then dried over magnesium sulphate and concentrated under reduced pressure. There are thus obtained 16 g of 4-(chloroacetyl)morpholine in the form of an oil used as is in the subsequent syntheses.

EXAMPLE 48

A The reaction is carried out in a way analogous to that described in Example 3, but from 3.75 g of (2RS,4SR,5RS)-5-(2-flurophenyl)-2-isobutylcarbamoyl-1-{2-[3-(3-(methoxycarbonylmethyl)phenyl)ureido]acetyl}-4-(phenylsulphonyl)pyrrolidine and 0.32 g of potassium hydroxide in a mixture of 55 cm³ of distilled water and 140 cm³ of methanol. After treatment, there are obtained 1.84 g of (2RS,4SR,5RS)-3-{3-[2-(5-(2-fluorophenyl)-2-isobutylcarbamoyl-4-phenylsulphonyl-1-pyrrolidinyl)-2-oxoethyl]ureido}phenylacetic acid [$R_f$=0.73; eluent: methylene chloride/methanol (80/20)].

(2RS,4SR,5RS)-5-(2-Flurophenyl)-2-isobutylcarbamoyl-1-{2-[3-(3-(methoxycarbonylmethyl)phenyl)ureido]acetyl}-4-(phenylsulphonyl)pyrrolidine can be prepared as described in Example 2B, but from 2.3 g of (2RS,4SR,5RS)-5-(2-fluorophenyl)-2-isobutylcarbamoyl-4-(phenylsulphonyl)pyrrolidine, 1.5 g of 2-{3-[3-(methoxycarbonylmethyl)phenyl]ureido}acetic acid and 1.17 g of N,N'-dicyclohexylcarbodiimide in 100 cm³ of acetonitrile. After treatment, there are obtained 3.77 g of (2RS,4SR,5RS)-5-(2-flurophenyl)-2-isobutylcarbamoyl-1-{2-[3-(3-(methoxycarbonylmethyl)phenyl)ureido]acetyl}-4-(phenylsulphonyl)pyrrolidine in the form of a foam used as is in the subsequent syntheses.

C (2RS,4SR,5RS)-5-(2-Fluorophenyl)-2-isobutylcarbamoyl-4-(phenylsulphonyl)pyrrolidine can be prepared as described in Example 2C, but from 5.5 g of 2-(2-fluorobenzylidaneamino)-N-isobutylacetamide, 3.7 g of phenyl vinyl sulphone, 5.45 g of silver acetate and 3.7 cm³ of triethylamine in 200 cm³ of acetonitrile. After treatment, there are obtained 2.7 g of (2RS,4SR,5RS)-5-(2-fluorophenyl)-2-isobutylcarbamoyl-4-(phenylsulphonyl)pyrrolidine in the form of an oil used as is in the subsequent syntheses.

D 2-(2-Fluorobenzylideneamino)-N-isobutylacetamide can be prepared as described in Example 2D, but from 4.75 cm³ of 2-fluorobenzaldehyde, 7.5 g of 2-amino-N-isobutylacetamide hydrochloride, 6 g of 4 Å sieve and 6.3 cm³ of triethylamine in 150 cm³ of dichloromethane. After treatment, there are obtained 11 g of 2-(2-fluorobenzylideneamino)-N-isobutylacetamide in the form of an oil used as is in the subsequent syntheses.

E 2-Amino-N-isobutylacetamide hydrochloride can be prepared as described in Example 44E, but from 15 g of 2-chloro-N-isobutylacetamide in 140 cm³ of a 7N methanolic ammonia solution. After treatment, there are obtained 7.5 g of 2-amino-N-isobutylacetamide hydrochloride, melting at 154° C.

F 2-Chloro-N-isobutylacetamide can be prepared as described in Example 47F, but from 10.2 cm³ of isobutylamine, 9.9 cm³ of chloroacetyl chloride and 25 cm³ of a 20% aqueous sodium hydroxide solution in 50 cm³ of 1,2-dichloroethane. After treatment, there are obtained 15 g of 2-chloro-N-isobutylacetamide in the form of an oil used as is in the subsequent syntheses.

EXAMPLE 49

A The reaction is carried out in a way analogous to that described in Example 3, but from 3.7 g of methyl (2RS,4RS,5SR)-5-(2-fluorophenyl)-2-isobutylcarbamoyl-1-{2-[3-(3-(methoxycarbonylmethyl)phenyl)ureido]acetyl}pyrrolidine-4-carboxylate and 0.56 g of potassium hydroxide in a mixture of 20 cm³ of distilled water and 60 cm³ of methanol. After treatment, there are obtained 1.9 g of (2RS,4SR,5SR)-1-{2-[3-(3-(carboxymethyl)phenyl)ureido]acetyl}-5-(2-fluorophenyl)-2-(isobutylcarbamoyl)pyrrolidine-4-carboxylic acid $R_f$=0.155 eluant: methylene chloride/methanol (90/10)].

B Methyl (2RS,4RS,5SR)-5-(2-fluorophenyl)-2-isobutylcarbamoyl-1-{2-[3-(3-(methoxycarbonylmethyl)phenyl)ureido]acetyl}pyrrolidine-4-carboxylate can be prepared as described in Example 2B, but from 2.65 g of methyl (2RS,4RS,5SR)-5-(2-fluorophenyl)-2-(isobutylcarbamoyl)pyrrolidine-4-carboxylate, 1.34 g of 2-{3-[3-(methoxycarbonylmethyl)phenyl]ureido}acetic acid and 1.05 g of N,N'-dicyclohexylcarbodiimide in 50 cm³ of acetonitrile. After treatment, there are obtained 3.7 g of a mixture of methyl (2RS,4RS,5SR)-5-(2-fluorophenyl)-2-isobutylcarbamoyl-1-{2-[3-(3-(methoxycarbonylmethyl)phenyl)ureido]-acetyl}pyrrolidine-4-carboxylate and 1,3-dicyclohexylurea in the form of a foam used as is in the subsequent syntheses.

C Methyl (2RS,4RS,5SR)-5-(2-fluorophenyl)-2-(isobutylcarbamoyl)pyrrolidine-4-carboxylate can be prepared as described in Example 2C, but from 5.5 g of 2-(2-fluorobenzylideneamino)-N-isobutylacetamide, 2 cm³ of methyl acrylate, 5.46 g of silver acetate and 3.7 cm³ of triethylamine in 200 cm³ of acetontrile. After treatment, there are obtained 1.6 g of methyl (2RS,4RS,5SR)-5-(2-fluorophenyl)-2-(isobutylcarbamoyl)pyrrolidine-4-carboxylate in the form of an oil used as is in the subsequent syntheses.

EXAMPLE 50

A The reaction is carried out in a way analogous to that described in Example 3, but from 2.5 g of methyl (2RS,4RS,5SR)-5-(2-fluorophenyl)-1-{2-[3-(3-(methoxycarbonylmethyl)phenyl)ureido]acetyl}2-(morpholinocarbonyl)pyrrolidine-4-carboxylate and 0.48 g of potassium hydroxide in a mixture of 30 cm³ of distilled water and 60 cm³ of methanol. After treatment, there are obtained 1.1 g of (2RS,4SR,5SR)-1-{2-[3-(3-(carboxymethyl)phenyl)ureido]acetyl}-5-(2-fluorophenyl)-2-(morpholinocarbonyl)pyrrolidine-4-carboxylic acid [$R_f$= 0.15; eluent: methylene chloride/methanol (90/10)].

B Methyl (2RS,4RS,5SR)-5-(2-fluorophenyl)-1-{2-[3-(3-(methoxycarbonylmethyl)phenyl)ureido]acetyl}2-(morpholinocarbonyl)pyrrolidine-4-carboxylate can be prepared as described in Example 2B, but from 1.68 g of methyl (2RS,4RS,5SR)-5-(2-fluorophenyl)-2-(morpholinocarbonyl)pyrrolidine-4-carboxylate, 1.34 g of 2-{3-[3-(methoxycarbonylmethyl)phenyl]ureido}acetic acid and 1.05 g of N,N'-dicyclohexylcarbodiimide in 50 cm³ of acetonitrile. After treatment, there are obtained 2.5 g of methyl (2RS,4RS,5SR)-5-(2-fluorophenyl)-1-{2-[3-(3-(methoxycarbonylmethyl)phenyl)ureido]acetyl}-2-(morpholinocarbonyl)pyrrolidine-4-carboxylate in the form of a foam used as is in the subsequent syntheses.

C Methyl (2RS,4RS,5SR)-5-(2-fluorophenyl)-2-(morpholinocarbonyl)pyrrolidine-4-carboxylate can be prepared as described in Example 2C, but from 6 g of 4-[2-(2-fluorobenzylideneamino)acetyl]morpholine, 2.16 cm³ of methyl acrylate, 6 g of silver acetate and 4.05 cm³ of triethylamine in 200 cm³ of acetonitrile. After treatment, there are obtained 1.6 g of methyl (2RS,4RS,5SR)-5-(2-fluorophenyl)-2-(morpholinocarbonyl)pyrrolidine-4-carboxylate in the form of an oil used as is in the subsequent syntheses.

EXAMPLE 51

By carrying out the resolution as described in Example 37D, but from 1 g of (2RS,4SR,5RS)-3-{3-[2-(2-tert-butoxycarbonyl-5-(2-fluorophenyl)-4-phenylsulphonyl-1-pyrrolidinyl)-2-oxoethyl]ureido}benzoic acid in two injections on 400 g of support consisting of silica coated with cellulose tris (3,5-dimethylphenyl)carbamate with, as mobile phase, a hexane/ethanol (85/15) mixture at a flow rate of 40 cm³/minute, the laevorotatory and then the dextrorotatory enantiomer are successively eluted. The fractions containing each of the two enantiomers are combined and concentrated under reduced pressure. There are thus obtained 0.466 g of (2R*,4S*,5R*)-(−)-3-{3-[2-(2-tert-butoxycarbonyl-5-(2-fluorophenyl)-4-phenylsulphonyl-1-pyrrolidinyl)-2-oxoethyl]ureido}benzoic acid, the optical rotation of which is $[\alpha]_D^{20}$=−8.7° (c=0.5, methanol), then 0.490 g of (2R*,4S*,5R*)-(+)-3-{3-[2-(2-tert-butoxycarbonyl-5-(2-fluorophenyl)-4-phenylsulphonyl-1-pyrrolidinyl)-2-oxoethyl]ureido}benzoic acid, the optical rotation of which is $[\alpha]_D^{20}$=+10° (c=0.5, methanol).

EXAMPLE 52

By carrying out the resolution as described in Example 37D, but from 0.3 g of 2-tert-butyl hydrogen (2RS,4SR,5SR)1-{2-[3-(3-(carboxymethyl)phenyl)ureido]acetyl}5-(2-fluorophenyl)pyrrolidine-2,4-dicarboxylate in one injection on 400 g of support consisting of silica coated with cellulose tris(3,5-dimethylphenyl)carbamate with, as mobile phase, a hexane/ethanol (70/30) mixture at a flow rate of 40 cm³/minute, the dextrorotatory and then the laevorotatory isomer are successively eluted. The fractions containing each of the two enantiomers are combined and concentrated under reduced pressure. There are thus obtained:

0.135 g of 2-tert-butyl hydrogen (2R*,4S*,5S*)-(+)-1-{2-[3-(3-(carboxymethyl)phenyl)ureido]acetyl}-5-(2-fluorophenyl)pyrrolidine-2,4-dicarboxylate, the optical rotation of which is $[\alpha]_D^{20}$=+15.7° (c=0.5, methanol), then 0.121 g of 2-tert-butyl hydrogen (2R*,4S*,5S*)(−)-1-{2-[3-(3-(carboxymethyl)phenyl)ureido]acetyl}-5-(2-fluorophenyl)pyrrolidine-2,4-dicarboxylate, the optical rotation of which is $[\alpha]_D^{20}$=−20.3° (c=0.5, methanol).

EXAMPLE 53

A The reaction is carried out in a way analogous to that described in Example 3, but from 1.5 g of 2-tert-butyl 4-methyl (2RS,4RS,5SR)-5-cyclohexyl-1-{2-[3-(3-methylphenyl)ureido]acetyl}pyrrolidine-2,4-dicarboxylate and 0.17 g of potassium hydroxide in a mixture of 20 cm³ of distilled water and 60 cm³ of methanol. After treatment, there is obtained 0.5 g of 2-tert-butyl hydrogen (2RS,4RS, 5SR)-5-cyclohexyl-1-{2-[3-(3-methylphenyl)ureido]
acetyl}pyrrolidine-2,4-dicarboxylate [R$_f$=0.31; eluent:
methylene chloride/methanol (90/10)].

B 2-tert-Butyl 4-methyl (2RS,4RS,5SR)-5-cyclohexyl-1-
{2-[3-(3-methylphenyl)ureido]acetyl}pyrrolidine-2,4-
dicarboxylate can be prepared as described in Example 2B,
but from 1.25 g of 2-tert-butyl 4-methyl (2RS,4RS,5SR)-5-
(cyclohexyl)pyrrolidine-2,4-dicarboxylate, 0.83 g of 2-[3-
(3-methylphenyl)ureido]acetic acid and 0.83 g of N,N'-
dicyclohexylcarbodiimide in 35 cm$^3$ of acetonitrile. After
treatment, there are obtained 1.5 g of 2-tert-butyl 4-methyl
(2RS,4RS,5SR)-5-cyclohexyl-1-{2-[3-(3-methylphenyl)
ureido]acetyl}pyrrolidine-2,4-dicarboxylate in the form of a
foam used as is in the subsequent syntheses.

C 2-tert-Butyl 4-methyl (2RS,4RS,5SR)-5-(cyclohexyl)
pyrrolidine-2,4-dicarboxylate can be prepared as described
in Example 2C, but from 4.5 g of tert-butyl
cyclohexylmethyleneaminoacetate, 1.8 cm$^3$ of methyl
acrylate, 5 g of silver acetate and 2.8 cm$^3$ of triethylamine
in 200 cm$^3$ of acetonitrile. After treatment, there are
obtained 2.8 g of 2-tert-butyl 4-methyl (2RS,4RS,5SR)-5-
(cyclohexyl)pyrrolidine-2,4-dicarboxylate in the form of an
oil used as is in the subsequent syntheses.

D tert-Butyl cyclohexylmethyleneaminoacetate can be
prepared as described in Example 2D, but from 2.43 cm$^3$ of
cyclohexanecarbaldehyde, 3.4 g of tert-butyl glycinate
hydrochloride, 3 g of 4 Å sieve and 2.8 cm$^3$ of triethylamine
in 50 cm$^3$ of dichloromethane. After treatment, there are
obtained 4.5 g of tert-butyl cyclohexylmethyleneaminoac-
etate in the form of an oil used as is in the subsequent
syntheses.

EXAMPLE 54

A The reaction is carried out in a way analogous to that
described in Example 3, but from 0.95 g of 2-tert-butyl
4-methyl (2RS,4RS,5SR)-5-cyclohexyl-1-{2-[3-(3-
(methoxycarbonyl)phenyl)ureido]acetyl}pyrrolidine-2,4-
dicarboxylate and 0.20 g of potassium hydroxide in a
mixture of 15 cm$^3$ of distilled water and 50 cm$^3$ of methanol.
After treatment, there is obtained 0.25 g of 2-tert-butyl
hydrogen (2RS,4RS,5SR)-5-cyclohexyl-1-{2-[3-(3-
(carboxyphenyl)ureido]acetyl}pyrrolidine-2,4-
dicarboxylate, melting at 150° C.

B 2-tert-Butyl 4-methyl (2RS,4RS,5SR)-5-cyclohexyl-1-
{2-[3-(3-(methoxycarbonyl)phenyl)ureido]
acetyl}pyrrolidine-2,4-dicarboxylate can be prepared as
described in Example 2B, but from 1.4 g of 2-tert-butyl
4-methyl (2RS,4RS,5SR)-5-cyclohexylpyrrolidine-2,4-
dicarboxylate, 1.15 g of 2-{3-[3-(methoxycarbonyl)phenyl]
ureido}acetic acid and 0.93 g of N,N'-
dicyclohexylcarbodiimide in 50 cm$^3$ of acetonitrile. After
treatment, there is obtained 1.0 g of 2-tert-butyl 4-methyl
(2RS,4RS,5SR)-5-cyclohexyl-1-{2-[3-(3-
(methoxycarbonyl)phenyl)ureido]acetyl}pyrrolidine-2,4-
dicarboxylate in the form of a foam used as is in the
subsequent syntheses.

EXAMPLE 55

A The reaction is carried out in a way analogous to that
described in Example 3, but from 2.8 g of tert-butyl (2RS,
4SR,5SR)-1-{2-[3-(3-ethoxycarbonyl)phenyl)ureido]
acetyl}-5-(2-fluorophenyl)-4-(phenylcarbamoyl)
pyrrolidine-2-carboxylate in a mixture of 4.4 cm$^3$ of a
normal aqueous potassium hydroxide solution, 20 cm$^3$ of
distilled water and 100 cm$^3$ of methanol. After treatment,
there is obtained 0.11 g of (2RS,4SR,5SR)-3-{3-[2-(2-tert-
butoxycarbonyl-5-(2-fluorophenyl)-4-phenylcarbamoyl-1-
pyrrolidinyl)-2-oxoethyl]ureido}benzoic acid, melting at
170° C.

B tert-Butyl (2RS,4SR,5SR)-1-{2-[3-(3-ethoxycarbonyl)
phenol)ureido]acetyl}-5-(2-fluorophenyl)-4-
(phenylcarbamoyl)pyrrolidine-2-carboxylate can be pre-
pared as described in Example 17B, but from 2.5 g of
tert-butyl (2RS,4SR,5SR)-1-(2-aminoacetyl)-5-(2-
fluorophenyl)-4-(phenylcarbamoyl)pyrrolidine-2-
carboxylate and 1.27 g of ethyl 3-isocyanatobenzoate in 140
cm$^3$ of tetrahydrofuran. After treatment, there are obtained
2.9 g of tert-butyl (2RS,4SR,5SR)-1-{2-[3-(3-
ethoxycarbonyl)phenyl)ureido]acetyl}-5-(2-fluorophenyl)-
4-(phenylcarbamoyl)pyrrolidine-2-carboxylate in the form
of a foam used as is in the subsequent syntheses.

C tert-Butyl (2RS,4SR,5SR)-1-(2-aminoacetyl)-5-(2-
fluorophenyl)-4-(phenylcarbamoyl)pyrrolidine-2-
carboxylate can be prepared as described in Example 16C,
but from 3.1 g of tert-butyl (2RS,4SR,5SR)-1-[2-(tert-
butoxycarbomylamino)acetyl]-5-(2-fluorophenyl)-4-
(phenylcarbamoyl)pyrrolidine-2-carboxylate and 1.15 cm$^3$
of iodotrimethylsilane in 100 cm$^3$ of chloroform. After
treatment, there are obtained 2.5 g of tert-butyl (2RS,4SR,
5SR)-1-(2-aminoacetyl)-5-(2-fluorophenyl)-4-
(phenylcarbamoyl)pyrrolidine-2-carboxylate in the form of
a foam used as is in the subsequent syntheses.

D tert-Butyl (2RS,4SR,5SR)-1-[2-(tert-
butoxycarbonylamino)acetyl]-5-(2-fluorophenyl)-4-
(phenylcarbamoyl)pyrrolidine-2-carboxylate can be pre-
pared as described in Example 20D, but from 4.4 g of
2-tert-butyl hydrogen (2RS,4SR,5SR)-1-[2-(tert-
butoxycarbonylamino)acetyl]-5-(2-fluorophenyl)
pyrrolidine-2,4-dicarboxylate, 0.86 cm$^3$ of aniline and 1.95
g of N,N'-dicyclohexylcarbodiimide in 150 cm$^3$ of acetoni-
trile. After treatment, there are obtained 4.3 g of tert-butyl
(2RS,4SR,5SR)-1-[2-(tert-butoxycarbonylamino)acetyl]-5-
(2-fluorophenyl)-4-(phenylcarbamoyl)pyrrolidine-2-
carboxylate in the form of foam used as is in the subsequent
syntheses.

EXAMPLE 56

A The reaction is carried out in a way analogous to that
described in Example 3, but from 4.2 g of tert-butyl (2RS,
4SR,5SR)-1-{2-[3-(3-(ethoxycarbonyl)phenyl)ureido]
acetyl}-5-(2-fluorophenyl)-4-(isobutylcarbamoyl)
pyrrolidine-2-carboxylate in a mixture of 6.8 cm$^3$ of a
normal aqueous potassium hydroxide solution, 30 cm$^3$ of
distilled water and 140 cm$^3$ of methanol. After treatment,
there is obtained 0.65 g of (2RS,4SR,5SR)-3-{3-[2-(2-tert-
butoxycarbonyl-5-(2-fluorophenyl)-4-isobutylcarbamoyl-1-
pyrrolidinyl)-2-oxoethyl]ureido}benzoic acid, melting at
160° C.

B tert-Butyl (2RS,4SR,5SR)-1-{2-[3-(3-(ethoxycarbonyl)
phenyl)ureido]acetyl}-5-(2-fluorophenyl)-4-
(isobutylcarbamoyl)pyrrolidine-2-carboxylate can be pre-
pared as described in Example 17B, but from 5.2 g of
tert-butyl (2RS,4SR,5SR)-1-(2-aminoacetyl)-5-(2-
fluorophenyl)-4-(isobutylcarbamoyl)pyrrolidine-2-
carboxylate and 2.2 g of ethyl 3-isocyanatobenzoate in 140
cm$^3$ of tetrahydrofuran. After treatment, there are obtained
2.9 g of tert-butyl (2RS,4SR,5SR)-1-{2-[3-(3-
(ethoxycarbonyl)phenyl)ureido]acetyl}-5-(2-fluorophenyl)-
4-(isobutylcarbamoyl)pyrrolidine-2-carboxylate in the form
of a foam used as is in the subsequent syntheses.

C tert-Butyl (2RS,4SR,5SR)-1-(2-aminoacetyl)-5-(2-
fluorophenyl)-4-(isobutylcarbamoyl)pyrrolidine-2- carboxylate can be prepared as described in Example 16C, but from 7.4 g of tert-butyl (2RS,4SR,5SR)-1-[2-(tert-butoxycarbonylamino)acetyl]-5-(2-fluorophenyl)-4-(isobutylcarbamoyl)pyrrolidine-2-carboxylate and 2.8 cm³ of iodotrimethylsilane in 350 cm³ of chloroform. After treatment, there are obtained 5.2 g of tert-butyl (2RS,4SR,5SR)-1-(2-aminoacetyl)-5-(2-fluorophenyl)-4-(isobutylcarbamoyl)pyrrolidine-2-carboxylate in the form of a foam used as is in the subsequent syntheses.

D tert-Butyl (2RS,4SR,5SR)-1-[2-(tert-butoxycarbonylamino)acetyl]-5-(2-fluorophenyl)-4-(isobutylcarbamoyl)pyrrolidine-2-carboxylate can be prepared as described in Example 26D, but from 5.6 g of 2-tert-butyl hydrogen (2RS,4SR,5SR)-1-[2-(tert-butoxycarbonylamino)acetyl]-5-(2-fluorophenyl) pyrrolidine-2,4-dicarboxylate, 2.15 g of N,N-carbonyldiimidazole, 50 mg of 4-dimethylaminopyridine and 0.88 cm³ of isobutylamine in 180 cm³ of 1,2-dichloroethane. After treatment, there are obtained 6 g of tert-butyl (2RS,4SR,5SR)-1-[2-(tert-butoxycarbonylamino) acetyl]-5-(2-fluorophenyl)-4-(isobutylcarbamoyl) pyrrolidine-2-carboxylate in the form of a foam used as is in the subsequent syntheses.

EXAMPLE 57

A solution of 0.7 g of tert-butyl (2RS,4SR,5SR)-4-acetoxymethyl-1-[3-(3-methylphenyl)-2-ureidoacetyl]-5-phenylpyrrolidine-2-carboxylate and 77 mg of potassium hydroxide in a mixture of 3 cm³ of distilled water and 9 cm³ of methanol is stirred for twenty hours at a temperature in the region of 20° C. The reaction mixture is then concentrated under reduced pressure and the residue taken up in 50 cm³ of ethyl acetate. The organic phase is washed with three times 20 cm³ of distilled water, dried over magnesium sulphate and concentrated under reduced pressure. The residue is crystallized from 50 cm³ of pantene and recrystallized from a mixture of 40 cm³ of cyclohexane and 20 cm³ of ethyl acetate. There is thus obtained 0.39 g of tert-butyl (2RS,4SR,5SR)-4-hydroxymethyl-1-[3-(3-methylphenyl)-2-ureidoacetyl]-5-phenylpyrrolidine-2-carboxylate, melting at 168° C.

B tert-Butyl (2RS,4SR,5SR)-4-acetoxymethyl-1-[3-(3-methylphenyl)-2-ureidoacetyl]-5-phenylpyrrolidine-2-carboxylate can be prepared as described in Example 17B, but from 0.81 g of tert-butyl (2RS,4SR,5SR)-4-acetoxymethyl-1-(2-aminoacetyl)-5-phenylpyrrolidine-2-carboxylate and 0.25 cm³ of meta-tolyl isocyanate in 10 cm³ of tetrahydrofuran. After treatment, there is obtained 0.8 g of tert-butyl (2RS,4SR,5SR)-4-acetoxymethyl-1-[3-(3-methylphenyl)-2-ureidoacetyl]-5-phenylpyrrolidine-2-carboxylate in the form of an oil used as is in the subsequent syntheses.

C tert-Butyl (2RS,4SR,5SR)-4-acetoxymethyl-1-(2-aminoacetyl)-5-phenylpyrrolidine-2-carboxylate can be prepared as described in Example 16C, but from tert-butyl (2RS,4SR,5SR)-4-acetoxymethyl-1-[2-(tert-butoxycarbonylamino)acetyl]-5-phenylpyrrolidine-2-carboxylate and 0.29 cm³ of iodotrimethylsilane in 10 cm³ of chloroform. After treatment, there is obtained 0.82 g of tert-butyl (2RS,4SR,5SR)-4-acetoxymethyl-1-(2-aminoacetyl)-5-phenylpyrrolidine-2-carboxylate in the form of an oil used as is in the subsequent syntheses.

D tert-Butyl (2RS,4SR,5SR)-4-acetoxymethyl-1-[2-(tert-butoxycarbonylamino)acetyl]-5-phenylpyrrolidine-2-carboxylate can be prepared in the following way: 0.27 cm³ of acetyl chloride is added, at a temperature in the region of 5° C., to a solution of 1.5 g of tert-butyl (2RS,4SR,5SR)-1-[2-(tert-butoxycarbonylamino)acetyl]-4-hydroxymethyl-5-phenylpyrrolidine-2-carboxylate in a mixture of 0.64 cm³ of triethylamine and 50 cm³ of dichloromethane. The reaction mixture is stirred for twenty hours at a temperature in the region of 20° C. and is then washed with three times 30 cm³ of distilled water. The aqueous phases are extracted with 20 cm³ of dichloromethane and the organic phases are then combined, dried over magnesium sulphate and concentrated under reduced pressure. The residue is purified by chromatography on silica [eluent: cyclohexane/ethyl acetate (70/30 by volume)]. The fractions containing the expected products are combined and concentrated under reduced pressure. There is thus obtained 1 g of tert-butyl (2RS,4SR,5SR)-4-acetoxymethyl-1-[2-(tert-butoxycarbonylamino) acetyl]-5-phenylpyrrolidine-2-carboxylate in the form of an oil used as is in the subsequent syntheses.

E tert-Butyl (2RS,4SR,5SR)-1-[2-(tert-butoxycarbonylamino)acetyl]-4-hydroxymethyl-5-phenylpyrrolidine-2-carboxylate can be prepared in the following way: 1.2 g of sodiumborohydride are added, at a temperature in the region of 20° C. to a solution of 4 g of 2-tert-butyl 4-methyl (2RS,4RS,5SR)-1-[2-(tert-butoxycarbonylamino)acetyl]-5-phenylpyrrolidine-2,4-dicarboxylate in 50 cm³ of tert-butanol. The reaction mixture is heated to reflux and 9.7 cm³ of methanol are added. The mixture is then stirred at reflux for forty minutes, then cooled to a temperature in the region of 20° C., hydrolysed with 100 cm³ of distilled water and concentrated under reduced pressure. The aqueous residue is saturated with an excess of sodium chloride and extracted with three times 30 cm³ of diethyl ether. The organic phases are combined, dried over magnesium sulphate and concentrated under reduced pressure. The residue is purified by chromatography on silica [eluent: cyclohexane/ethyl acetate (30/70 by volume)]. The fractions containing the expected product are combined and concentrated under reduced pressure. There are thus obtained 1.6 g of tert-butyl (2RS,4SR,5SR)-1-[2-(tert-butoxycarbonylamino)acetyl]-4-hydroxymethyl-5-phenylpyrrolidine-2-carboxylate in the form of an oil used as is in the subsequent syntheses.

EXAMPLE 58

A The reaction is carried out in a way analogous to that described in Example 3, but from 0.6 g of 2-tert-butyl 4-methyl (2R*,4R*,5S*)-(−)-5-(2-fluorophenyl)-1-{2-[3-(3-(methoxycarbonylmethyl)phenyl)ureido]acetyl}pyrrolidine-2,4-dicarboxylate and 0.12 g of potassium hydroxide in a mixture of 10 cm³ of distilled water and 25 cm³ of methanol. After treatment, there is obtained 0.37 g of 2-tert-butyl hydrogen (2R*,4S*,5S*)-(+)-1-{2-[3-(3-(carboxymethyl)phenyl)ureido]acetyl}-5-(2-fluorophenyl) pyrrolidine-2,4-dicarboxylate, the spectroscopic analyses of which are in accordance with those of the first product of Example 52.

B 2-tert-Butyl 4-methyl (2R*,4R*,5S*)-(−)-5-(2-fluorophenyl)-1-{2-[3-(3-(methoxycarbonylmethyl)phenyl) ureido]acetyl}pyrrolidine-2,4-dicarboxylate can be prepared as described in Example 2B, but from 1 g of 2-tert-butyl 4-methyl (2R*,4R*,5S*)-5-(2-fluorophenyl)pyrrolidine-2,4-dicarboxylate (enantiomer A), 0.82 g of 2-{3-[3-(methoxycarbonylmethyl)phenyl]ureido}acetic acid and 0.64 g of N,N'-dicyclohexylcarbodiimide in 50 cm³ of acetonitrile. After treatment, there is obtained 0.6 g of 2-tert-butyl 4-methyl (2R*,4R*,5S*)-(−)-5-(2-fluorophenyl) -1-{2-[3-(3-(methoxycarbonylmethyl)phenyl)ureido] acetyl}pyrrolidine-2,4-dicarboxylate in the form of a foam used as is in the subsequent syntheses.

C 2-tert-Butyl 4-methyl (2R*,4R*,5S*)-5-(2-fluorophenyl)pyrrolidine-2,4-dicarboxylate (enantiomer A) can be prepared in the following way: a solution of 2.18 g of 2-tert-butyl 4-methyl (2R*,4R*,5S*)-5-(2-fluorophenyl)-1-[(S)-3-phenyl-2-(3-phenylthioureido)propionyl] pyrrolidine-2,4-dicarboxylate (form A) in a mixture of 25 cm$^3$ of dichloromethane and 1.76 cm$^3$ of trifluoroacetic acid is stirred at a temperature in the region of 20° C. for seven hours. The reaction mixture is then poured into 150 cm$^3$ of a saturated aqueous sodium hydrogencarbonate solution. The organic phase is separated by settling, washed with two times 50 cm$^3$ of distilled water, dried over magnesium sulphate and concentrated under reduced pressure. The residue is purified by chromatography on silica [eluent: cyclohexane/ethyl acetate (85/15 then 70/30 by volume)]. The fractions containing the expected product are combined and concentrated under reduced pressure. There is thus obtained 1 g of 2-tert-butyl 4-methyl (2R*,4R*,5S*)-5-(2-fluorophenyl)pyrrolidine-2,4-dicarboxylate (enantiomer A) in the form of an oil used as is in the subsequent syntheses.

D 2-tert-Butyl 4-methyl (2R*,4R*,5S*)-5-(2-fluorophenyl)-1-[(S)-3-phenyl-2-(3-phenylthioureido)propionyl]pyrrolidine-2,4-dicarboxylate (form A) can be prepared as described in Example 17B, but from 1.8 g of 2-tert-butyl 4-methyl missing end of line 1-[(S)-2-amino-3-phenylpropionyl]-5-(2-fluorophenyl)pyrrolidine-2,4-dicarboxylate (form A) and 0.5 cm$^3$ of phenyl isothiocyanate in 100 cm$^3$ of dichloromethane. After treatment, there is obtained 2.18 g of 2-tert-butyl 4-methyl (2R*,4R*,5S*)-5-(2-fluorophenyl)-1-[(S)-3-phenyl-2-(3-phenylthioureido)propionyl]pyrrolidine-2,4-dicarboxylate (form A) in the form of a foam used as is in the subsequent syntheses.

B 2-tert-Butyl 4-methyl (2R*,4R*,5S*)-1-[(S)-2-amino-3-phenylpropionyl]-5-(2-fluorophenyl)pyrrolidine-2,4-dicarboxylate (form A) can be prepared in the following way: 0.38 g of 10% palladium-on-charcoal is added, at a temperature in the region of 20° C., to a solution of 2.3 g of 2-tert-butyl 4-methyl (2R*,4R*,5S*)-1-[(S)-2-(benzyloxycarbonylamino)-3-phenylpropionyl]-5-(2-fluorophenyl)pyrrolidine-2,4-dicarboxylate (form A) in 150 cm$^3$ of ethanol. The reaction mixture is stirred for six hours under a hydrogen atmosphere (130 kPa). The catalyst is separated by filtration on Celite, rinsed with two times 10 cm$^3$ of methanol and the filtrate is concentrated to dryness under reduced pressure. There are thus obtained 1.8 g of 2-tert-butyl 4-methyl (2R*,4R*,5S*)-1-[(S)-2-amino-3-phenylpropionyl]-5-(2-fluorophenyl)pyrrolidine-2,4-dicarboxylate (form A) in the form of an oil used as is in the subsequent syntheses.

F 2-tert-Butyl 4-methyl (2R*,4R*,5S*)-1-[(S)-2-(benzyloxycarbonylamino)-3-phenylproplonyl]-5-(2-fluorophenyl)pyrrolidine-2,4-dicarboxylate (form A) can be prepared as described in Example 16D, but from 3.23 g of 2-tert-butyl 4-methyl (2RS,4RS,5SR)-5-(2-fluorophenyl)pyrrolidine-2,4-dicarboxylate, 2.99 g of (S)-N-(benzyloxycarbonyl)phenylalanine and 2.06 g of N,N'-dicyclohexylcarbodiimide in 60 cm$^3$ of acetonitrile. After treatment, there are obtained, in order of solution:

2.32 g of 2-tert-butyl 4-methyl (2R*,4R*,5S*)-1-[(S)-2-(benzyloxycarbonylamino)-3-phenylpropionyl]-5-(2-fluorophenyl)pyrrolidine-2,4-dicarboxylate (form A), then 1.24 g of 2-tert-butyl 4-methyl (2R*,4R*,5S*)-1-[(S)-2-(benzyloxycarbonylamino)-3-phenylpropionyl]-5-(2-fluorophenyl)pyrrolidine-2,4-dicarboxylate (form B) in the form of white foams used as are in the subsequent syntheses.

EXAMPLE 59

A The reaction is carried out in a way analogous to that described in Example 3, but from 4.4 g of tert-butyl (2RS,4SR,5SR)-4-benzylcarbamoyl-1-{2-[3-(3-(ethoxycarbonyl)phenyl)ureido]acetyl}-5-(2-fluorophenyl)pyrrolidine-2-carboxylate and 0.38 g of potassium hydroxide in 40 cm$^2$ of distilled water and 150 cm$^3$ of methanol. After treatment, there is obtained 0.14 g of (2RS,4SR,5SR)-3-(3-{2-[4-benzylcarbamoyl-2-(tert-butoxycarbonyl-5-(2-fluorophenyl)-1-pyrrolidinyl]-2-oxoethyl}ureido)benzoic, melting at 217° C.

B tert-Butyl (2RS,4SR,5SR)-4-benzylcarbamoyl-1-{2-[3-(3-(ethoxycarbonyl)phenyl)ureido]acetyl}-5-(2-fluorophenyl)pyrrolidine-2-carboxylate can be prepared as described in Example 17B, but from 3.5 g of tert-butyl (2RS,4SR,5SR)-1-(2-aminoacetyl)-4-benzylcarbamoyl-5-(2-fluorophenyl)pyrrolidine-2-carboxylate and 1.43 g of ethyl 3-isocyanatobenzoate in 140 cm$^3$ of tetrahydrofuran. After treatment, there are obtained 4.5 g of tert-butyl (2RS,4SR,5SR)-4-benzylcarbamoyl-1-{2-[3-(3-(ethoxycarbonyl)phenyl)ureido]acetyl}-5-(a-fluorophenyl)pyrrolidine-2-carboxylate in the form of a foam used as is in the subsequent syntheses.

C tert-Butyl (2RS,4SR,5SR)-1-(2-aminoacetyl)-4-benzylcarbamoyl-5-(2-fluorophenyl)pyrrolidine-2-carboxylate can be prepared as described in Example 16C, but from 4.15 g of tert-butyl (2RS,4SR,5SR)-4-benzylcarbamoyl-1-[2-tert-butoxycarbonylamino)acetyl]-5-(2-fluorophenyl)pyrrolidine-2-carboxylate and 1.07 cm$^3$ of iodotrimethylsilane in 150 cm$^3$ of chloroform. After treatment, there are obtained 3.5 g of tert-butyl (2RS,4SR,5SR)-1-(2-aminoacetyl)-4-benzylcarbamoyl-5-(2-fluorophenyl)pyrrolidine-2-carboxylate in the form of an oil used as is in the subsequent syntheses.

D tert-Butyl (2RS,4SR,5SR)-4-benzylcarbamoyl-1-[2-(tert-butoxycarbonylamino)acetyl]-5-(2-fluorophenyl)pyrrolidine-2-carboxylate can be prepared as described in Example 26D, but from 6.1 g of 2-tert-butyl hydrogen (2RS,4SR,5SR)-1-[2-(tert-butoxycarbonylamino)acetyl]-5-(2-fluorophenyl)pyrrolidine-2,4-dicarboxylate, 2.1 g of N,N-carbonyldiimidazole, 50 mg of 4-dimethylaminopyridine and 1.43 cm$^3$ of benzylamine in 180 cm$^3$ of 1,2-dichloroethane. After treatment, there are obtained 4.3 g of tert-butyl (2RS,4SR,5SR)4-benzylcarbamoyl-1-[2-(tert-butoxycarbonylamino)acetyl]-5-(2-fluorophenyl)pyrrolidine-2-carboxylate in the form of a lacquer used as is in the subsequent syntheses.

The medicaments according to the invention consist of a compound of formula (I) in the free form or in the form of a pharmaceutically acceptable salt, in the pure state or in the form of a composition in which it is combined with any other pharmaceutically compatible product, which can be inert or physiologically active. The medicaments according to the invention can be employed orally, parenterally, rectally or topically.

Tablets, pills, powders (gelatin capsules or cachets) or granules can be used as solid compositions for oral administration. In these compositions, the active principle according to the invention is mixed with one or a number of inert diluents, such as starch, cellulose, sucrose, lactose or silica, under an argon stream. These compositions can also comprise substances other than the diluents, for example one or a number of lubricating agents such as magnesium stearate or talc, a colouring agent, a coating agent (dragées) or varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These compositions can comprise substances other than the diluents, for example wetting, sweetening, thickening, flavouring or stabilizing substances.

The sterile compositions for parenteral administration can preferably be suspensions, emulsions or non-aqueous or aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of solid sterile compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eyedrops, mouthwashes, nose-drops or aerosols.

In human therapeutics, the compounds according to the invention are particularly useful in the treatment and prevention of disorders linked to CCK and to gastrin in the nervous system and the gastrointestinal system. These compounds can thus be used in the treatment and prevention of psychoses, of anxious disorders, of depression, of neurodegeneration, of panic attacks, of Parkinson's disease, of tardive dyskinesia, of irritable bowel syndrome, of acute pancreatitis, of ulcers, of disorders of intestinal motility, of certain tumours sensitive to CCK, of memory disorders, in weaning from chronic treatments and alcohol or medicinal abuse, as constrictors of the pupil of the eye, as analgesics, as potentiating agents of the analgesic activity of narcotic and non-narcotic analgesic medicaments and as appetite regulators.

The doses depend on the desired effect, on the duration of treatment and on the administration route used; they are generally between 0.05 g and 1 g per day orally for an adult with unit doses ranging from 10 mg to 500 mg of active substance.

Generally, the doctor will determine the appropriate dosage depending on the age, weight and all the other factors specific to the subject to be treated.

The following examples illustrate compositions according to the invention:

EXAMPLE A

Gelatin capsules containing 50 mg of active product are prepared, according to the usual technique, which have the following composition:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50 mg of active product are prepared, according to the usual technique, which have the following composition:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) q.s. for 1 coated tablet completed to | 245 mg |

EXAMPLE C

An injectable solution containing 10 mg of active produce is prepared which has the following composition:

| | |
|---|---|
| Compound of formula (I) | 10 mg |
| Benzoic acid | 80 mg |
| Benzyl alcohol | 0.06 cm$^3$ |
| Sodium benzoate | 80 mg |
| 95% Ethanol | 0.4 cm$^3$ |
| Sodium hydroxide | 24 mg |
| Propylene glycol | 1.6 cm$^3$ |
| Water | q.s. for 4 cm$^3$ |

We claim:
1. A compound of formula (I):

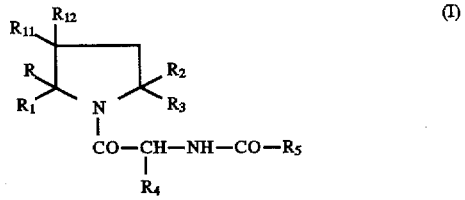

in which

R represents a phenyl radical optionally substituted by at least one substituent selected from halogen atoms and alkyl, alkoxy, hydroxyl, nitro, amino, monoalkylamino, dialkylamino, alkoxycarbonyl, —CO—NR$_7$R$_8$, —NH—CO—CH$_3$, trifluoromethyl and trifluoromethoxy radicals, R$_1$ represents a hydrogen atom or an alkyl radical, R$_2$ represents a —(CH$_2$)$_n$—CO—R$_6$ or —(CH$_2$)$_m$—NR$_9$R$_{10}$ chain, R$_3$ represents a hydrogen atom or an alkyl radical, R$_4$ represents a hydrogen atom or an alkyl radical, R$_5$ represents a phenylamino radical in which the phenyl ring is optionally substituted by at least one substituent selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-SO$_3$—H (in the salt form), —CH=CH-alk', —C(=NOH)—COOX, —S-alk-COOX, —SO-alk-COOX, —SO$_2$-alk-COOX, —O—CH$_2$-alk'-COOX, —CX=N—O-alk—COOX, -alk-N(OH)—CO-alk, -alk-SO$_2$H, —SO$_2$—NH—CO—R$_{13}$, —SO$_2$—NH—SO$_2$—R$_{13}$, —CO—NH—CO—R$_{13}$, —CO—NH—SO$_2$—R$_{13}$, —B(OH)$_2$, —C(NH$_2$)=NOH, —SO$_2$—NH—R$_{14}$, —CO—NH—R$_{14}$,

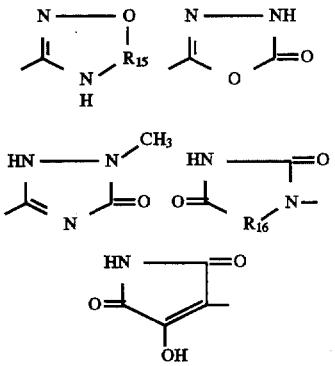

and 2,2-dimethyl-4,6-dioxo-1,3-dioxan-5-yl radicals,

R$_6$ represents a hydroxyl, alkoxy, cycloalkyloxy, cycloalkylalkyloxy, phenyl, or —NR$_9$R$_{10}$ radical, R"$_6$ represents an alkoxy, cycloalkyloxy, cycloalkylalkyloxy, phenyl, or —NR$_9$R$_{10}$ radical, R$_7$ represents a hydrogen atom or an alkyl radical, phenylalkyl radical or phenyl radical optionally substituted by at least one substitutent selected from halogen atoms and alkyl, alkoxy and alkylthio radicals, R$_8$ represents an alkyl radical, phenylalkyl radical or phenyl radical optionally substituted by at least one substituent selected from halogen atoms and alkyl, alkoxy and alkylthio radicals, or else R$_7$ and R$_8$ form, with the nitrogen atom to which they are attached, a saturated or unsaturated, mono- or polycyclic heterocycle containing 4 to 9 carbon atoms and at least one heteroatom selected from oxygen and nitrogen, and being optionally substituted by at least one alkyl radical, R$_9$ represents a hydrogen atom or an alkyl radical, cycloalkylalkyl radical, cycloalkyl radical, phenylalkyl radical or phenyl radical optionally substituted by at least one substituent selected, from halogen atoms and alkyl, alkoxy and alkylthio radicals, R$_{10}$ represents an alkyl radical, cycloalkylalkyl radical, cycloalkyl radical, phenylalkyl radical or phenyl radical optionally substituted by at least one substituent selected from halogen atoms and alkyl, alkoxy and alkylthio radicals, or else R$_9$ and R$_{10}$ form, together with the nitrogen atom to which they are attached, a saturated or unsaturated, mono- or polycyclic heterocycle containing 4 to 9 carbon atoms and at least one heteroatom selected from oxygen, nitrogen and sulfur, and optionally being substituted by at least one alkyl radical, R$_{11}$ represents a hydrogen atom or an alkyl or phenylalkyl radical, R$_{12}$ represents an alkyl, phenylalkyl, phenylsulphonyl, —(CH$_2$)$_p$—CO—R$_{17}$, cyano, —CXO, —CX=NOH, —CX=N—O-alk-COOX, —CHX—OH, —CHX—O—CO-alk, —NH$_2$ or —NH—CO-alk radical, R$_{13}$ represents an alkyl radical, a trifluoromethyl radical, a cycloalkyl radical or a phenyl radical optionally substituted by at least one substituent selected from cyano, alkoxy, nitro and amino radicals and halogen atoms, R$_{14}$ represents a 5-tetrazolyl radical, R$_{15}$ represents C=O or S=O, R$_{16}$ represents O or C=O, R$_{17}$ represents a hydroxyl, alkoxy, cycloalkyloxy, cycloalkylalkyloxy, phenyl, phenylalkoxy, alkyl or —NR$_9$R$_{10}$ radical, n is equal to 0, 1 or 2, m is equal to 1 or 2, p is equal to 0 or 1, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical, it being understood that, except when otherwise mentioned, the alkyl, alkylene and alkoxy radicals and the alkyl, alkylene and alkoxy portions of radicals contain 1 to 4 carbon atoms in a straight or branched chain, the acyl radicals and portions of radicals contain 2 to 4 carbon atoms and the cycloalkyl radicals and portions of radicals contain 3 to 6 carbon atoms, or a salt of a compound of formula (I) or an isomer of a compound of formula (I) when said isomer contains at least one asymmetric center.

2. A compound of formula (I) according to claim 1 for which R$_7$ and R$_8$ form, together with the nitrogen atom to which they are attached, a heterocycle selected from a piperidino ring optionally substituted by at least one alkyl or 1,2,3,4-tetrahydroquinoline radical, or a salt of one of said compounds or an isomer of one of said compounds when said isomer contains at least one asymmetric center.

3. A compound of formula (I) according to claim 1 for which R$_9$ and R$_{10}$ form, together with the nitrogen atom to which they are attached, a heterocycle selected from piperidino, 1-perhydroazepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino and 1-indolinyl rings, it being possible for these rings to be optionally substituted by at least one alkyl radical, or a salt of one of said compounds or an isomer of one of said compounds when said isomer contains at least one asymmetric center.

4. A compound of formula (I) according to claim 1 for which R represents a phenyl radical optionally substituted by at least one halogen atom, R$_1$ represents a hydrogen atom, R$_2$ represents a —(CH$_2$)$_n$—CO—R$_6$ chain, R$_3$ represents a hydrogen atom, R$_4$ represents a hydrogen atom, R$_5$ represents a phenylamino radical in which the phenyl ring is substituted by at least one substituent selected from carboxyl, —S-alk-COOX, -alk-COOX and 5-tetrazolyl radicals, R$_6$ represents a hydroxyl or alkoxy radical, R$_{11}$ represents a hydrogen atom, R$_{12}$ represents a phenylsulphonyl or —(CH$_2$)$_p$—CO—R$_{17}$ radical, R$_{17}$ represents a hydroxyl, phenyl or —NR$_9$R$_{10}$ radical, p is equal to 0, n is equal to 0, X represents a hydrogen atom, R$_9$ and R$_{10}$ have the same meanings as in claim 1, or a salt of one of said compounds or an isomer of one of said compounds when said isomer contains at least one asymmetric center.

5. A compound, said compound being:

(2RS,4SR,5RS)-3-{3-[2-(2-tert-butoxycarbonyl-5-phenyl-4-phenylsulphonyl-1-pyrrolidinyl)-2-oxoethyl]-ureido}benzoic acid, 2-tert-butyl hydrogen (2RS,4SR,5SR)-1-{2-[3-(3-(carboxymethylthio)phenyl)ureido]acetyl}-5-phenylpyrrolidine-2,4-dicarboxylate, (2RS,4SR,5RS)-3-{-3-[2-(2-tert-butoxycarbonyl-5-(2-flurophenyl)-4-phenylsulphonyl-1-pyrrolidinyl)-2-oxoethyl]ureido}benzoic acid, (2RS,4SR,5RS)-3-{3-[2-(2-(3,3-dimethylpiperidinocarbonyl)-5-(2-fluorophenyl)-4-phenylsulphonyl-1-pyrrolidinyl)-2-oxoethyl]ureido}benzoic acid, 2-tert-butyl hydrogen (2RS,4SR,5SR)-1-{2-[3-(3-(carboxymethyl)phenyl)ureido]acetyl}-5-2-fluorophenyl)-pyrrolidine-2,4-dicarboxylate, (2RS,4SR,5RS)-3-{3-[2-(2-tert-butoxycarbonyl-5-(2-fluorophenyl)-4-phenylsulphonyl-1-pyrrolidinyl)-2-oxoethyl]ureido}phenylacetic acid, (2RS,4SR,5SR)-3-{3-[2-(2-tert-butoxycarbonyl-5-phenyl-4-(1-pyrrolidinylcarbonyl)-1-pyrrolidinyl)-2-oxoethyl]ureido}benzoic acid, (2RS,4SR,5SR)-3-{3-[2-(2-tert-butoxycarbonyl-4-dimethylcarbamoyl-5-phenyl-1-pyrrolidinyl)-4-dimethylcarbamoyl-5-phenyl-1-pyrrolidinyl)-2-oxoethyl]ureido}benzoic acid, (2RS-4SR,5SR)-3-{3-[2-(4-benzoyl-2-tert-butoxycarbonyl-5-(2-fluorophenyl)-1-pyrrolidinyl)-2-oxoethyl]ureido}benzoic acid, 2-{3-[3-(2-((2R*,4S*,5R*)-2-tert-butoxycarbonyl-5-(2-fluorophenyl)-4-phenylsulphonyl-1-pyrrolidinyl)-2-oxoethyl)ureido]phenyl}propionic acid, (S)-2-{3-[3-(2-((2R*,4S*,5R*)-2-tert-butoxycarbonyl-5-(2-fluorophenyl)-4-phenylsulphonyl-1-pyrrolidinyl)-2-oxoethyl)ureido]phenyl}-2-methoxyacetic acid, (2RS,4SR,5SR)-3-{3-[2-(2-tert-butoxycarbonyl-5-(2-fluorophenyl)-4-morpholinocarbonyl-1-pyrrolidinyl)-2-oxoethyl]ureido}benzoic acid, (2RS,4SR,5SR)-3-[3-[2-(2-tert-butoxycarbonyl-4-diethylaminocarbonyl-5-(2-fluorophenyl)-1-pyrrolidinyl)-2-oxoethyl]ureido}benzoic acid, (2RS,4SR,5SR)-5-{3-[3-(2-(2-tert-butoxycarbonyl-5-(2-florophenyl)-4-phenylsulphonyl-1-pyrrolidinyl)-2-oxoethyl)ureido]phenyl}tetrazole, (2RS,4SR,5RS)-3-{3-[2-(5-(2-fluorophenyl)-2-isobutylcarbamoyl-4-phenylsulphonyl-1-pyrrolidinyl)-2-oxoethyl]ureido}phenylacetic acid, (2R*,4S*,5R*)-(−)-3-{3-[2-(2-tert-butoxycarbonyl-5-(2-fluorophenyl)-4-phenylsulphonyl-1-pyrrolidinyl)-2-oxoethyl]ureido}benzoic acid, or 2-tert-butyl hydrogen (2R*,4S*,5S*)-(+)-1-{2-[3-(3-carboxymethyl)-phenyl)ureido]acetyl}-5-(2-fluorophenyl)pyrrolidine-2,4-dicarboxylate, or a salt of one of said compounds or an isomer of one of said compounds when said isomer contains at least one asymmetric center.

6. A pharmaceutical composition, which comprises an effective amount of a compound of formula I as claimed in claim 1 together with a pharmaceutically acceptable carrier.

7. A method for treating disorders linked to cholecystokinin and to gastrin, which comprises administering to a host in need of said treatment an effective amount of a compound of the formula I as claimed in claim 1.

* * * * *